US005444042A

United States Patent [19]
Bartus et al.

[11] Patent Number: 5,444,042
[45] Date of Patent: Aug. 22, 1995

[54] METHOD OF TREATMENT OF NEURODEGENERATION WITH CALPAIN INHIBITORS

[75] Inventors: Raymond T. Bartus, Laguna Hills; David D. Eveleth, Irvine, both of Calif.; James C. Power, Atlanta, Ga.

[73] Assignees: Cortex Pharmaceuticals, Irvine, Calif.; Georgia Tech Research Corporation (GTRC), Atlanta, Ga.

[21] Appl. No.: 207,881

[22] Filed: Mar. 7, 1994

Related U.S. Application Data

[63] Continuation of Ser. No. 816,120, Dec. 27, 1991, abandoned, which is a continuation-in-part of Ser. No. 682,925, Apr. 9, 1991, abandoned, which is a continuation of Ser. No. 635,952, Dec. 28, 1990.

[51] Int. Cl.$^6$ ............ A61K 37/00; C12Q 1/37; C12N 9/99
[52] U.S. Cl. .................. 514/2; 514/16; 514/17; 514/18; 514/457; 435/23; 435/184
[58] Field of Search ............ 514/2, 16, 17, 18, 457, 514/460; 435/23, 184, 219

[56] References Cited

U.S. PATENT DOCUMENTS

| | | | |
|---|---|---|---|
| 3,651,091 | 3/1972 | Boschetti | 260/343.2 |
| 4,179,447 | 12/1979 | Connor et al. | 260/345.2 |
| 4,221,914 | 9/1980 | Bey et al. | 548/342 |
| 4,303,592 | 12/1981 | Laura et al. | 260/543 F |
| 4,305,872 | 12/1981 | Johnston et al. | 530/330 |
| 4,342,780 | 8/1982 | Bey et al. | 424/319 |
| 4,452,811 | 6/1984 | della Valle | 424/281 |
| 4,499,065 | 2/1985 | Calenoff et al. | 424/9 |
| 4,499,082 | 2/1985 | Shenvi et al. | 514/2 |
| 4,518,528 | 5/1985 | Rasnick | 260/112.5 R |
| 4,539,312 | 9/1985 | Delaney et al. | 514/16 |
| 4,560,795 | 12/1985 | Bey et al. | 562/561 |
| 4,636,492 | 1/1987 | Kettner et al. | 514/18 |
| 4,643,991 | 2/1987 | Digenis et al. | 514/18 |
| 4,644,055 | 2/1987 | Kettner et al. | 530/330 |
| 4,657,893 | 4/1987 | Krantz et al. | 514/18 |
| 4,659,855 | 4/1987 | Powers | 558/23 |
| 4,666,425 | 5/1987 | Fleming | 604/4 |
| 4,696,913 | 9/1987 | Geiger et al. | 514/15 |
| 4,714,757 | 12/1987 | Gordon et al. | 530/329 |
| 4,725,545 | 2/1988 | Powers | 435/218 |
| 4,732,910 | 3/1988 | Yaginuma et al. | 514/475 |
| 4,769,323 | 9/1988 | Murao et al. | 435/16 |
| 4,771,123 | 9/1988 | Cho | 530/323 |
| 4,777,269 | 10/1988 | Scheper et al. | 549/288 |
| 4,797,471 | 1/1989 | Teetz et al. | 514/18 |
| 4,837,222 | 6/1989 | Gregson et al. | 514/422 |
| 4,845,195 | 7/1989 | Colonno et al. | 530/330 |
| 4,845,242 | 7/1989 | Powers | 549/283 |
| 4,847,202 | 7/1989 | Powers | 435/184 |
| 4,851,388 | 7/1989 | Bright | 514/18 |
| 4,888,283 | 12/1989 | Bertini et al. | 435/184 |
| 4,891,356 | 1/1990 | Szabo | 514/2 |
| 5,037,957 | 8/1991 | Grubb | 530/330 |
| 5,055,451 | 9/1991 | Krantz | 514/19 |
| 5,068,354 | 11/1991 | Murata | 548/517 |
| 5,081,284 | 1/1992 | Higuchi | 560/159 |
| 5,118,606 | 6/1992 | Lynch | 435/7.1 |
| 5,135,956 | 8/1992 | Borg | 514/724 |

FOREIGN PATENT DOCUMENTS

| | | |
|---|---|---|
| 255980 | 2/1988 | European Pat. Off. . |
| 258203 | 3/1988 | European Pat. Off. . |
| 331803 | 9/1989 | European Pat. Off. . |
| 0364344 | 4/1990 | European Pat. Off. . |
| 393457 | 10/1990 | European Pat. Off. . |
| 395309 | 10/1990 | European Pat. Off. . |
| 131762 | 8/1982 | Japan . |
| 162586 | 9/1983 | Japan . |
| 53477 | 3/1984 | Japan . |
| 103897 | 5/1986 | Japan . |
| 104973 | 5/1988 | Japan . |
| 143836 | 6/1989 | Japan . |
| 223593 | 9/1989 | Japan . |
| 228495 | 9/1989 | Japan . |
| 161500 | 7/1991 | Japan . |
| 2127830 | 4/1984 | United Kingdom . |
| 8810266 | 6/1988 | WIPO . |

OTHER PUBLICATIONS

Wang K., Developing Selective Inhibitors of Calpain . . . Trends in Pharm Sciences vol. 11 Apr. 1990 pp. 139–142.

Hu L., Inhibition of Cathepsin B & Papain by . . . Arch Biochem & Biophys 281 (2) Sep. 1990 pp. 271–274.

Harper, J. W., Reaction of Serine Proteases . . . Biochemistry 1985 24 pp. 1831–1841.

(List continued on next page.)

*Primary Examiner*—William H. Beisner
*Assistant Examiner*—Ralph Gitomer
*Attorney, Agent, or Firm*—Knobbe Martens Olson & Bear

[57] ABSTRACT

The present invention provides a method of treating a neurodegenerative pathology in a human patient. This method includes selecting a patient for monitoring for the presence of a neurodegenerative pathology associated with enhanced Calpain activity and monitoring the patient for indicia of the onset or existence of such a pathology. In response to the detection of any such indicium of the presence or onset of the pathology, a therapeutically efficacious amount of a Peptide Ketoamide compound, or a pharmaceutically acceptable salt or derivative thereof, together with a pharmaceutically acceptable carrier is administered. The invention also provides additional methods of treatment and pharmaceutical compositions using Peptide Ketoamides, Peptide Ketoacids and Peptide Ketoesters.

35 Claims, 8 Drawing Sheets

OTHER PUBLICATIONS

Harper J. W. Reaction of Serine Proteases... Biochemistry 1985 24 pp. 7200–7213.
Khachaturian Z., Cacium, Membranes, Aging... Ann of N.Y. Acad 568 pp. 198–208 1989.
Arai, A., Calpain Inhibitors Improve the Recovery... Brain Research 532 #½pp. 63–68, 1990.
Angelastro M., α Diketone & α–Keto Ester Derivatives... J Med Chem 1990 33 11–13.
Barrett, et al., Methods Enzymol., 80:535–561 (1981).
Charles, et al., J. Chem. Soc., Perkin I, 1139–1146 (1980).
Davies and Poole, J. Chem. Soc., pp. 1616–1629 (1928).
Ferrell and Martin, J. Biol. Chem., 264:20723–20729 (1989).
Harper, et al., J. Am. Chem. Soc., 106:7618–7619 (1984).
IUPAC–IAB Joint Commission on Biochemical Nomenclature, J. Biol. Chem., 260:14–42 (1985).
Kam, et al., Biochem., 27:2547–2557 (1988).
Milevskaya, et al., Zhur. Org. Khim., 9:2145–2149 (1973).
Powers, et al., Biochem., 29:3108–3118 (1990).
Powers, Methods in Enzymology, 46:197–208 (1977).
Powers, in "Chemistry and Biochemistry of Amino Acids, Peptides and Proteins," vol. 4, Dekker, New York, pp. 65–178 (1977).
Rich, "Inhibitors of Cysteine Proteases in Protease Inhibitors", Barrett and Salversen, Eds., Elsevier, N.Y., 1986, pp. 153–178.
Sasaki, et al., J. Biol. Chem., 259:12489–12494 (1984).
Schechter, et al., Bioch. Biophys. Res. Commun., 27:157–162 (1967).
Seubert, et al., Neuroscience, 31:195 (1989).
Seubert, et al., Brain Res., 459:226–232 (1988).
Tian, et al., Biochem., 21:1028–1032 (1989).
Warren, et al., Chromatography, 64:219–222 (1972).
Yoshihara, et al., J. Biol. Chem., 265:5809–5815 (1990).
Peet et al., J. Med. Chem., 33:394–40 (1990) (p. 394 only).
Emori et al., J. Biol. Chem. 263:2364–2370 (1988).
Higuchi et al., Chemical Abstracts 111(19):174674y (1989) (from Japanese Patent Application No. 1–121257).
Maki et al., J. Biol. Chem. 264:18866–18869 (1989).
Mason, R. W., Bartholemew, L. T., and Hardwick, B. S., Biochem. J. 263:945–949, (1989).
Nixon et al., J. Neurochemistry 55:1950–1959 (1990).
Perlmutter et al., J. Comp. Neur. 296:269–276 (1990).
Sasaki, T, Kishi M, Saito M, Tanaka T, Higuchi N, Kominami E, Katunuma N, and Murachi T. J. Enzyme Inhibition 3:195–201 91990).
Siman et al., Brain Res. 347:399–403 (1985).
Arai, A., Kessler, M., Lee, K., and Lynch, G., Brain Research 530 (1) 1990, pp. 91–95.
Badalamente, M. A., Hurst, L. C., and Stracher, A., Proc. National Academy of Science, 86:5983–5987 (1989).
Croall, Chemical Abstracts 111(11):94444h (from Biochemistry 28:6882–6888 (1989).

del Cerro S, Larson J, Oliver M, and Lynch G., Brain Res. 530:91–95 (1990).
Inuzuka T, Tamura A, Sato S, Kirino T, Toyoshima I, and Miyatake T., Brain Res. 526, 177–179 (1990).
Inuzuka et al., Stroke, 21:917–922 (1990).
Ishii, H, Kuboki, M, Fujii, J, Hiraishi, S, and Kazama, Thrombosis Research 57:847–861 (1990).
Iwasaki, Y, Yamamoto H, Iizuka H, Yamamoto T, and Konno H., Brain Res. 406, 99–104 (1987).
Kuwaki, T., Satoh, H., Ono, T., Shibayama, F., Yamashita, T., Nishimura, T., Stroke, 20:78–83 (1989).
Masliah E, Limoto D. S., Saitoh T, Hansen L. A., and Terry R. D. Brain Res. 531:36–44 (1990).
McGowan E. B., Becker E, and Detwiler T. C., Biochem. Biophys. Res. Commun. 158, 432–435 (1989).
Mehdi S, Angelastro M. R., Wiseman J. S., and Bey P., Biochem. Biophys. Res. Commun. 157, 1117–11223 (1988).
Seubert et al., Brain Res. 460:189–194 (1988).
Siman, R, Noszek, J. C. and Kegerise, C, J. Neurosci. 9, 1579–1590 (1989).
Staubli et al., Brain Res. 444:153–158 (1988).
Zalewska et al., Biomed. Biochim. Acta 48:S166–S169 (1989).
El–Fawal et al., Toxicol. and Appl. Pharm. 103:133–142 (1990).
Gill et al., J. Neurosci 7:3343–3349 (1987).
Iizuka et al., J. Neurosurg. 65:92–98 (1986).
Lehmann, Neuropharm., 26:1751–1761 (1987).
Simon et al., Science 226:850–852 (1984).
Taylor et al., Brain Res. 347:268–273 (1985).
Toyo–oka et al., Drug Res. 36:671–675 (1986).
Fujiwara et al., J. Physiol 384:131–151 (1989).
Kamatsu et al. (Abstract from Exp. Neurol. 91:23–29 (1986).
Tamai et al. (Abstract from J. Pharmacobiodyn., 10:678–681 (1987).
Lee et al. manuscript, *Inhibition of Proteolysis Protects Hippocampal Neurons from Ischemia* No Date Avail.
Libby et al., Science 199:534–536 (1978).
Mehdi manuscript, *Cell–Penetrating Inhibitors of Calpain* No Date Avail.
Oliver et al., Brain Res. 505:233–238 (1989).
Mehdi et al. B.B.R.C. 166:595–600 (1990) (p. 595 only).
Banik et al., J. Neurosci. Res. 25:119–124 (1990).
Harris et al., Proc. Natl. Acad. Sci. 87:3009–3013 (1990).
Hori et al., Proc. of the Ninth American Peptide Symposium, Deber et al. eds., pp. 819–822 (1985).
Murachi et al., Biochemistry International, 18:263–294 (198tim
Parkes et al., Biochem. J., 230:509–516 (1985).
Chakrabarti et al., J. Neurochem. 54:1816–1819 (1990).
Inomata et al., J. Biochem., 98:407–416 (1985).
Siman et al., Proc. Natl. Acad. Sci., 81:3572–3576 (1984).
Sorimachi et al., J. Biol. Chem., 33:20106–20111 (1989).
Barraclough et al. Current CNS Patents, 1:2–27 (1990).
Crawford, C (1990), "Protein and peptide inhibitors of (List continued on next page.)

OTHER PUBLICATIONS

Mellgren and T Murachi, Eds., CRC Press. Melloni et al., TINS 12:438-444 (1989).

Suebert, P and Lynch, G (1990), in Intracellular calcium-dependent proteolysis, RL Mellgren and T Murachi, Eds., CRC Press, Boca Raton, Fla., pp. 251-276.

Choi, D W, Neuron 1:623-634 (1988).

Choi, D W, 3. Neurosci. 10, 2493-2501 (1990).

Lynch G, Larson J, and Baudry M, in Treatment development strategies for Alzheimer's disease, T Crook, R Bartus, S Ferris, and S Gershon, Eds., Mark Powley Assoc., Madison, Conn, USA pp. 119-150 (1986).

Siman et al., Neuron 1:279-287 (1988).

Wang, K. K. W., TiPS 11:139-142 (1990).

Siman et al., J. Neurosci. 10:2400-2411 (1990).

Yamashita, J. Osaka Univ. Med. School 39:101-108 (1987) (in Japanese).

Mayer et al., Med. Chem. 1991, 34, 3029-3035.

Neurobiology of Aging, volume 11, No. 4, 1990, Pergamon Press plc., (US) E. Nilsson et al.: "Calpain and, calpastatin in normal and Alzheimer-degenerated human brain tissue", pp. 425-431, see the whole article, especially Discussion.

Brain Research Contents, vol. 532, No. $\frac{1}{2}$, 5 Nov. 1990, Elsevier Science. Publishers B.V., A. Arai et al.: "Calpain inhibitors improve the recovery of synaptic transmission form hypoxia in hippocampal slices", pp. 63-68, see the entire article, especially results.

Brain Research Contents, vol. 530, No. 1, 15 Oct. 1990, Elsevier Science Publishers BV.; S. del Cerro et al.: "Development of hippocampal long-term potentiation is reduced by recently introduced calpain inhibitors", pp. 91-95.

Annals of the New York Academy of Sciences, volume 568 (New York, US) R. A. Nixon: "Calcium-activated neutral proteinases as regulators of cellular function", pp. 198-208, 1989.

METHOD OF TREATMENT OF NEURODEGENERATION WITH CALPAIN INHIBITORS

RELATED APPLICATIONS

This application is a continuation of Ser. No. 07/816,120, filed Dec. 27, 1991, now abandoned, which is a continuation-in-part of Ser. No. 07/682,925, filed Apr. 9, 1991, now abandoned, which is a continuation of Ser. No. 07/635,952, filed Dec. 28, 1990.

BACKGROUND OF THE INVENTION

The present invention relates generally to the field of neuroprotectants and more specifically to the use of inhibitors of calcium-stimulated proteases, such as calpain, as therapeutics for neurodegeneration.

Neural tissues, including brain, are known to possess a large variety of proteases, including at least two calcium-stimulated proteases, termed calpain I and calpain II, which are activated by micromolar and millimolar $Ca^{2+}$o concentrations, respectively. Calpains are a family of calcium activated thiol proteases that are present in many tissues. Calpain II is the predominant form, but calpain I is found at synapses and is thought to be the form involved in long term potentiation and synaptic plasticity.

Thiol proteases are distinguished from serine proteases, metalloproteases and other proteases by their mechanism of action and by the amino acid residue (cysteine) that participates in substrate attack. Although several thiol proteases are produced by plants, these proteases are not common in mammals, with cathepsin B (a lysosomal enzyme), other cathepsins and the calpains being among the few representatives of this family that have been described in mammals. Calpain I and calpain II are the best described of these, but several other members of the calpain family have been reported.

Other $Ca^{2+}$-activated thiol proteases may exist, such as those reported by Yoshihara et al. in J. Biol. Chem. 265:5809–5815 (1990). The term "Calpain" is used hereinafter to refer to any $Ca^{2+}$-activated thiol proteases including the Yoshihara enzyme and calpains I and II.

While Calpains degrade a wide variety of protein substrates, cytoskeletal proteins seem to be particularly susceptible to attack. In at least some cases, the products of the proteolytic digestion of these proteins by Calpain are distinctive and persistent over time. Since cytoskeletal proteins are major components of certain types of cells, this provides a simple method of detecting Calpain activity in cells and tissues. Specifically, the accumulation of the breakdown products ("BDP's") of spectrin, a cytoskeletal protein, has been associated with the activation of Calpain. In neural tissues, activation of Calpains, as evidenced by accumulation of these BDP's, has been observed in many neurodegenerative conditions, including denervation resulting from focal electrolytic lesions, genetic abnormalities, excitotoxicity, Alzheimer's disease, following ischemia in gerbils and following administration of the toxins kainate and colchicine in rats, when administered peripherally or centrally.

Commercially available in vitro inhibitors of Calpain include peptide aldehydes such as leupeptin (Ac-Leu-Leu-Arg-H), as well as epoxysuccinates such as E-64. These compounds are not useful in inhibiting Calpain in Central Nervous System ("CNS") tissue in vivo because they are poorly membrane permeant and, accordingly, do not cross the blood brain barrier very well. Also, many of these inhibitors are poorly specific and will inhibit a wide variety of proteases in addition to Calpain. These commercially available compounds are based upon peptide structures that are believed to interact with the substrate binding site of Calpain. Active groups associated with the Calpain inhibitors then either block or attack the catalytic moiety of Calpain in order to inhibit the enzyme.

In addition, other types of compounds thought to possess in vitro Calpain inhibitory activity that are not commercially available have been reported. Examples of such compounds include the peptide diazomethanes. See Rich, D. H., Inhibitors of cysteine proteinases, in Protease Inhibitors, A. J. Barrett and G. Salversen, Eds., Elsevier, New York, 1986, pp153–178, the disclosure of which is hereby incorporated by reference. These peptide diazomethanes are similarly thought to be poorly membrane permeant and non-specific.

There is some evidence that certain particular inhibitors of Calpain have certain therapeutic utilities. For example, leupeptin can facilitate nerve repair in primates. Loxastatin (also known as EST, Ep-460 or E-64d), a derivative of E-64, is believed to have utility in the treatment of muscular dystrophy. E-64d, while not having significant protease inhibitory activity itself, is believed to be converted to more potent forms, such as to E-64c, inside a mammalian body.

Evidence from electrophysiological studies suggests that one of the earliest factors in the chain of reactions leading to cell death is an increase in intracellular-free calcium as a consequence of $Ca^{2+}$ channel opening and/or energy depletion. Intracellular calcium is likely to produce a large number of consequences, including the activation of a large number of enzymes, including proteases, such as Calpain, lipases and kinases. An increase in intracellular calcium is also thought to induce changes in gene expression.

Ischemia, head trauma and stroke have all been associated with the release of glutamate in amounts large enough to lead to excitotoxicity, the toxicity resulting from the actions of certain amino acids on neurons of the CNS. The excess glutamate and other factors, such as free radical damage of membranes or energy depletion, cause an increase in intracellular $Ca^{2+}$. It is known that an excess of intracellular $Ca^{2+}$ leads to several effects believed to be associated with neuronal cell damage, including destruction of cell structures through activation of phospholipase and Calpain, as well as free radical production resulting from activation of phospholipase and xanthine oxidase. Many other factors have been associated with neurotoxicity. For example, reductions in action potentials and changes in a wide variety of chemical markers are known to be associated with neurons exposed to ischemic conditions.

Notwithstanding the foregoing understanding of certain aspects of neurotoxicity, no effective therapy has yet been developed for most neurodegenerative diseases and conditions of the CNS. Millions of individuals suffer from these diseases and conditions. Thus, there is a need for therapies effective in treating and preventing these diseases and conditions.

SUMMARY OF THE INVENTION

One aspect of the present invention provides a method of treating a neurodegenerative pathology in a human patient. This method includes the steps of selecting a patient for monitoring for the presence of a neurodegenerative pathology having enhanced Calpain activity associated therewith, monitoring the patient for indicia of the onset or existence of a neurodegenerative pathology having enhanced Calpain activity associated therewith, and in response to the detection of any such indicium of the presence or onset of neurodegeneration of the type associated with enhanced calpain activity, administering a therapeutically efficacious amount of a Peptide Ketoamide compound, or a pharmaceutically acceptable salt or derivative thereof, together with a pharmaceutically acceptable carrier. The selecting step can comprise selecting a patient in which neurodegeneration is occuring or is likely to occur, and the administering step can comprise administering one of the following classes of compounds: Dipeptide α-Ketoamides (Subclass A), Dipeptide α-Ketoamides (Subclass B), Tripeptide α-Ketoamides, Tetrapeptide α-Ketoamides and Amino Acid α-Ketoamides.

Another aspect of the present invention provides a method of inhibiting or treating neurodegeneration in a mammal having or likely to experience a neuropathology. This method includes the administration to the mammal of a therapeutically efficacious amount of Peptide Ketoamide compound that has Calpain inhibitory activity or a pharmaceutically acceptable salt or derivative thereof. This Peptide Ketoamide compound is preferably from one of the following classes: Dipeptide α-Ketoamides (Subclass A), Dipeptide α-Ketoamides (Subclass B), Tripeptide α-Ketoamides, Tetrapeptide α-Ketoamides and Amino Acid α-Ketoamides. The method can also include identifying, prior to administration of the compound with Calpain inhibitory activity, a mammal in which neurodegeneration of the CNS is occurring or is likely to occur. The method is useful where the neurodegeneration is associated with a condition selected from the group consisting of excitotoxicity, HIV-induced neuropathy, ischemia, subarachnoid hemorrhage, stroke, brain seizure, major heart attack, multiple infarction dementia, Alzheimer's Disease, Huntington's Disease, surgery-related brain damage and Parkinson's Disease. The administering step of this method can be any of a variety of adminstering procedures known to those of ordinary skill in the art, such as parenteral administration of a Calpain Inhibitor in a pharmaceutically acceptable carrier or oral administration of a Calpain Inhibitor in a form suitable for oral use. Parenteral administration is preferably by transdermal administration, subcutaneous injection, intravenous, intramuscular or intrasternal injection, intrathecal injection directly into the CNS or infusion techniques.

Still another aspect of the present invention provides methods of intervening early in the process of neurodegeneration occurring in neural tissue of a mammal using an active ingredient which protects and assists in recovery of neural tissue, comprising administering a pharmaceutically acceptable form of the active ingredient to the mammal. The active ingredient can be a Peptide α-Ketoacid such as Bz-DL-Lys-COOH, Bz-DL-Ala-COOH, Z-Leu-Phe-COOH or Z-Leu-Abu-COOH. The active ingredient can also be an Amino Acid Peptide α-Ketoester, such as Bz-DL-Ala-COOEt, Bz-DL-Ala-COOBzl, Bz-DL-Ala-COOnBu, Bz-DL-Phe-COOEt, Bz-DL-Ala-COOCH2—C6H4—CF3 (para), Bz-DL-Arg-COOEt, Bz-DL-Lys-COOEt, PhCO-Abu-COOEt, $(CH_3)_2CH(CH_2)_2CO$-Abu-COOEt, $CH_3CH_2CH)_2CHCO$-Abu-COOEt or $Ph(CH_2)_6CO$-Abu-COOEt. Another useful active ingredient would be a Dipeptide α-Ketoester such as Z-Ala-DL-Ala-COOEt, Z-Ala-DL-Ala-COOBzl, Z-Ala-DL-Ala-COOnBu, Z-Leu-Nva-COOEt, Z-Leu-Nle-COOEt, Z-Leu-Phe-COOEt, Z-Leu-Abu-COOEt, Z-Leu-Met-COOEt, Z-Phe-DL-Phe-COOEt, H-Gly-DL-Lys-COOEt, H-Ala-DL-Lys-COOEt, H-Pro-DL-Lys-COOEt, H-Phe-DL-Lys-COOEt, Z-Leu-Phe-COOEt, Z-Leu-4-Cl-Phe-COOEt, 2-NapSO2-Leu-Abu-COOEt, Z-Leu-NLeu-CO2Et, Z-Leu-Phe-CO2Bu, Z-Leu-Abu-CO2Bu, Z-Leu-Phe-CO2Bzl, MeO-Suc-Ala-DL-Ala-COOMe, or Z-Leu-Abu-CO2Bzl. Still another active ingredient could be a Tripeptide α-Ketoester such as Z-Ala-Ala-DL-Ala-COOEt, Z-Ala-Pro-DL-Ala-COOEt, Z-Ala-Ala-DL-Abu-COOEt, Z-Ala-Ala-DL-Abu-COOBzl, Z-Ala-Ala-DL-Abu-COOCH2—C6H4—CF3 (para), H-Leu-Ala-DL-Lys-COOEt, Z-Leu-Leu-Abu-COOEt, Z-Leu-Leu-Phe-COOEt, MeO-Suc-Val-Pro-DL-Phe-COOMe or 2-NapSO2-Leu-Leu-Abu-COOEt. A Tetrapeptide α-Ketoester, such as MeO-Suc-Ala-Ala-Pro-DL-Abu-COOMe or Z-Ala-Ala-Ala-DL-Ala-COOEt, could also be the active ingredient. Still another type of active ingredient would be a Peptide α-Ketoamide such as Z-Leu-Phe-CONH-Et, Z-Leu-Phe-CONH-nPr, Z-Leu-Phe-CONH-nBu, Z-Leu-Phe-CONH-iBu, Z-Leu-Phe-CONH-Bzl, Z-Leu-Phe-CONH—(CH2)2Ph, Z-Leu-Abu-CONH-Et, Z-Leu-Abu-CONH-nPr, Z-Leu-Abu-CONH-nBu, Z-Leu-Abu-CONH-iBu, Z-Leu-Abu-CONH-Bzl, Z-Leu-Abu-CONH—(CH2)2Ph, Z-Leu-Abu-CONH—(CH2)3—N(CH2CH2)2O, Z-Leu-Abu-CONH—(CH2)7CH3, Z-Leu-Abu-CONH—(CH2)2OH, Z-Leu-Abu-CONH—(CH2)2O(CH2)2OH, Z-Leu-Abu-CONH—(CH2)17CH3, Z-Leu-Abu-CONH—CH2—C6H3(OCH3)2 or Z-Leu-Abu-CONH—CH2—C4H4N.

In yet another aspect of the present invention, there is provided a method of minimizing proteolysis in a biological sample containing peptides or proteins, during the processing, production, isolation, purification, storage or transport of the samples. This method includes the addition to the sample of a Peptide α-Ketoacid compound having Calpain activity or a form thereof having Calpain inhibitory activity. Preferred compounds in this method include Bz-DL-Lys-COOH, Bz-DL-Ala-COOH, Z-Leu-Phe-COOH and Z-Leu-Abu-COOH. Example of biological samples which can be used in this method include an in vitro sample, a tissue sample or a whole organ.

The present invention also provides pharmaceutical compositions for the treatment or inhibition of neurodegeneration comprising a pharmacologically effective neuroprotective amount of a Peptide Ketoamide or a pharmaceutically acceptable salt or derivative thereof in a pharmaceutically acceptable formulation containing a carrier material. The Peptide Ketoamide preferably comprises a compound from the following subclasses: Dipeptide α-Ketoamides (Subclass A), Dipeptide α-Ketoamides (Subclass B), Tripeptide α-Ketoamides, Tetrapeptide α-Ketoamides and Amino Acid α-Ketoamides. Particular Peptide Ketoamide compounds which are believed effective include Z-Leu-Phe-CONH-Et, Z-Leu-Phe-CONH-nPr, Z-Leu-Phe-CONH-nBu, Z-Leu-Phe-CONH-iBu, Z-Leu-Phe-CONH-Bzl, Z-Leu-Phe-CONH—(CH2)2Ph, Z-Leu-Abu-CONH-Et, Z-Leu-Abu-CONH-nPr, Z-Leu-Abu-CONH-nBu, Z-Leu-Abu-CONH-iBu, Z-Leu-Abu-CONH-Bzl, Z-Leu-Abu-CONH—(CH2)2Ph, Z-Leu-Abu-CONH—(CH2)3—N(CH2CH2)2O, Z-Leu-Abu-CONH—(CH2)7CH3, Z-Leu-Abu-CONH—(CH2)2OH, Z-Leu-Abu-CONH—(CH$_2$)$_2$O(CH$_2$)$_2$OH, Z-Leu-Abu-CONH—(CH$_2$)$_{17}$CH$_3$, Z-Leu-Abu-CONH—CH$_2$—C$_6$H$_3$(OCH$_3$)$_2$ and Z-Leu-Abu-CONH—CH$_2$—C$_4$H$_4$N. Additional pharmaceutical compositions for the treatment or inhibition of neurodegeneration are also provided by the present invention. These compositions include a pharmacologically effective neuroprotective amount of an active ingredient or a pharmaceutically acceptable salt or derivative thereof in a pharmaceutically acceptable formulation containing a carrier material. In these compositions the active ingredient can be an Amino Acid Peptide Ketoester compound such as Bz-DL-Ala-COOEt, Bz-DL-Ala-COOCH$_2$—C$_6$H$_4$—CF$_3$ (para), Bz-DL-Lys-COOEt, PhCO-Abu-COOEt, (CH$_3$)$_2$CH(CH$_2$)$_2$CO-Abu-COOEt, CH$_3$CH$_2$CH)$_2$CHCO-Abu-COOEt or Ph(CH$_2$)$_6$CO-Abu-COOEt. Another active ingredient would be a Dipeptide Ketoester compound such as Z-Ala-DL-Ala-COOEt, Z-Ala-DL-Ala-COOBzl, Z-Ala-DL-Ala-COOnBu, Z-Leu-Nva-COOEt, Z-Leu-Nle-COOEt, Z-Leu-Abu-COOEt, Z-Leu-Met-COOEt, Z-Leu-Phe-COOEt, Z-Leu-4-Cl-Phe-COOEt, 2-NapSO2-Leu-Abu-COOEt, Z-Leu-NLeu-CO$_2$Et, Z-Leu-Phe-CO$_2$Bu, Z-Leu-Abu-CO$_2$Bu, Z-Leu-Phe-CO$_2$Bzl, MeO-Suc-Ala-DL-Ala-COOMe or Z-Leu-Abu-CO$_2$Bzl. Still another active ingredient would be a Tripeptide Ketoester compound such as Z-Ala-Ala-DL-Ala-COOEt, Z-Ala-Pro-DL-Ala-COOEt, Z-Ala-Ala-DL-Abu-COOEt, Z-Ala-Ala-DL-Abu-COOBzl, Z-Ala-Ala-DL-Abu-COOCH2—C$_6$H$_4$—CF$_3$ (para), H-Leu-Ala-DL-Lys-COOEt, Z-Leu-Leu-Abu-COOEt, Z-Leu-Leu-Phe-COOEt, MeO-Suc-Val-Pro-DL-Phe-COOMe or 2-NapSO$_2$-Leu-Leu-Abu-COOEt. A Tetrapeptide Ketoester, such as Z-Ala-Ala-Ala-DL-Ala-COOEt or MeO-Suc-Ala-Ala-Pro-DL-Abu-COOMe, could also be the active ingredient. In addition, a Peptide Ketoacid, such as Bz-DL-Lys-COOH, Bz-DL-Ala-COOH, Z-Leu-Phe-COOH and Z-Leu-Abu-COOH could be the active ingredient.

These and other features and advantages of the present invention will become apparent from the detailed description of preferred embodiments which follows, when considered together with the attached drawings and claims.

DETAILED DESCRIPTION OF THE INVENTION

A. INTRODUCTION

Figure 1:
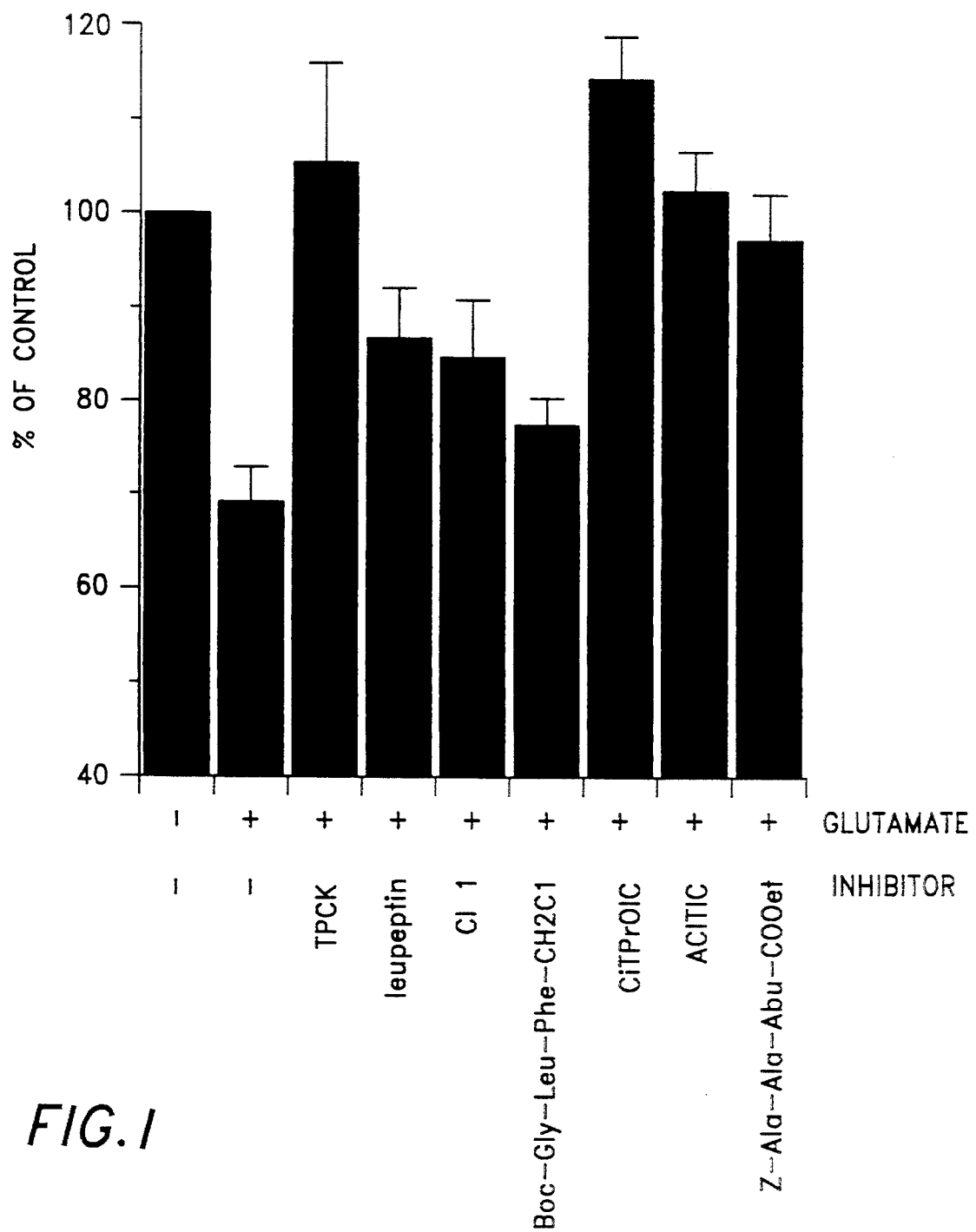
FIG. 1 shows the percentage of inhibition of glutamate-induced cell death through the addition of glutamate and various Calpain Inhibitors relative to control where no glutamate was added.

We have discovered that Calpain activation is an event central to many cases of brain atrophy and degeneration and that inhibition of Calpain alone is sufficient to inhibit or prevent cell deterioration and loss. Thus, we have further discovered that inhibition of Calpain provides protection from neurotoxicity associated with many neurodegenerative conditions and diseases.

In accordance with the foregoing discoveries, we believe that the elevation of intracellular calcium associated with neuropathological conditions in neuronal cells activates Calpain and sets in motion the digestion of neuronal cells from within. We believe there may be other mechanisms of activation of Calpains associated with these conditions. Accordingly, one aspect of the present invention is directed to inhibition and treatment of the neurodegeneration and other diseases associated with this digestion through the inhibition of Calpain activity. Thus, part of this aspect of the present invention is to prevent the neurodegeneration and other pathology caused by this digestion through the in vivo administration of Calpain inhibitors. By way of example, and not of limitation, diseases and conditions which can be treated using this aspect of the present invention include neurodegeneration following excitotoxicity, HIV-induced neuropathy, ischemia, denervation following ischemia or injury, subarachnoid hemorrhage, stroke, multiple infarction dementia, Alzheimer's Disease (AD), Parkinson's Disease, Huntington's Disease, surgery-related brain damage and other neuropathological conditions.

As stated above, spectrin BDP's have been found to be associated with Calpain activation in vivo. We have observed that in each instance of neurodegeneration in which BDP's characteristic of Calpain activation are detected, Calpain activation is localized to the brain areas most vulnerable to the particular pathogenic manipulation. In addition, as judged by histological methods, Calpain activation precedes overt evidence of neurodegeneration. Accordingly, Calpain activation is spatially and temporally linked to impending or ongoing cell death in the brain. Thus, we believe that Calpain activation is an important mechanism of cell damage and death in many pathological conditions, including neuropathological conditions. Moreover, there is evidence that the activation of Calpains is an early event in the death of cells including neural cells. This is in contrast to other known proteases which are activated at later stages of cell death. Thus, we believe that, advantageously, inhibition of Calpain activity provides intervention at an early stage of cell death, prior to significant deterioration of cellular machinery.

Another aspect of the involvement of Calpains in neurodegeneration is the involvement of these proteins in regenerating systems. It is known that developing or regenerating axons are somehow inhibited from further development in a stabilization process called the "stop pathway." This stabilization can occur when axons have reached their targets; however, in some systems stabilization can also occur at inappropriate places. One researcher has developed evidence that this stop pathway operates at least in part by the activation of intracellular Calpain and that inhibition of Calpain can interfere with stabilization (Luizzi, 1990). We believe that Calpain inhibitors, when used in accordance with the present invention, can advantageously aid regeneration and recovery of neural tissue after injury, in addition to inhibiting neurodegeneration.

Another aspect of the present invention is our discovery that at least three classes of compounds, the substituted isocoumarins, the peptide keto-compounds and the Halo-Ketone Peptides have Calpain inhibitory activity. We have further discovered, as will be described hereinbelow, that these three classes of compounds exhibit additional properties that render them especially useful as therapeutically effective compounds in the treatment of neurodegenerative conditions and diseases.

B. SUBSTITUTED HETEROCYCLIC COMPOUNDS

One particular class of compounds exhibiting Calpain inhibitory activity, when used in accordance with the present invention, are the substituted heterocyclic compounds. These compounds include the substituted isocoumarins. The substituted heterocyclic compounds are known to be excellent inhibitors of serine proteases. As discussed hereinbelow, we have now discovered that these compounds are also inhibitors of calpain I and calpain II, and also of other Calpains. Additionally, as also discussed below, we have found that, unlike most known inhibitors of Calpains, these substituted heterocyclic compounds are not effective as inhibitors of papain or cathepsin B. Thus, we believe that the substituted heterocyclic compounds provide a relatively specific means of inhibiting Calpains while not affecting other thiol proteases.

One particular class of substituted heterocyclic compounds with Calpain inhibitory activity are the isocoumarins having cationic substituents. These substituted heterocyclic compounds are referred to herein as the "Class I Substituted Isocoumarins." The Class I Substituted Isocoumarins are known to be excellent inhibitors of several serine proteases, including bovine thrombin, human thrombin, human factor Xa, human factor XIa, human factor XIIa, bovine trypsin, human plasma plasmin, human tissue plasminogen activator, human lung tryptase, rat skin tryptase, human leukocyte elastase, porcine pancreatic elastase, bovine chymotrypsin and human leukocyte cathepsin G. The Class I Substituted Isocoumarins inhibit the serine proteases by reaction with the active site serine to form an acyl enzyme, which in some cases may further react with another active site nucleophile to form an additional covalent bond. We have discovered that the Class I Substituted Isocoumarins also react with Calpain. We believe that the mechanism of action of Calpain inhibition is similar to that of the inhibition of serine proteases since the reaction mechanism of Calpains is similar to that of the serine proteases.

The Class I Substituted Isocoumarins having Calpain inhibitory activity have the following structural formula:

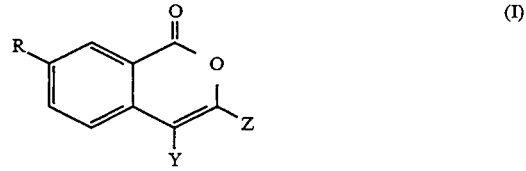

or a pharmaceutically acceptable salt, wherein

Z is selected from the group consisting of C1-6 alkoxy with an amino group attached to the alkoxy group, C1-6 alkoxy with an isothiureido group attached to the alkoxy group, C1-6 alkoxy with a guanidino group attached to the alkoxy group, C1-6 alkoxy with an amidino group attached to the alkoxy group, C1-6 alkyl with an amino group attached to the alkyl group, C1-6 alkyl with an isothiureido group attached to the alkyl group, C1-6 alkyl with an guanidino group attached to the alkyl group, C1-6 alkyl with an amidino group attached to the alkyl group, R is selected from the group consisting of O=C-=N—, S=C=N—, AA-NH—, AA-AA-NH—, AA-O, AA-AA-O—, M-NH—, M-AA-NH, M-AA-AA-NH—, M—O—, M-AA-O—, M-AA-AA-O— wherein AA represents alanine, valine, leucine, isoleucine, proline, methionine, phenylalanine, tryptophan, glycine, serine, threonine, cysteine, tyrosine, beta-alanine, norleucine, norvaline, alpha-aminobutyric acid, epsilon-aminocaproic acid, citrulline, hydroxyproline, ornithine or sarcosine, wherein M represents NH2—CO—, NH2—CS—, NH2—SO2—, X—NH—CO—, X—NH—CS, X—NH—SO2, X—CO—, X—CS—, X—SO2—, X—O—CO—, or X—O—CS—, wherein X represents C1-6 alkyl, C1-6 fluoroalkyl, C1-6 alkyl substituted with K, C1-6 fluoroalkyl substituted with K, phenyl, phenyl substituted with J, phenyl disubstituted with J, phenyl trisubstituted with J, naphthyl, naphthyl substituted with J, naphthyl disubstituted with J, naphthyl trisubstituted with J, C1-6 alkyl with an attached phenyl group, C1-6 alkyl with two attached phenyl groups, C1-6 alkyl with an attached phenyl group substituted with J, or C1-6 alkyl with two attached phenyl groups substituted with J, wherein J represents halogen, COOH, OH, CN, NO2, C1-6 alkyl, C1-6 alkoxy, C1-6 alkylamine, C1-6 dialkylamine, or C1-6 alkyl-O—CO—, wherein K represents halogen, COOH, OH, CN, NO2, NH2, C1-6 alkylamine, C1-6 dialkylamine, or C1-6 alkyl-O—CO—, Y is selected from the group consisting of H, halogen, trifluoromethyl, methyl, OH and methoxy.

The compounds of Formula (I) can also contain one or more substituents at position B as shown in the following structure:

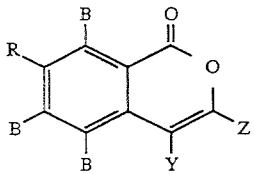

wherein electronegative substituents such as NO2, CN, Cl, COOR, and COOH will increase the reactivity of the isocoumarin, and electropositive substituents such as NH2, OH, alkoxy, thioalkyl, alkyl, alkylamino, and dialkylamino will increase its stability. Neutral substituents could also increase the stability of acyl enzyme and improve the effectiveness of the inhibitors.

The following compounds are representative of the Class I Substituted Isocoumarins of the present invention:

4-chloro-3-(3-isothiureidopropoxy)isocoumarin (CiTPrOIC)

7-(benzylcarbamoylamino)-4-chloro-3-(3-isothiureidopropoxy)isocoumarin (PhCH2NHCONH-CiTPrOIC)

7-(phenylcarbamoylamino)-4-chloro-3-(3-isothiureidopropoxy)isocoumarin (PhNHCONH-CiTPrOIC)

7-(acetylamino)-4-chloro-3-(3-isothiureidopropoxy)isocoumarin (CH3CONH-CiTPrOIC)

7-(3-phenylpropionylamino)-4-chloro-3-(3-isothiureidopropoxy)isocoumarin (PhCH2CH2CONH-CiTPrOIC)

7-(phenylacetylamino)-4-chloro-3-(3-isothiureidopropoxy)isocoumarin (PhCH2CONH-CiTRrOIC)

7-(L-phenylalanylamino)-4-chloro-3-(3-isothiureidopropoxy)isocoumarin (L-Phe-NH-CiTPrOIC)

7-(N-t-butyloxycarbonyl-L-phenylalanylamino)-4-chloro-3-(3-isothiureidopropoxy)isocoumarin (Boc-L-Phe-NH-CiTRrOIC)

7-(D-phenylalanylamino)-4-chloro-3-(3-isothiureidopropoxy)isocoumarin (D-Phe-NH-CiTPrOIC)

7-(N-t-butyloxycarbonyl-D-phenylalanylamino)-4-chloro-3-(3-isothiureidopropoxy)isocoumarin (Boc-D-Phe-NH-CiTPrOIC)

7-(benzylcarbamoylamino)-4-chloro-3-(2-isothiureidoethoxy)isocoumarin (PhCH2NHCONH-CiTEtOIC)

7-(phenylcarbamoylamino)-4-chloro-3-(2-isothiureidoethoxy)isocoumarin (PhNHCONH-CiTEtOIC)

7-(isopropylcarbamoylamino)-4-chloro-3-(2-isothiureidoethoxy)isocoumarin ((CH3)2CHNHCONH-CiTEtOIC)

7-(phenylacetylamino)-4-chloro-3-(2-isothiureidoethoxy)isocoumarin (PhCH2CONH-CiTEtOIC)

7-(L-phenylalanylamino)-4-chloro-3-(2-isothiureidoethoxy)isocoumarin (L-Phe-NH-CiTEtOIC)

7-(N-t-butyloxycarbonyl-L-phenylalanylamino)-4-chloro-3-(2-isothiureidoethoxy)isocoumarin (Boc-L-Phe-NH-CiTEtOIC)

7-(D-phenylalanylamino)-4-chloro-3-(2-isothiureidoethoxy)isocoumarin (D-Phe-NH-CiTEtOIC)

7-(N-t-butyloxycarbonyl-D-phenylalanylamino)-4-chloro-3-(2-isothiureidoethoxy)isocoumarin (Boc-D-Phe-NH-CiTEtOIC)

7-(N-t-butyloxycarbonyl-L-alanyl-L-alanylamino)-4-chloro-3-(2-isothiureidoethoxy)isocoumarin (Boc-Ala-Ala-NH-CiTEtOIC)

7-(L-alanyl-L-alanylamino)-4-chloro-3-(2-isothiureidoethoxy)isocoumarin (ala-Ala-NH-CiTEtOIC)

7-(1-naphthylcarbamoylamino)-4-chloro-3-(2-isothiureidoethoxy)isocoumarin (NaphthylNH-CiTEtOIC)

7-((S)-α-methylbenzylcarbamoylamino)-4-chloro-3-(2-isothiureidoethoxy)isocoumarin (S-C6H5(CH3)CHNHCONH-CiTEtOIC)

7-((R)-α-methylbenzylcarbamoylamino)-4-chloro-3-(2-isothiureidoethoxy)isocoumarin (R-C6H5(CH3)CHNHCONH-CiTEtOIC)

7-dansylamino-4-chloro-3-(2-isothiureidoethoxy)isocoumarin (DansylNH-CiTEtOIC)

7-phenylthiocarbamoylamino-4-chloro-3-(2-isothiureidoethoxy)isocoumarin (PhNHCSNH-CiTEtOIC)

7-(m-carboxyphenylthiocarbamoyl)amino-4-chloro-3-(2-isothiureidoethoxy)isocoumarin (m-COOH-PhNHCSNH-CiTEtOIC)

7-(p-carboxyphenylthiocarbamoyl)amino-4-chloro-3-(2-isothiureidoethoxy)isocoumarin (p-COOH-PhNHCSNH-CiTEtOIC)

7-amino-4-chloro-3-(3-isothiureidopropoxy)isocoumarin (ACITIC)

Isocoumarins with basic substituents are also known to be effective inhibitors of serine proteases. See Powers et al, U.S. Pat. No. 4,845,242, the disclosure of which is hereby incorporated by reference. This class of compounds, referred to herein as the "Class II Substituted Isocoumarins," along with the other substituted heterocyclic compounds, is believed to be effective in the use of the present invention.

The Class II Substituted Isocoumarins have the following structural formula:

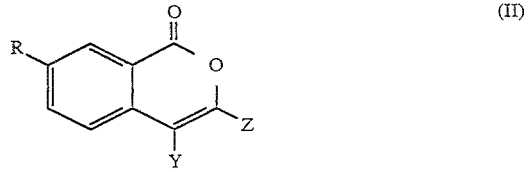

(II)

or a pharmaceutically acceptable salt, wherein

R is selected from the group consisting of —N—H—C(=NH)—NH2, —C(=NH)NH2, $C_{1-6}$ alkyl with an attached amino, and $C_{1-6}$ alkyl with an attached isothiureido of the formula —S—C(+NH2+)NH2, Z is selected from the group consisting of H, halogen, $C_{1-6}$ alkyl, $C_{1-6}$ alkyl with an attached phenyl, $C_{1-6}$ fluorinated alkyl, $C_{1-6}$ alkyl with an attached hydroxyl, $C_{1-6}$ alkyl with an attached $C_{1-6}$ alkoxy, $C_{1-6}$ alkoxy, $C_{1-6}$ fluorinated alkoxy, $C_{1-6}$ alkoxy with an attached phenyl, benzyloxy, 4-fluorobenzyloxy, —OCH2C6H4R' (2-substituent), —OCH2C6H4R' (3-substituent), —OCH2C6H4R' (4-substituent), —OCH2C6H3R2' (2,3-substituents), —OCH2C6H3R2' (2,4-substituents), —OCH2C6H3R2' (2,5-substituents), —OCH2C6H3R2' (2,6-substituents), —OCH2C6H3R2' (3,4-substituents), and OCH2C6H3R2' (3,5-substituents).

R' is selected from the group consisting of H, halogen, trifluoromethyl, NO2, cyano, methyl, methoxy, acetyl, carboxyl, OH, and amino.

Y is selected from the group consisting of H, halogen, trifluoromethyl, methyl, OH, and methoxy.

Alternately, the Class II Substituted Isocoumarins are represented by structure (II) where, Z is selected from the group consisting of $C_{1-6}$ alkoxy with an attached isothiureido, $C_{1-6}$ alkoxy with an attached guanidino, $C_{1-6}$ alkoxy with an attached amidino, $C_{1-6}$ alkyl with an attached amino, $C_{1-6}$ alkyl with an attached isothiureido, $C_{1-6}$ alkyl with an attached guanidino, $C_{1-6}$ alkyl with an attached amidino, R is selected from the group consisting of H, OH, $NH_2$, $NO_2$ halogen, $C_{1-6}$ alkoxy, $C_{1-6}$ fluorinated alkoxy, $C_{1-6}$ alkyl, $C_{1-6}$ alkyl with an attached amino, M-AA-NH—, M-AA-O—, wherein AA represents alanine, valine, leucine, isoleucine, proline, methionine, phenylalanine, tryptophan, glycine, serine, threonine, cysteine, tyrosine, asparagine, glutamine, aspartic acid, glutamic acid, lysine, arginine, histidine, beta-alanine, norleucine, norvaline, alpha-aminobutyric and epsilon-aminocaponic acid, citrulline, hydroxyproline, ornithine and sarcosine, wherein M represents H, lower alkanoyl having 1 to 6 carbons, carboxyalkanoyl, hydroxyalkanoyl, amin-alkanoyl, benzene sulfonyl, tosyl, benzoyl, and lower alkyl sulfonyl having 1 to 6 carbons, Y is selected from the group consisting of H, halogen, trifluoromethyl, methyl, OH and methoxy.

As a further alternative, the Class II Substituted Isocoumarins are represented by structure (II) where R is selected from the group consisting of —N—H—C(=NH)—$NH_2$, —C(=NH)$NH_2$, $C_{1-6}$ alkyl with an attached amino, $C_{1-6}$ alkyl with an attached isothiureido, Z is selected from the group consisting of $C_{1-6}$ alkoxy with an attached amino, $C_{1-6}$ alkoxy with an attached isothiureido, $C_{1-6}$ alkoxy with an attached guanidino, $C_{1-6}$ alkoxy with an attached amidino, $C_{1-6}$ alkyl with an attached amino, $C_{1-6}$ alkyl with an attached isothiureido, $C_{1-6}$ alkyl with an attached guanidino, $C_{1-6}$ alkyl with an attached amidino, Y is selected from the group consisting of H, halogen, trifluoromethyl, methyl, OH and methoxy.

The following compounds are representative of the Class II Substituted Isocoumarins:

3-(3-aminopropoxy)isocoumarin,
3-(3-aminopropoxy)-4-chloroisocoumarin,
3-(2-isothiureidoethoxy)-4-chloroisocoumarin,
3-(3-isothiureidopropoxy)-4-chloroisocoumarin,
7-amino-3-(3-isothiureidopropoxy)-4-chloroisocoumarin,
7-guanidino-3-methoxyisocoumarin,
7-guanidino-3-methoxy-4-chloroisocoumarin,
7-guanidino-3-ethoxyisocoumarin,
7-guanidino-3-ethoxy-4-chloroisocoumarin,
7-guanidino-3-(2-phenylethoxy)isocoumarin,
7-guanidino-3-(2-phenylethoxy)-4-chloroisocoumarin.

Still another class of susbstituted heterocyclic compounds useful in the present invention is referred to herein as the "Class III Heterocyclic Compounds" and have the following structural formula:

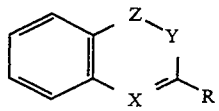

wherein

Z is selected from the group consisting of CO, SO, $SO_2$, CCl and CF,

Y is selected from the group consisting of O, S and NH,

X is selected from the group consisting of N and CH, and

R is selected from the group consisting of $C_{1-6}$ alkyl (such as methyl, ethyl and propyl), $C_{1-4}$ alkyl containing a phenyl (such as benzyl), and $C_{1-6}$ fluoroalkyl (such as trifluoromethyl, pentafluoroethyl, and heptafluoropropyl).

The Z group must be electrophilic since it interacts with the active site serine OH group of the serine protease. The R group must be uncharged and hydrophobic. One or more of the carbons in the R group could be replaced by O, S, NH and other such atomic groups as long as the R group maintains its hydrophobic character.

The following compounds are representative of the Class III Heterocyclic Compounds:

2-trifluoromethyl-4H-3,1-benzoxazine-4-one,
2-pentafluoroethyl-4H-3,1-benzoxazine-4-one,
2-heptafluoropropyl-4H-3,1-benzoxazine-4-one,
2-methyl-4H-3,1-benzoaxazine-4-one,
2-propyl-4H-3,1-benzoaxazine-4-one,
2-benzyl-4H-3,1-benxoaxazine-4-one,
2-heptafluoropropyl-4-quinazolinone,
2-propyl-4-quinazolinone,
2-benzyl-4-quinazolinone,
2-($C_6H_5CCl_2$)-4-chloroquinazoline, and
2-propyl-4-chloroquinazoline.

The Class III Heterocyclic Compounds are disclosed in Powers et al., U.S. Pat. No. 4,847,202, the disclosure of which is hereby incorporated by reference.

Other substituted heterocyclic compounds have been prepared earlier for other purposes, such as 3-chloroisocoumarin, Davies and Poole, J. Chem. Soc., pp. 1616–1629 (1928); 3-chloro and 3,4-dichloroisocoumarin, Milevskaya, Belinskaya, and Yagupol'skii, Zhur. Org. Khim. 9, pp. 2145–2149 (1973); 3-methyl and 4-carboxy-3-methylisocoumarin, Tirodkar and Usgaonkar, Ind. J. Chem. 7, pp. 1114–1116 (1969); 7-nitro and 7-aminoisocoumarin, Choksey and Usgaonkar, Ind. J. Chem. 14B, pp. 596–598 (1976). The disclosures of all of the preceding articles are hereby incorporated by reference. These other substituted isocoumarins are also believed to exhibit Calpain inhibitory activity when used in accordance with the present invention.

Still other substituted isocoumarins which have been prepared recently for inhibition of serine proteases are 3-chloroisocoumarin, Harper, Hemmi, and Powers, J. A. Chem. Soc. 105, pp. 6518–6520 (1983); 3,4-dichloroisocoumarin, Harper, Hemmi, and Powers, Biochemistry 24, pp. 1831–1841 (1985); 3-alkoxy-7-amino-4-chloroisocoumarin, Harper and Powers, J. Am. Chem. Soc. 106, pp. 7618–7619 (1984), Harper and Powers, Biochemistry 24, 7200–7213 (1983); additional substituted isocoumarins with basic groups (aminoalkoxy, guanidino or isothiureidoalkoxy), Kam, Fujikawa and Powers, Biochemistry 27, pp. 2547–2557 (1988); 7-substituted 3-alkoxy-4-chloroisocoumarins, Powers, Kam, Narasimhan, Oleksyszyn, Hernandez and Ueda, J. Cell Biochem. 39, pp. 33–46 (1989) and Powers, Oleksyszyn, Narasimhan, Kam, Radhakrishnan and Meyer, Jr. Biochemistry 29, 3108–3118 (1990). The disclosures of all of the preceding articles are hereby incorporated by reference. We believe that the foregoing compounds, which exhibit serine protease inhibitory activity, also exhibit Calpain inhibitory activity when used in accordance with the present invention. All of the foregoing isocoumarin compounds, including the Class I and II Substituted Isocoumarins, the Class III Substituted Heterocyclic Compounds and the other substituted heterocyclic compounds useful in the practice of the present invention shall be referred to collectively hereinafter as the "Substituted Heterocyclic Compounds." The term "Substituted Heterocyclic Compound" shall be used to refer to any particular species of these compounds.

The preparation of the various Substituted Heterocyclic Compounds is illustrated by Examples SHC1-SHC9.

EXAMPLE SHC1

Preparation of 7-(phenylcarbamoylamino)-4-chloroisocoumarin was synthesized as previously described (Powers, et al., Biochemistry 29, 3108–3118 (1990)). This compound (0.32 g, 1 mmole) was mixed with phenyl isocyanate (0.12 g, 1 mmole) in 5 ml of THF and the reaction mixture was stirred at r.t. overnight. The product 7-(phenylcarbamoylamino)-4-chloro-3-(2-bromoethoxy)isocoumarin precipitated out, yield 40%, m.p. 215°–217° C., mass spectrum m/e=437.9 (M+)> Anal. Calc. for $C_{18}H_{14}N_2O_4ClBr$: C, 49.40; H, 3.22; N, 6.40; Cl, 8.10. Found: C,49.48; H, 3.25; N,6.34; Cl, 8.12. The phenylcarbamoylamino compound (0.1 g, 0.23 mmole) was heated with 0.02 g of thiourea (0.26 mmole) in 10 ml of THF at 70° C. overnight. The final product precipitated out, yield 0.04 g, 36%, m.p. 161°–163° C. (dec.), mass spectrum (FAB+) m/e=433 (M-Br). Anal. Calc. for $C_{19}H_{18}N_4O_4ClBrS$:0.25 THF: C, 45.12; H, 3.86; N, 10.53; Cl, 6.67. Found: C, 44.83; H, 3.92; N, 10.12; Cl, 6.41.

7-(Ethylcarbamoylamino)-4-chloro-3-(2-isothiureidoethoxy)isocoumarin, 7-(t-butylcarbamoylamino)-4-chloro-3-(2-isothiureidoethoxy)isocoumarin, 7-(benzylthiocarbamoylamino)-4-chloro-3-(2-isothiureidoethoxy)isocoumarin, 7-(ethylthiocarbamoylamino)-4-chloro-3-(2-isothiureidoethoxy)isocoumarin, 7-(4-fluorobenzyl) thiocarbamoylamino-4-chloro-3-(2-isothiureidoethoxy) isocoumarin, and 7-(2,5-dimethylbenzyl) thiocarbamoylamino-4-chloro-3-(2-isothiureidoethoxy) isocoumarin can be prepared by the same procedure.

EXAMPLE SHC2

Preparation of 7-(acetylamino)-4-chloro-3-(3-isothiureidopropoxy) isocoumarin:

7-Amino-3(3-bromopropoxy)-4-chloroisocoumarin was synthesized as previously described (Kam, et al., 1988). This compound (0.33 g, 1 mmole) was heated with 0.15 g of acetic anhydride (1.5 mmole) in 20 ml of dry THF. After a few minutes, a yellow solid precipitated out. After 3 hrs, the solution was concentrated to 5 ml, and the solid was filtered to give 0.37 g of 7-(acetylamino)-4-chloro-3-(3-bromopropoxy) isocoumarin, m.p. 170°–172° C.; mass spectrum: m/e=375 (M+). The acetylated isocoumarin (0.15 g, 0.4 mmole) was treated with thiourea (0.036 g, 0.47 mmole) to give 0.9 g of the final product, (yield 50%), m.p. 180°–181° C., mass spectrum m/e=370 (M+—Br). Anal. Calc. for $C_{15}H_{17}N_3O_4ClBrS$: C, 39.97; H, 3.80; N, 9.32; Cl 7.87. Found: C, 39.86; H 3.83; N, 9.29; Cl, 7.85.

7-trifluoroacetylamino-4-chloro-3-(3-isothiureidopropoxy) isocoumarin, 7-heptafluorobutyroylamino-4-chloro-3-(3-isothiureidopropoxy) isocoumarin, 7-succinylamino-4-chloro-3-(3-isothiureidopropoxy) isocoumarin, and 7-(o-phthalyl)amino-4-chloro-3-(3-isothiureidopropoxy) isocoumarin can be prepared by the same procedure.

EXAMPLE SHC3

Preparation of 7-(benzylcarbamoylamino)-4-chloro-3-(3-isothiureidopropoxy) isocoumarin:

7-(benzylcarbamoylamino)-4-chloro-3(3-bromopropoxy) isocoumarin was prepared from the reaction of benzyl isocyanate with 7-amino-4-chloro-3-(3-bromopropoxy) isocoumarin as described above, m.p. 188°–189° C., mass spectrum: m/e=359 (M+-benzyl). The final product was obtained from the reaction of 7-(benzylcarbamoylamino)-4-chloro-3-(3-bromopropoxy) isocoumarin with thiourea as described above (yield 74%), m.p. 165°–166° C.; mass spectrum (FAB+) m/e=461 (M+—Br). Anal. Calc. for $C_{21}H_{22}N_4O_4ClBrS$:0.75 THF: C, 48.36; H, 4.70; N, 9.40; Cl, 6.56. Found: C, 48.13; H, 4.87; N, 9.65; Cl, 6.15.

EXAMPLE SHC4

Preparation of 7-(phenylacetylamino)-4-chloro-3-(2-isothiureidoethoxy) isocoumarin:

7-Amino-4-chloro-3-(2-bromoethoxy) isocoumarin (0.15 g, 0.47 mmole) was first mixed with phenylacetyl chloride (0.09 g, 0.55 mmole) in 10 ml of THF, triethylamine (0.05 g, 0.47 mmole) was then added and the reaction mixture was stirred at r.t. overnight. After $Et_3N·HCl$ salt was removed by filtration, the product 7-(phenylacetylamino)-4-chloro-3-(2-bromoethoxy) isocoumarin was crystallized from THF and Pet. ether (yield, 73%), m.p. 165°–169° C.; mass spectrum; m/e=436.7 (M+). The phenylacetyamino derivative (0.1 g) was heated with thiourea (0.02 g) to give the product 0.05 g (yield, 40%), m.p. 115°–120° C.; mass spectrum (FAB+) m/e=432 (M+—Br). Anal. Calc. for $C_{20}H_{19}N_3O_4ClBrS$.0.5 $H_2O$: C 45.99; H, 3.83; N, 8.05; Cl 6.80. Found: C, 46.09; H, 4.17; N, 8.02; Cl, 6.79.

EXAMPLE SHC5

Preparation of 7-(R-α-methylbenzylcarbamoylamino)-4-chloro-3-(2-isothiureidoethoxy) isocoumarin:

7-(R-α-methylbenzylcarbamoylamino)-4-chloro-3-(2-bromoethoxy) isocoumarin was synthesized in the same manner as described above, m.p. 183°–185° C.; mass spectrum m/e=464 (M+). This compound (0.1 g) reacted with thiourea (0.02 g) under the same condition described above to form the final product 7-(R-α-methylbenzylcarbamoylamino)-4-chloro-3-(2-isothiureidoethoxy) isocoumarin (0.078 g), m.p. 143°–150° C.; mass spectrum (FAB+) m/e=461 (M+—Br). Anal. Calc. for $C_{21}H_{22}N_4O_4ClBrS$.0.5$H_2O$: C, 45.75; H, 4.35; N, 10.17; Cl, 6.44. Found: C, 44.95; H 4.31; N, 10.02; Cl, 6.36.

EXAMPLE SHC6

Preparation of 7-(D-phenylalanylamino)-4-chloro-3(2-isothiureidoethoxy) isocoumarin:

Boc-D-Phe (0.33 g, 1.2 mmole) reacted with 1,3-dicyclohexylcarbodiimide (0.13 g, 0.6 mmole) in 10 ml THF at 0° C. for 1 hour to form the symmetric anhydride, and then 7-amino-4-chloro-3(2-bromoethoxy) isocoumarin (0.2 g, 0.6 mmole) was added. The reaction was stirred at r.t. overnight and the precipitate 7-(Boc-D-Phe-amino)-4-chloro-3-(2-bromoethoxy) isocoumarin was formed (0.29 g, 71%). TLC one spot, m.p. 180°-182° C.; mass spectrum m/3=566(M+). Anal. Calc. for $C_{25}H_{26}N_2O_6ClBr$: C, 53.07; H, 4.63; N, 4.95; Cl 6.27. Found: C, 53.25: H, 4.66; N, 4.87; Cl, 6.24. Boc-D-Phe compound (0.2 g, 0.35 mmole) was reacted with thiourea (0.027 g, 0.35 mmole) in the same manner to give 7-(Boc-D-phenylalanylamino)-4-chloro-3-(2-isothiureidoethoxy) isocoumarin (0.14 g), yield 62%, mass spectrum (FAB+) m/e=561 (M+—Br). This compound (0.1 g) was dissolved in 3 ml of THF at 0° C. and then the solvent was evaporated to dryness. The final product precipitated out after addition of ether, one spot on TLC ($CH_3CN:H_2O:AcOH=8:1:1$); mass spectrum (FAB+) m/e=462 (M+—Br—$CF_3COO$).

7-Boc-alanylamino-4-chloro-3-(2-isothiureidoethoxy) isocoumarin, 7-benzoylamino-Ala-4-chloro-3(2-isothiureidoethoxy) isocoumarin, 7-benzoylamino-Phe-4-chloro-3-(2-isothiureidoethoxy) isocoumarin and 7-Boc-valylamino-4-chloro-3-(2-isothiureidoethoxy) isocoumarin can be prepared by the same procedure.

EXAMPLE SHC7

Preparation of 7-(Boc-alanylalanylamino)-4-chloro-3-(2-isothiureidoethoxy) isocoumarin:

7-(Boc-alanylalanylamino)-4-chloro-3-(2-bromoethoxy) isocoumarin was synthesized in the same manner, m.p. 147°-151° C.; mass spectrum m/e=561 (M+). Anal. Calc: C, 47.12: H, 4.85. Found: C, 47.18; H, 4.87. This compound (0.2 g) was reacted with thiourea (0.03 g) by the same procedure to form 7-(Boc-alanylalanylamino)-4-chloro-3-(2-isothiureidoethoxy) isocoumarin (0.04 g), mass spectrum m/e=556 (M+—Br).

7-(Alanylalanylamino)-4-chloro-3(2-isothiureidoethoxy) isocoumarin was prepared by deblocking of Boc-Ala-Ala-NH—CiTEtOIC with trifluoroacetic acid, mass spectrum (FAB+) m/e=456 (M+—Br—$CF_3COO$).

EXAMPLE SHC8

Preparation of 7-(phenylthiocarbamoylamino)-4-chloro-3-(2-isothiureidoethoxy) isocoumarin:

7-(Phenylthiocarbamoylamino)-4-chloro-3-(2-bromoethoxy) isocoumarin was prepared from the reaction of phenyl isothiocyanate with 7-amino-4-chloro-3-(2-bromoethoxy) isocoumarin, yield 59%, m.p. 157°-158° C.; mass spectrum m/e=361 (M+-PhNH+1). Anal. Calc.: C, 48.36; H, 3.39. Found: C, 48.26; H, 3.40. The bromoethoxy compound was then reacted with thiourea by the same procedure to give the final product, yield 32%; mass spectrum (FAB+) m/e 449 (M+—Br).

EXAMPLE SHC9

Preparation of 7-(m-carboxyphenylthiocarbamoylamino)-4-chloro-3-(2-bromoethoxy) isocoumarin was prepared from the reaction of m-carboxyphenyl isothiocyanate with 7-amino-4-chloro-3-(2-bromoethoxy) isocoumarin, yield 64%, m.p. 157°-158° C.; mass spectrum m/e 361 (M+—(COOH)$PhNH_+$—Br).

7-(3-Fluorobenzoyl)amino-4-chloro-3-(2-isothiureidoethoxy) isocoumarin, 7-(3-nitrobenzoyl) amino-4-chloro-3-(2-isothiureidoethoxy) isocoumarin, 7-diphenylacetylamino-4-chloro-3-(2-isothiureidoethoxy) isocoumarin, 7-diphenylpropionylamino-4-chloro-3-(2-isothiureidoethoxy) isocoumarin, 7-(p-toluenesulfonyl) amino-4-chloro-3-(2-isothiureidoethoxy) isocoumarin, and 7-(α-toluenesulfonyl) amino-4-chloro-3-(2-isothiureidoethoxy) isocoumarin can be prepared from the reaction of corresponding 7-substituted-4-chloro-3-(2-bromoethoxy) isocoumarin with thiourea as described above. 7-substituted-4-chloro-3-(2bromoethoxy) isocoumarin can be synthesized by reacting 7-amino-4-chloro-3-(2bromoethoxy) isocoumarin with appropriate acid chloride or sulfonyl chloride in the presence of $Et_3N$.

7-Ethoxycarbonylamino-4-chloro-3-(2-isothiureidoethoxy) isocoumarin, 7-benzyloxycarbonylamino-4-chloro-3-(2-isothiureidoethoxy) isocoumarin, and 7-phenoxycarbonylamino-4-chloro-3-(2-isothiureidoethoxy) isocoumarin can be prepared from the reaction of 7-substituted-4-chloro-3-(2-bromoethoxy) isocoumarin with thiourea. 7-Ethoxycarbonylamino-4-chloro-3-(2-bromoethoxy) isocoumarin, 7-benzyloxycarbonylamino-4-chloro-3-(2-bromoethoxy) isocoumarin and 7-phenoxycarbonylamino-4-chloro-3-(2-bromoethoxy) isocoumarin can be synthesized by reacting 7-amino-4-chloro-3-(2-bromoethoxy) isocoumarin with the corresponding chloroformate.

C. PEPTIDE KETO-COMPOUNDS

Peptide α-ketoesters, peptide α-ketoacids, and peptide α-ketoamides are transition state analog inhibitors for serine proteases and cysteine proteases. While these subclasses of compounds are chemically distinguishable, for simplicity, all of these compounds will be referred to collectively herein as the "Peptide Keto-Compounds".

The interactions of peptides with serine and cysteine proteases are designated herein using the nomenclature of Schechter, I., and Berger, A., 1967, Biochem. Biophys. Res. Commun. 27:157-162 (incorporated herein by reference). The individual amino acid residues of a substrate or inhibitor are designated P1, P2, etc. and the corresponding subsites of the enzyme are designated S1, S2, etc. The scissile bond of the substrate is P1-P1'. The primary recognition site of serine proteases is S1. The most important recognition subsites of cysteine proteases are S1 and S2.

Amino acid residues and blocking groups are designated using standard abbreviations [see J. Biol. Chem. 260, 14–42 (1985) for nomenclature rules; incorporated herein by reference]. An amino acid residue (AA) in a peptide or inhibitor structure refers to the part structure —NH—CHR1—CO—, where R1 is the side chain of the amino acid AA. A peptide α-ketoester residue would be designated -AA-CO—OR which represents the part structure —NH—CHR1—CO—CO—OR. Thus, the ethyl ketoester derived from benzoyl alanine would be designated Bz-Ala-CO—OEt which represents $C_6H_5CO$—NH—CHMe-CO—CO—OEt. Likewise, peptide ketoacid residues residues would be designated -AA-CO—OH. Further, peptide ketoamide residues are designated -AA-CO—NH—R. Thus, the ethyl keto amide derived from Z-Leu-Phe-OH would be designated Z-Leu-Phe-CO—NH-Et which represents C6H5CH2OCO—NH—CH(CH2CHMe2)-CO—NH—CH(CH2Ph)-CO—CO—NH-Et.

Peptide α-ketoesters containing amino acid residues with hydrophobic side chain at the P1 site have also been found to be excellent inhibitors of several cysteine proteases including papain, cathepsin B and calpain.

Calpains can be inhibited by peptide inhibitors having several different active groups. Structure-activity relationships with the commercially available in vitro inhibitors of Calpain, such as peptide aldehydes, have revealed that Calpains strongly prefer Leu or Val in the P2 position. These enzymes are inhibited by inhibitors having a wide variety of amino acids in the P1 position, but are generally more effectively inhibited by inhibitors having amino acids with nonpolar or hydrophobic side chains in the P1 position. Thus, we have discovered that another particular class of compounds exhibiting Calpain inhibitory activity, when used in accordance with the present invention, are the Peptide Keto-Compounds. These are compounds of the general structure:

$$M\text{—}(aa)_n\text{—}\overset{O}{\underset{\|}{C}}\text{—}Q\text{—}R$$

or a pharmaceutically acceptable salt, wherein:
M represents NH2—CO—, NH2—CS—, NH2—SO2—, X—NH—CO—, X—NH—CS—, X—NH—SO2—, X—CO—, X—CS—, X—SO2—, X—O—CO—, or X—O—CS—, H, acetyl, carbobenzoxy, succinyl, methyloxysuccinyl, butyloxycarbonyl;
X is selected from the group consisting of C1-6 alkyl, C1-6 fluoroalkyl, C1-6 alkyl substituted with J, C1-6 fluoroalkyl substituted with J, 1-admantyl, 9-fluorenyl, phenyl, phenyl substituted with K, phenyl disubstituted with K, phenyl trisubstituted with K, naphthyl, naphthyl substituted with K, naphthyl disubstituted with K, naphthyl trisubstituted with K, C1-6 alkyl with an attached phenyl group, C1-6 alkyl with two attached phenyl groups, C1-6 alkyl with an attached phenyl group substituted with K, and C1-6 alkyl with two attached phenyl groups substituted with K;
J is selected from the group consisting of halogen, COOH, OH, CN, NO2, NH2, C1-6 alkoxy, C1-6 alkylamine, C1-6 dialkylamine, C1-6 alkyl-O—CO—, C1-6 alkyl-O—CO—NH, and C1-6 alkyl-S—;
K is selected from the group consisting of halogen, C1-6 alkyl, C1-6 perfluoroalkyl, C1-6 alkoxy, NO2, CN, OH, CO2H, amino, C1-6 alkylamino, C2-12 dialkylamino, C1-6 acyl, and C1-6 alkoxy-CO—, and C1-6 alkyl-S—;
aa represents a blocked or unblocked amino acid of the L or D configuration, preferably selected from the group consisting of: alanine, valine, leucine, isoleucine, proline, methionine, methionine sulfoxide, phenylalanine, tryptophan, glycine, serine, threonine, cysteine, tyrosine, asparagine, glutamine, aspartic acid, glutamic acid, lysine, arginine, histidine, phenylglycine, beta-alanine, norleucine (nle), norvaline (nva), alpha-aminobutyric acid (abu), epsilon-aminocaproic acid, citrulline, hydroxyproline, homoarginine, ornithine or sarcosine;
n is a number from 1 to 20;
Q is O or NH,
R represents H, C1-6 alkyl, C1-6 fluoroalkyl, C1-6 chloroalkyl, benzyl, C1-6 alkyl substituted with phenyl, C1-6 alkyl with an attached phenyl group substituted with K.

Thus, the Peptide Keto-Compounds can be divided into the Peptide Ketoesters, Peptide Ketoacids and Peptide Ketoamides. Each of the compounds can also be classified based on the number of amino acids contained within the compound, such as an amino acid peptide, dipeptide, tripeptide, tetrapeptide, pentapeptide and so on.

We have found certain subclasses of Peptide α-Ketoester compounds to be particularly useful as Calpain Inhibitors when used in accordance with the present invention. These subclasses are referred to herein as the Dipeptide α-Ketoesters (Subclass A), the Dipeptide α-Ketoesters (Subclass B), the Tripeptide α-Ketoesters (Subclass A), the Tripeptide α-Ketoesters (Subclass B), the Tetrapeptide α-Ketoesters and the Amino Acid Peptide α-Ketoesters. All of these subclasses are considered to be to be within the class of Peptide Keto-Compounds.

The Dipeptide α-Ketoesters (Subclass A) are compounds of the formula:

$$M_1\text{-}AA_2\text{-}AA_1\text{-}CO\text{—}O\text{—}R_1$$

or a pharmaceutically acceptable salt, wherein
$M_1$ represents H, NH2—CO—, NH2—CS—, NH2—SO2—, X—NH—CO—, X2N—CO—, X—NH—CS—, X2N—CS—, X—NH—SO2—, X2N—SO2—, X—CO—, X—CS—, X—SO2—, X—O—CO—, or X—O—CS—;
X is selected from the group consisting of $C_{1\text{-}10}$ alkyl, $C_{1\text{-}10}$ fluoroalkyl, $C_{1\text{-}10}$ alkyl substituted with J, $C_{1\text{-}10}$ fluoroalkyl substituted with J, 1-admantyl, 9-fluorenyl, phenyl, phenyl substituted with K, phenyl disubstituted with K, phenyl trisubstituted with K, naphthyl, naphthyl substituted with K, naphthyl disubstituted with K, naphthyl trisubstituted with K, $C_{1\text{-}10}$ alkyl with an attached phenyl group, $C_{1\text{-}10}$ alkyl with two attached phenyl groups, $C_{1\text{-}10}$ alkyl with an attached phenyl group substituted with K, and $C_{1\text{-}10}$ alkyl with two attached phenyl groups substituted with K, $C_{1\text{-}10}$ alkyl with an attached phenoxy group, and $C_{1\text{-}10}$ alkyl with an attached phenoxy group substituted with K on the phenoxy group;
J is selected from the group consisting of halogen, COOH, OH, CN, NO2, NH2, $C_{1\text{-}10}$ alkoxy, $C_{1\text{-}10}$ alkylamine, $C_{2\text{-}12}$ dialkylamine, $C_{1\text{-}10}$ alkyl-O—CO—, $C_{1\text{-}10}$ alkyl-O—CO—NH—, and $C_{1\text{-}10}$ alkyl-S—;
K is selected from the group consisting of halogen, $C_{1\text{-}10}$ alkyl, $C_{1\text{-}10}$ perfluoroalkyl, $C_{1\text{-}10}$ alkoxy, NO2, CN, OH, CO2H, amino, $C_{1\text{-}10}$ alkylamino, $C_{2\text{-}12}$ dialkylamino, $C_{1\text{-}10}$ acyl, and $C_{1\text{-}10}$ alkoxy-CO—, and $C_{1\text{-}10}$ alkyl-S—;
$AA_1$ is a side chain blocked or unblocked amino acid with the L configuration, D configuration, or no chirality at the α-carbon selected from the group consisting of alanine, valine, leucine, isoleucine, proline, methionine, methionine sulfoxide, phenylalanine, tryptophan, serine, threonine, cysteine, tyrosine, asparagine, glutamine, aspartic acid, glutamic acid, lysine, arginine, histidine, phenylglycine, beta-alanine, norleucine, norvaline, alpha-aminobutyric acid, epsilon-aminocaproic acid, citrulline, hydroxyproline, ornithine, homoarginine, sarcosine, indoline 2-carboxylic acid, 2-azetidinecarboxylic acid, pipecolinic acid (2-piperidine carboxylic acid), O-methylserine, O-ethylserine, S-methylcysteine, S-ethylcysteine, S-benzylcysteine, $NH_2$—$CH(CH_2CHEt_2)$-$COOH$, alpha-aminoheptanoic acid, $NH_2$—$CH(CH_2$-1-napthyl)-$COOH$, $NH_2$—$CH(CH_2$-2-napthyl)-$COOH$, $NH_2$—$CH(CH_2$-cyclohexyl)-$COOH$, $NH_2$—$CH(CH_2$-cyclopentyl)-$COOH$, $NH_2$—$CH(CH_2$-cyclobutyl)-$COOH$, $NH_2$—$CH(CH_2$-cyclopropyl)-$COOH$, trifluoroleucine, and hexafluoroleucine;

$AA_2$ is a side chain blocked or unblocked amino acid with the L configuration, D configuration, or no chirality at the α-carbon selected from the group consisting of leucine, isoleucine, proline, methionine, methionine sulfoxide, phenylalanine, tryptophan, glycine, serine, threonine, cysteine, tyrosine, asparagine, glutamine, aspartic acid, glutamic acid, lysine, arginine, histidine, phenylglycine, beta-alanine, norleucine, norvaline, alpha-aminobutyric acid, epsilon-aminocaproic acid, citrulline, hydroxyproline, ornithine, homoarginine, sarcosine, indoline 2-carboxylic acid, 2-azetidinecarboxylic acid, pipecolinic acid (2-piperidine carboxylic acid), O-methylserine, O-ethylserine, S-methylcysteine, S-ethylcysteine, S-benzylcysteine, $NH_2$—$CH(CH_2CHEt_2)$-$COOH$, alpha-aminoheptanoic acid, $NH_2$—$CH(CH_2$-1-napthyl)-$COOH$, $NH_2$—$CH(CH_2$-2-napthyl)-$COOH$, $NH_2$—$CH(CH_2$-cyclohexyl)-$COOH$, $NH_2$—$CH(CH_2$-cyclopentyl)-$COOH$, $NH_2$—$CH(CH_2$-cyclobutyl)-$COOH$, $NH_2$—$CH(CH_2$-cyclopropyl)-$COOH$, trifluoroleucine, and hexafluoroleucine;

$R_1$ is selected from the group consisting of H, $C_{1-20}$ alkyl, $C_{1-20}$ alkyl with a phenyl group attached to the $C_{1-20}$ alkyl, and $C_{1-20}$ alkyl with an attached phenyl group substituted with K.

The Dipeptide α-Ketoesters (Subclass B) are compounds of the structure:

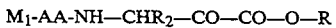

or a pharmaceutically acceptable salt, wherein $M_1$ represents H, $NH_2$—CO—, $NH_2$—CS—, $NH_2$—$SO_2$—, X—NH—CO—, $X_2N$—CO—, X—NH—CS—, $X_2N$—CS—, X—NH—$SO_2$—, $X_2N$—SO—, X—CO—, X—CS—, X—$SO_2$—, X—O—CO—, or X—O—CS—;

X is selected from the group consisting of $C_{1-10}$ alkyl, $C_{1-10}$ fluoroalkyl, $C_{1-10}$ alkyl substituted with J, $C_{1-10}$ fluoroalkyl substituted with J, 1-admantyl, 9-fluorenyl, phenyl, phenyl substituted with K, phenyl disubstituted with K, phenyl trisubstituted with K, naphthyl, naphthyl substituted with K, naphthyl disubstituted with K, naphthyl trisubstituted with K, $C_{1-10}$ alkyl with an attached phenyl group, $C_{1-10}$ alkyl with two attached phenyl groups, $C_{1-10}$ alkyl with an attached phenyl group substituted with K, and $C_{1-10}$ alkyl with two attached phenyl groups substituted with K, $C_{1-10}$ alkyl with an attached phenoxy group, and $C_{1-10}$ alkyl with an attached phenoxy group substituted with K on the phenoxy group;

J is selected from the group consisting of halogen, COOH, OH, CN, $NO_2$, $NH_2$, $C_{10}$ alkoxy, $C_{1-10}$ alkylamine, $C_{2-12}$ dialkylamine, $C_{1-10}$ alkyl-O—CO—, $C_{1-10}$ alkyl-O—CO—NH—, and $C_{1-10}$ alkyl-S—;

K is selected from the group consisting of halogen, $C_{1-10}$ alkyl, $C_{1-10}$ perfluoroalkyl, $C_{1-10}$ alkoxy, $NO_2$, CN, OH, $CO_2H$, amino, $C_{1-10}$ alkylamino, $C_{2-12}$ dialkylamino, $C_1$-$C_{10}$ acyl, and $C_{1-10}$ alkoxy-CO—, and $C_{1-10}$ alkyl-S—;

AA is a side chain blocked or unblocked amino acid with the L configuration, D configuration, or no chirality at the α-carbon selected from the group consisting of alanine, valine, leucine, isoleucine, proline, methionine, methionine sulfoxide, phenylalanine, tryptophan, glycine, serine, threonine, cysteine, tyrosine, asparagine, glutamine, aspartic acid, glutamic acid, lysine, arginine, histidine, phenylglycine, beta-alanine, norleucine, norvaline, alpha-aminobutyric acid, epsilon-aminocaproic acid, citrulline, hydroxyproline, ornithine, homoarginine, sarcosine, indoline 2-carboxylic acid, 2-azetidinecarboxylic acid, pipecolinic acid (2-piperidine carboxylic acid), O-methylserine, O-ethylserine, S-methylcysteine, S-ethylcysteine, S-benzylcysteine, $NH_2$—$CH(CH_2CHEt_2)$-$COOH$, alpha-aminoheptanoic acid, $NH_2$—$CH(CH_2$-1-napthyl)-$COOH$, $NH_2$—$CH(CH_2$-2-napthyl)-$COOH$, $NH_2$—$CH(CH_2$-cyclohexyl)-$COOH$, $NH_2$—$CH(CH_2$-cyclopentyl)-$COOH$, $NH_2$—$CH(CH_2$-cyclobutyl)-$COOH$, $NH_2$—$CH(CH_2$-cyclopropyl)-$COOH$, trifluoroleucine, and hexafluoroleucine;

$R_2$ represents $C_{1-8}$ branched and unbranched alkyl, $C_{1-8}$ branched and unbranched cyclized alkyl, or $C_{1-8}$ branched and unbranched fluoroalkyl;

R is selected from the group consisting of H, $C_{1-20}$ alkyl, $C_{1-20}$ alkyl with a phenyl group attached to the $C_{1-20}$ alkyl, and $C_{1-20}$ alkyl with an attached phenyl group substituted with K.

The Tripeptide α-Ketoesters (Subclass A) are compounds of the structure:

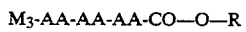

or a pharmaceutically acceptable salt, wherein $M_3$ represents H, $NH_2$—CO—, $NH_2$—CS—, $NH_2$—$SO_2$—, X—NH—CO—, $X_2N$—CO—, X—NH—CS—, $X_2N$—CS—, X—NH—$SO_2$—, $X_2N$—$SO_2$—, X—CO—, X—CS—, X—$SO_2$—, T—O—CO—, or X—O—CS—;

X is selected from the group consisting of $C_{1-10}$ alkyl, $C_{1-10}$ fluoroalkyl, $C_{1-10}$ alkyl substituted with J, $C_{1-10}$ fluoroalkyl substituted with J, 1-admantyl, 9-fluorenyl, phenyl, phenyl substituted with K, phenyl disubstituted with K, phenyl trisubstituted with K, naphthyl, naphthyl substituted with K, naphthyl disubstituted with K, naphthyl trisubstituted with K, $C_{1-10}$ alkyl with an attached phenyl group, $C_{1-10}$ alkyl with two attached phenyl groups, $C_{1-10}$ alkyl with an attached phenyl group substituted with K, and $C_{1-10}$ alkyl with two attached phenyl groups substituted with K, $C_{1-10}$ alkyl with an attached phenoxy group, and $C_{1-10}$ alkyl with an attached phenoxy group substituted with K on the phenoxy group;

T is selected from the group consisting of $C_{1-10}$ alkyl, $C_{1-10}$ fluoroalkyl, $C_{1-10}$ alkyl substituted with J, $C_{1-10}$ fluoroalkyl substituted with J, 1-admantyl, 9-fluorenyl, phenyl, phenyl substituted with K, phenyl disubstituted with K, phenyl trisubstituted with K, naphthyl, naphthyl substituted with K, naphthyl disubstituted with K, naphthyl trisubstituted with K, $C_{2-10}$ alkyl with an attached phenyl group, $C_{1-10}$ alkyl with two attached phenyl groups, $C_{1-10}$ alkyl with an attached phenyl group substituted with K, and $C_{1-10}$ alkyl with two attached phenyl groups substituted with K;

J is selected from the group consisting of halogen, COOH, OH, CN, $NO_2$, $NH_2$, $C_{1-10}$ alkoxy, $C_{1-10}$ alkylamine, $C_{2-12}$ dialkylamine, $C_{1-10}$ alkyl-O—CO—, $C_{1-10}$ alkyl-O—CO—NH—, and $C_{1-10}$ alkyl-S—;

K is selected from the group consisting of halogen, $C_{1-10}$ alkyl, $C_{1-10}$ perfluoroalkyl, $C_{1-10}$ alkoxy, $NO_2$, CN, OH, $CO_2H$, amino, $C_{1-10}$ alkylamino, $C_{2-12}$ dialkylamino, $C_1$-$C_{10}$ acyl, and $C_{1-10}$ alkoxy-CO—, and $C_{1-10}$ alkyl-S—;

AA is a side chain blocked or unblocked amino acid with the L configuration, D configuration, or no chirality at the α-carbon selected from the group consisting of alanine, valine, leucine, isoleucine, proline, methionine, methionine sulfoxide, phenylalanine, tryptophan, glycine, serine, threonine, cysteine, tyrosine, asparagine, glutamine, aspartic acid, glutamic acid, lysine, arginine, histidine, phenylglycine, beta-alanine, norleucine, norvaline, alpha-aminobutyric acid, epsilon-aminocaproic acid, citrulline, hydroxyproline, ornithine, homoarginine, sarcosine, indoline 2-carboxylic acid, 2-azetidinecarboxylic acid, pipecolinic acid (2-piperidine carboxylic acid), O-methylserine, O-ethylserine, S-methylcysteine, S-ethylcysteine, S-benzylcysteine, $NH_2$—$CH(CH_2CHEt_2)$-COOH, alpha-aminoheptanoic acid, $NH_2$—$CH(CH_2$-1-napthyl)-COOH, $NH_2$—$CH(CH_2$-2-napthyl)-COOH, $NH_2$—$CH(CH_2$-cyclohexyl)-COOH, $NH_2$—$CH(CH_2$-cyclopentyl)-COOH, $NH_2$—$CH(CH_2$-cyclobutyl)-COOH, $NH_2$—$CH(CH_2$-cyclopropyl)-COOH, trifluoroleucine, and hexafluoroleucine;

R is selected from the group consisting of H, $C_{2-20}$ alkyl, $C_{1-20}$ alkyl with a phenyl group attached to the $C_{1-10}$ alkyl, and $C_{1-20}$ alkyl with an attached phenyl group substituted with K.

The Tripeptide α-Ketoesters (Subclass B) are compounds of the structure:

or a pharmaceutically acceptable salt, wherein $M_3$ represents H, $NH_2$—CO—, $NH_2$—CS—, $NH_2$—$SO_2$—, X—NH—CO—, $X_2N$—CO—, X—NH—CS—, $X_2N$—CS—, X—NH—$SO_2$—, $X_2N$—$SO_2$—, X—CO—, X—CS—, X—$SO_2$—, T—O—CO—, or X—O—CS—;

X is selected from the group consisting of $C_{1-10}$ alkyl, $C_{1-10}$ fluoroalkyl, $C_{1-10}$ alkyl substituted with J, $C_{1-10}$ fluoroalkyl substituted with J, 1-admantyl, 9-fluorenyl, phenyl, phenyl substituted with K, phenyl disubstituted with K, phenyl trisubstituted with K, naphthyl, naphthyl substituted with K, naphthyl disubstituted with K, naphthyl trisubstituted with K, $C_{1-10}$ alkyl with an attached phenyl group, $C_{1-10}$ alkyl with two attached phenyl groups, $C_{1-10}$ alkyl with an attached phenyl group substituted with K, and $C_{1-10}$ alkyl with two attached phenyl groups substituted with K, $C_{1-10}$ alkyl with an attached phenoxy group, and $C_{1-10}$ alkyl with an attached phenoxy group substituted with K on the phenoxy group;

T is selected from the group consisting of $C_{1-10}$ alkyl, $C_{1-10}$ fluoroalkyl, $C_{1-10}$ alkyl substituted with J, $C_{1-10}$ fluoroalkyl substituted with J, 1-admantyl, 9-fluorenyl, phenyl, phenyl substituted with K, phenyl disubstituted with K, phenyl trisubstituted with K, naphthyl, naphthyl substituted with K, naphthyl disubstituted with K, naphthyl trisubstituted with K, $C_{2-10}$ alkyl with an attached phenyl group, $C_{1-10}$ alkyl with two attached phenyl groups, $C_{1-10}$ alkyl with an attached phenyl group substituted with K, and $C_{1-10}$ alkyl with two attached phenyl groups substituted with K;

J is selected from the group consisting of halogen, COOH, OH, CN, $NO_2$, $NH_2$, $C_{1-10}$ alkoxy, $C_{1-10}$ alkylamine, $C_{1-10}$ dialkylamine, $C_{1-10}$ alkyl-O—CO—, $C_{1-10}$ alkyl-O—CO—NH—, and $C_{1-10}$ alkyl-S—;

K is selected from the group consisting of halogen, $C_{1-10}$ alkyl, $C_{1-10}$ perfluoroalkyl, $C_{1-10}$ alkoxy, $NO_2$, CN, OH, $CO_2H$, amino, $C_{1-10}$ alkylamino, $C_{2-12}$ dialkylamino, $C_1$-$C_{10}$ acyl, and $C_{1-10}$ alkoxy-CO—, and $C_{1-10}$ alkyl-S—;

AA is a side chain blocked or unblocked amino acid with the L configuration, D configuration, or no chirality at the α-carbon selected from the group consisting of alanine, valine, leucine, isoleucine, proline, methionine, methionine sulfoxide, phenylalanine, tryptophan, glycine, serine, threonine, cysteine, tyrosine, asparagine, glutamine, aspartic acid, glutamic acid, lysine, arginine, histidine, phenylglycine, beta-alanine, norleucine, norvaline, alpha-aminobutyric acid, epsilon-aminocaproic acid, citrulline, hydroxyproline, ornithine, homoarginine, sarcosine, indoline 2-carboxylic acid, 2-azetidinecarboxylic acid, pipecolinic acid (2-piperidine carboxylic acid), O-methylserine, O-ethylserine, S-methylcysteine, S-ethylcysteine, S-benzylcysteine, $NH_2$—$CH(CH_2CHEt_2)$-COOH, alpha-aminoheptanoic acid, $NH_2$—$CH(CH_2$-1-napthyl)-COOH, $NH_2$—$CH(CH_2$-2-napthyl)-COOH, $NH_2$—$CH(CH_2$-cyclohexyl)-COOH, $NH_2$—$CH(CH_2$-cyclopentyl)-COOH, $NH_2$—$CH(CH_2$-cyclobutyl)-COOH, $NH_2$—$CH(CH_2$-cyclopropyl)-COOH, trifluoroleucine, and hexafluoroleucine;

$R_2$ represents $C_{1-8}$ branched and unbranched alkyl, $C_{1-8}$ branched and unbranched cyclized alkyl, or $C_{1-8}$ branched and unbranched fluoroalkyl;

R is selected from the group consisting of H, $C_{1-20}$ alkyl, $C_{1-20}$ alkyl with a phenyl group attached to the $C_{1-20}$ alkyl, and $C_{1-20}$ alkyl with an attached phenyl group substituted with K.

The Tetrapeptide α-Ketoesters are compounds of the structure:

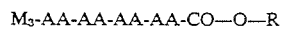

or a pharmaceutically acceptable salt, wherein $M_3$ represents H, $NH_2$—CO—, $NH_2$—CS—, $NH_2$—$SO_2$—, X—NH—CO—, $X_2N$—CO—, X—NH—CS—, $X_2N$—CS—, X—NH—$SO_2$—, $X_2N$—$SO_2$—, X—CO—, X—CS—, X—$SO_2$—, T—O—CO—, or X—O—CS—;

X is selected from the group consisting of $C_{1-10}$ alkyl, $C_{1-10}$ fluoroalkyl, $C_{1-10}$ alkyl substituted with J, $C_{1-10}$ fluoroalkyl substituted with J, 1-admantyl, 9-fluorenyl, phenyl, phenyl substituted with K, phenyl disubstituted with K, phenyl trisubstituted with K, naphthyl, naphthyl substituted with K, naphthyl disubstituted with K, naphthyl trisubstituted with K, $C_{1-10}$ alkyl with an attached phenyl group, $C_{1-10}$ alkyl with two attached phenyl groups, $C_{1-10}$ alkyl with an attached phenyl group substituted with K, and $C_{1-10}$ alkyl with two attached phenyl groups substituted with K, $C_{1-10}$ alkyl with an attached phenoxy group, and $C_{1-10}$ alkyl with an attached phenoxy group substituted with K on the phenoxy group;

T is selected from the group consisting of $C_{1-10}$ alkyl, $C_{1-10}$ fluoroalkyl, $C_{1-10}$ alkyl substituted with J, $C_{1-10}$ fluoroalkyl substituted with J, 1-admantyl, 9-fluorenyl, phenyl, phenyl substituted with K, phenyl disubstituted with K, phenyl trisubstituted with K, naphthyl, naphthyl substituted with K, naphthyl disubstituted with K, naphthyl trisubstituted with K, $C_{2-10}$ alkyl with an attached phenyl group, $C_{1-10}$ alkyl with two attached phenyl groups, $C_{1-10}$ alkyl with an attached phenyl group substituted with K, and $C_{1-10}$ alkyl with two attached phenyl groups substituted with K;

J is selected from the group consisting of halogen, COOH, OH, CN, $NO_2$, $NH_2$, $C_{1-10}$ alkoxy, $C_{1-10}$ alkylamine, $C_{2-12}$ dialkylamine, $C_{1-10}$ alkyl-O—CO—, $C_{1-10}$ alkyl-O—CO—NH—, and $C_{1-10}$ alkyl-S—;

K is selected from the group consisting of halogen, $C_{1-10}$ alkyl, $C_{1-10}$ perfluoroalkyl, $C_{1-10}$ alkoxy, $NO_2$, CN, OH, $CO_2H$, amino, $C_{1-10}$ alkylamino, $C_{2-12}$ dialkylamino, $C_1-C_{10}$ acyl, and $C_{1-10}$ alkoxy-CO—, and $C_{1-10}$ alkyl-S—;

AA is a side chain blocked or unblocked amino acid with the L configuration, D configuration, or no chirality at the α-carbon selected from the group consisting of alanine, valine, leucine, isoleucine, proline, methionine, methionine sulfoxide, phenylalanine, tryptophan, glycine, serine, threonine, cysteine, tyrosine, asparagine, glutamine, aspartic acid, glutamic acid, lysine, arginine, histidine, phenylglycine, beta-alanine, norleucine, norvaline, alpha-aminobutyric acid, epsilon-aminocaproic acid, citrulline, hydroxyproline, ornithine, homoarginine, sarcosine, indoline 2-carboxylic acid, 2-azetidinecarboxylic acid, pipecolinic acid (2-piperidine carboxylic acid), O-methylserine, O-ethylserine, S-methylcysteine, S-ethylcysteine, S-benzylcysteine, $NH_2$—CH($CH_2CHEt_2$)-COOH, alpha-aminoheptanoic acid, $NH_2$—CH($CH_2$-1-napthyl)-COOH, $NH_2$—CH($CH_2$-2-napthyl)-COOH, $NH_2$—CH($CH_2$-cyclohexyl)-COOH, $NH_2$—CH($CH_2$-cyclopentyl)-COOH, $NH_2$—CH($CH_2$-cyclobutyl)-COOH, $NH_2$—CH($CH_2$-cyclopropyl)-COOH, trifluoroleucine, and hexafluoroleucine;

$AA_4$ is a side chain blocked or unblocked amino acid with the L configuration, D configuration, or no chirality at the α-carbon selected from the group consisting of leucine, isoleucine, methionine, methionine sulfoxide, phenylalanine, tryptophan, glycine, serine, threonine, cysteine, tyrosine, asparagine, glutamine, aspartic acid, glutamic acid, lysine, arginine, histidine, phenylglycine, beta-alanine, norleucine, norvaline, alpha-aminobutyric acid, epsilon-aminocaproic acid, citrulline, hydroxyproline, ornithine, homoarginine, sarcosine, indoline 2-carboxylic acid, 2-azetidinecarboxylic acid, pipecolinic acid (2-piperidine carboxylic acid), O-methylserine, O-ethylserine, S-methylcysteine, S-ethylcysteine, S-benzylcysteine, $NH_2$—CH($CH_2CHEt_2$)-COOH, alpha-aminoheptanoic acid, $NH_2$—CH($CH_2$-1-napthyl)-COOH, $NH_2$—CH($CH_2$-2-napthyl)-COOH, $NH_2$—CH($CH_2$-cyclohexyl)-COOH, $NH_2$—CH($CH_2$-cyclopentyl)-COOH, $NH_2$—CH($CH_2$-cyclobutyl)-COOH, $NH_2$—CH($CH_2$-cyclopropyl)-COOH, trifluoroleucine, and hexafluoroleucine;

R is selected from the group consisting of H, $C_{1-20}$ alkyl, $C_{1-20}$ alkyl with a phenyl group attached to the $C_{1-20}$ alkyl, and $C_{1-20}$ alkyl with an attached phenyl group substituted with K.

The Amino Acid Peptide α-Ketoesters are compounds of the structure:

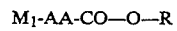

or a pharmaceutically acceptable salt, wherein
$M_1$ represents H, $NH_2$—CO—, $NH_2$—CS—, $NH_2$—SO_2$—, X—NH—CO—, $X_2N$—CO—, X—NH—CS—, $X_2N$—CS—, X—NH—$SO_2$—, $X_2N$—$SO_2$—, Y—CO—, X—CS—, X—$SO_2$—, X—O—CO—, or X—O—CS—;

X is selected from the group consisting of $C_{1-10}$ alkyl, $C_{1-10}$ fluoroalkyl, $C_{1-10}$ alkyl substituted with J, $C_{1-10}$ fluoroalkyl substituted with J, 1-admantyl, 9-fluorenyl, phenyl, phenyl substituted with K, phenyl disubstituted with K, phenyl trisubstituted with K, naphthyl, naphthyl substituted with K, naphthyl disubstituted with K, naphthyl trisubstituted with K, $C_{1-10}$ alkyl with an attached phenyl group, $C_{1-10}$ alkyl with two attached phenyl groups, $C_{1-10}$ alkyl with an attached phenyl group substituted with K, and $C_{1-10}$ alkyl with two attached phenyl groups substituted with K, $C_{1-10}$ alkyl with an attached phenoxy group, and $C_{1-10}$ alkyl with an attached phenoxy group substituted with K on the phenoxy group;

Y is selected from the group consisting of $C_{6-10}$ alkyl, $C_{1-10}$ fluoroalkyl, $C_{1-10}$ alkyl substituted with J, $C_{1-10}$ fluoroalkyl substituted with J, 1-admantyl, 9-fluorenyl, phenyl substituted with K, phenyl disubstituted with K, phenyl trisubstituted with K, naphthyl, naphthyl substituted with K, naphthyl disubstituted with K, naphthyl trisubstituted with K, $C_{1-10}$ alkyl with an attached phenyl group, $C_{1-10}$ alkyl with two attached phenyl groups, $C_{1-10}$ alkyl with an attached phenyl group substituted with K, and $C_{1-10}$ alkyl with two attached phenyl groups substituted with K;

J is selected from the group consisting of halogen, COOH, OH, CN, $NO_2$, $NH_2$, $C_{1-10}$ alkoxy, $C_{1-10}$ alkylamine, $C_{2-12}$ dialkylamine, $C_{1-10}$ alkyl-O—CO—, $C_{1-10}$ alkyl-O—CO—NH—, and $C_{1-10}$ alkyl-S—;

K is selected from the group consisting of halogen, $C_{1-10}$ alkyl, $C_{1-10}$ perfluoroalkyl, $C_{1-10}$ alkoxy, $NO_2$, CN, OH, $CO_2H$, amino, $C_{1-10}$ alkylamino, $C_{2-12}$ dialkylamino, $C_1-C_{10}$ acyl, and $C_{1-10}$ alkoxy-CO—, and $C_{1-10}$ alkyl-S—;

AA is a side chain blocked or unblocked amino acid with the L configuration, D configuration, or no chirality at the α-carbon selected from the group consisting of alanine, valine, leucine, isoleucine, proline, methionine, methionine sulfoxide, phenylalanine, tryptophan, glycine, serine, threonine, cysteine, tyrosine, asparagine, glutamine, aspartic acid, glutamic acid, lysine, arginine, histidine, phenylglycine, beta-alanine, norleucine, norvaline, alpha-aminobutyric acid, epsilon-aminocaproic acid, citrulline, hydroxyproline, ornithine, homoarginine, sarcosine, indoline 2-carboxylic acid, 2-azetidinecarboxylic acid, pipecolinic acid (2-piperidine carboxylic acid), O-methylserine, O-ethylserine, S-methylcysteine, S-ethylcysteine, S-benzylcysteine, $NH_2—CH(CH_2CHEt_2)$-COOH, alpha-aminoheptanoic acid, $NH_2—CH(CH_2$-1-napthyl)-COOH, $NH_2—CH(CH_2$-2-napthyl)-COOH, $NH_2—CH(CH_2$-cyclohexyl)-COOH, $NH_2—CH(CH_2$-cyclopentyl)-COOH, $NH_2—CH(CH_2$-cyclobutyl)-COOH, $NH_2—CH(CH_2$-cyclopropyl)-COOH, trifluoroleucine, and hexafluoroleucine;

R is selected from the group consisting of H, $C_{1-20}$ alkyl, $C_{1-20}$ alkyl with a phenyl group attached to the $C_{1-20}$ alkyl, and $C_{1-20}$ alkyl with an attached phenyl group substituted with K.

The following Peptide Ketoester compounds are representative of the Peptide Keto-Compounds found to be useful as Calpain inhibitors within the context of the present invention:

Bz-DL-Ala-COOEt
Bz-DL-Ala-COOBzl
Bz-DL-Ala-COOnBu
Bz-DL-Phe-COOEt
Bz-DL-Ala-COOCH2—C6H4—CF3 (para)
Bz-DL-Arg-COOEt
Bz-DL-Lys-COOEt
Z-Ala-DL-Ala-COOEt
Z-Ala-DL-Ala-COOBzl
Z-Ala-DL-Ala-COOnBu
MeO-Suc-Ala-DL-Ala-COOMe
Z-Leu-Nva-COOEt
Z-Leu-Nle-COOEt
Z-Leu-Phe-COOEt
Z-Leu-Abu-COOEt
Z-Leu-Met-COOEt
Z-Phe-DL-Phe-COOEt
H-Gly-DL-Lys-COOEt
H-Ala-DL-Lys-COOEt
H-Pro-DL-Lys-COOEt
H-Phe-DL-Lys-COOEt
Z-Ala-Ala-DL-Ala-COOEt
Z-Ala-Pro-DL-Ala-COOEt
Z-Ala-Ala-DL-Abu-COOEt
Z-Ala-Ala-DL-Abu-COOBzl
Z-Ala-Ala-DL-Abu-COOCH2—C6H4—CF3 (para)
MeO-Suc-Val-Pro-DL-Phe-COOMe
H-Leu-Ala-DL-Lys-COOEt
Z-Ala-Ala-Ala-DL-Ala-COOEt
MeO-Suc-Ala-Ala-Pro-DL-Abu-COOMe.
Z-Leu-Phe-COOEt
PhCO-Abu-COOEt
(CH3)2CH(CH2)2CO-Abu-COOEt
CH3CH2CH)2CHCO-Abu-COOEt
Ph(CH2)6CO-Abu-COOEt
Z-Leu-4-Cl-Phe-COOEt Z-Leu-Leu-Abu-COOEt
Z-Leu-Leu-Phe-COOEt
2-NapSO2-Leu-Abu-COOEt
2-NapSO2-Leu-Leu-Abu-COOEt
Z-Leu-NLeu-CO2Et
Z-Leu-Phe-CO2Bu
Z-Leu-Abu-CO2Bu
Z-Leu-Phe-CO2Bzl
Z-Leu-Abu-CO2Bzl.

We have found certain subclasses of Peptide Ketoacid Compounds to be particularly useful when used in accordance with the present invention. These are subclasses are the Dipeptide α-Ketoacids (Subclass A), the Dipeptide α-Ketoacids (Subclass B), the Tripeptide α-Ketoacids, the Tetrapeptide α-Ketoacids and the Amino Acid peptide α-Ketoacids. All of these are considered to be within the class of Peptide Keto-Compounds.

The Dipeptide α-Ketoacids (Subclass A) are compounds of the structure:

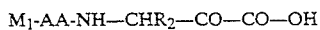

$M_1$-AA-NH—CHR_2—CO—CO—OH or a pharmaceutically acceptable salt, wherein
$M_1$ represents H, $NH_2—CO—$, $NH_2—CS—$, $NH_2—SO_2—$, X—NH—CO—, $X_2N—CO—$, X—NH—CS—, $X_2N—CS—$, X—NH—$SO_2$—, $X_2N—SO_2—$, X—CO—, X—CS—, X—$SO_2$—, X—O—CO—, or X—CS—;

X is selected from the group consisting of $C_{1-10}$ alkyl, $C_{1-10}$ fluoroalkyl, $C_{1-10}$ alkyl substituted with J, $C_{1-10}$ fluoroalkyl substituted with J, 1-admantyl, 9-fluorenyl, phenyl, phenyl substituted with K, phenyl disubstituted with K, phenyl trisubstituted with K, naphthyl, naphthyl substituted with K, naphthyl disubstituted with K, naphthyl trisubstituted with K, $C_{1-10}$ alkyl with an attached phenyl group, $C_{1-10}$ alkyl with two attached phenyl groups, $C_{1-10}$ alkyl with an attached phenyl group substituted with K, $C_{1-10}$ alkyl with two attached phenyl groups substituted with K, $C_{1-10}$ alkyl with an attached phenoxy group, and $C_{1-10}$ alkyl with an attached phenoxy group substituted with K on the phenoxy group;

J is selected from the group consisting of halogen, COOH, OH, CN, $NO_2$, $NH_2$, $C_{1-10}$ alkoxy, $C_{1-10}$ alkylamine, $C_{2-12}$ dialkylamine, $C_{1-10}$ alkyl-O—CO—, $C_{1-10}$ alkyl-O—CO—NH—, and $C_{1-10}$ alkyl-S—;

K is selected from the group consisting of halogen, $C_{1-10}$ alkyl, $C_{1-10}$ perfluoroalkyl, $C_{1-10}$ alkoxy, $NO_2$, CN, OH, $CO_2H$, amino, $C_{1-10}$ alkylamino, $C_{2-12}$ dialkylamino, $C_{1-10}$ acyl, and $C_{1-10}$ alkoxy-CO—, and $C_{1-10}$ alkyl-S—;

AA is a side chain blocked or unblocked amino acid with the L configuration, D configuration, or no chirality at the α-carbon selected from the group consisting of alanine, valine, leucine, isoleucine, proline, methionine, methionine sulfoxide, phenylalanine, tryptophan, glycine, serine, threonine, cysteine, tyrosine, asparagine, glutamine, aspartic acid, glutamic acid, lysine, arginine, histidine, phenylglycine, beta-alanine, norleucine, norvaline, alpha-aminobutyric acid, epsilon-aminocaproic acid, citrulline, hydroxyproline, ornithine, homoarginine, sarcosine, indoline 2-carboxylic acid, 2-azetidinecarboxylic acid, pipecolinic acid (2-piperidine carboxylic acid), O-methylserine, O-ethylserine, S-methylcysteine, S-ethylcysteine, S-benzylcysteine, $NH_2-CH(CH_2CHEt_2)$-COOH, alpha-aminoheptanoic acid, $NH_2-CH(CH_2-1-napthyl)$-COOH, $NH_2-CH(CH_2-2-napthyl)$-COOH, $NH_2-CH(CH_2$-cyclohexyl)-COOH, $NH_2-CH(CH_2$-cyclopentyl)-COOH, $NH_2-CH(CH_2$-cyclobutyl)-COOH, $NH_2-CH(CH_2$-cyclopropyl)-COOH, trifluoroleucine, and hexafluoroleucine;

$R_2$ represents $C_{1-8}$ branched and unbranched alkyl, $C_{1-8}$ branched and unbranched cyclized alkyl, or $C_{1-8}$ branched and unbranched fluoroalkyl.

The Dipeptide α-Ketoacids (Subclass B) are compounds of the structure:

or a pharmaceutically acceptable salt, wherein $M_1$ represents H, $NH_2-CO-$, $NH_2-CS-$, $NH_2-SO_2-$, $X-NH-CO-$, $X_2N-CO-$, $X-NH-CS-$, $X_2N-CS-$, $X-NH-SO_2-$, $X_2N-SO_2-$, $X-CO-$, $X-CS-$, $X-SO_2-$, $X-O-CO-$, or $X-O-CS-$;

X is selected from the group consisting of $C_{1-10}$ alkyl, $C_{1-10}$ fluoroalkyl, $C_{1-10}$ alkyl substituted with J, $C_{1-10}$ fluoroalkyl substituted with J, 1-admantyl, 9-fluorenyl, phenyl, phenyl substituted with K, phenyl disubstituted with K, phenyl trisubstituted with K, naphthyl, naphthyl substituted with K, naphthyl disubstituted with K, naphthyl trisubstituted with K, $C_{1-10}$ alkyl with an attached phenyl group, $C_{1-10}$ alkyl with two attached phenyl groups, $C_{1-10}$ alkyl with an attached phenyl group substituted with K, and $C_{1-10}$ alkyl with two attached phenyl groups substituted with K, $C_{1-10}$ alkyl with an attached phenoxy group, and $C_{1-10}$ alkyl with an attached phenoxy group substituted with K on the phenoxy group;

J is selected from the group consisting of halogen, COOH, OH, CN, $NO_2$, $NH_2$, $C_{1-10}$ alkoxy, $C_{1-10}$ alkylamine, $C_{2-12}$ dialkylamine, $C_{1-10}$ alkyl-O—CO—, $C_{1-10}$ alkyl-O—CO—NH—, and $C_{1-10}$ alkyl-S—;

K is selected from the group consisting of halogen, $C_{1-10}$ alkyl, $C_{1-10}$ perfluoroalkyl, $C_{1-10}$ alkoxy, $NO_2$, CN, OH, $CO_2H$, amino, $C_{1-10}$ alkylamino, $C_{2-12}$ dialkylamino, $C_1-C_{10}$ acyl, and $C_{1-10}$ alkoxy-CO—, and $C_{1-10}$ alkyl-S—;

$AA_1$ is a side chain blocked or unblocked amino acid with the L configuration, D configuration, or no chirality at the α-carbon selected from the group consisting of alanine, valine, leucine, isoleucine, proline, methionine, methionine sulfoxide, phenylalanine, tryptophan, serine, threonine, cysteine, tyrosine, asparagine, glutamine, aspartic acid, glutamic acid, lysine, arginine, histidine, phenylglycine, beta-alanine, norleucine, norvaline, alpha-aminobutyric acid, epsilon-aminocaproic acid, citrulline, hydroxyproline, ornithine, homoarginine, sarcosine, indoline 2-carboxylic acid, 2-azetidinecarboxylic acid, pipecolinic acid (2-piperidine carboxylic acid), O-methylserine, O-ethylserine, S-methylcysteine, S-ethylcysteine, S-benzylcysteine, $NH_2-CH(CH_2CHEt_2)$-COOH, alpha-aminoheptanoic acid, $NH_2-CH(CH_2-1-napthyl)$-COOH, $NH_2-CH(CH_2-2-napthyl)$-COOH, $NH_2-CH(CH_2$-cyclohexyl)-COOH, $NH_2-CH(CH_2$-cyclopentyl)-COOH, $NH_2-CH(CH_2$-cyclobutyl)-COOH, $NH_2-CH(CH_2$-cyclopropyl)-COOH, trifluoroleucine, and hexafluoroleucine;

$AA_2$ is a side chain blocked or unblocked amino acid with the L configuration, D configuration, or no chirality at the α-carbon selected from the group consisting of alanine, valine, leucine, isoleucine, proline, methionine, methionine sulfoxide, phenylalanine, tryptophan, glycine, serine, threonine, cysteine, tyrosine, asparagine, glutamine, aspartic acid, glutamic acid, lysine, arginine, histidine, phenylglycine, beta-alanine, norleucine, norvaline, alpha-aminobutyric acid, epsilon-aminocaproic acid, citrulline, hydroxyproline, ornithine, homoarginine, sarcosine, indoline 2-carboxylic acid, 2-azetidinecarboxylic acid, pipecolinic acid (2-piperidine carboxylic acid), O-methylserine, O-ethylserine, S-methylcysteine, S-ethylcysteine, S-benzylcysteine, $NH_2-CH(CH_2CHEt_2)$-COOH, alpha-aminoheptanoic acid, $NH_2-CH(CH_2-1-napthyl)$-COOH, $NH_2-CH(CH_2-2-napthyl)$-COOH, $NH_2-CH(CH_2$-cyclohexyl)-COOH, $NH_2-CH(CH_2$-cyclopentyl)-COOH, $NH_2-CH(CH_2$-cyclobutyl)-COOH, $NH_2-CH(CH_2$-cyclopropyl)-COOH, trifluoroleucine, and hexafluoroleucine.

The Tripeptide α-Ketoacids are compounds of the structure:

or a pharmaceutically acceptable salt, wherein $M_1$ represents H, $NH_2-CO-$, $NH_2-CS-$, $NH_2-SO_2-$, $X-NH-CO-$, $X_2N-CO-$, $X-NH-CS-$, $X_2N-CS-$, $X-NH-SO_2-$, $X_2N-SO_2-$, $X-CO-$, $X-CS-$, $X-SO_2-$, $X-O-CO-$, or $X-O-CS-$;

X is selected from the group consisting of $C_{1-10}$ alkyl, $C_{1-10}$ fluoroalkyl, $C_{1-10}$ alkyl substituted with J, $C_{1-10}$ fluoroalkyl substituted with J, 1-admantyl, 9-fluorenyl, phenyl, phenyl substituted with K, phenyl disubstituted with K, phenyl trisubstituted with K, naphthyl, naphthyl substituted with K, naphthyl disubstituted with K, naphthyl trisubstituted with K, $C_{1-10}$ alkyl with an attached phenyl group, $C_{1-10}$ alkyl with two attached phenyl groups, $C_{1-10}$ alkyl with an attached phenyl group substituted with K, and $C_{1-10}$ alkyl with two attached phenyl groups substituted with K, $C_{1-10}$ alkyl with an attached phenoxy group, and $C_{1-10}$ alkyl with an attached phenoxy group substituted with K on the phenoxy group;

J is selected from the group consisting of halogen, COOH, OH, CN, $NO_2$, $NH_2$, $C_{1-10}$ alkoxy, $C_{1-10}$ alkylamine, $C_{2-12}$ dialkylamine, $C_{1-10}$ alkyl-O—CO—, $C_{1-10}$ alkyl-O—CO—NH—, and $C_{1-10}$ alkyl-S—;

K is selected from the group consisting of halogen, $C_{1-10}$ alkyl, $C_{1-10}$ perfluoroalkyl, $C_{1-10}$ alkoxy, $N_2$, CN, OH, $CO_2H$, amino, $C_{1-10}$ alkylamino, $C_{2-12}$ dialkylamino, $C_{1-10}$ acyl, and $C_{1-10}$ alkoxy-CO—, and $C_{1-10}$ alkyl-S—;

AA is a side chain blocked or unblocked amino acid with the L configuration, D configuration, or no chirality at the α-carbon selected from the group consisting of alanine, valine, leucine, isoleucine, proline, methionine, methionine sulfoxide, phenylalanine, tryptophan, glycine, serine, threonine, cysteine, tyrosine, asparagine, glutamine, aspartic acid, glutamic acid, lysine, arginine, histidine, phenylglycine, beta-alanine, norleucine, norvaline, alpha-aminobutyric acid, epsilon-aminocaproic acid, citrulline, hydroxyproline, ornithine, homoarginine, sarcosine, indoline 2-carboxylic acid, 2-azetidinecarboxylic acid, pipecolinic acid (2-piperidine carboxylic acid), O-methylserine, O-ethylserine, S-methylcysteine, S-ethylcysteine, S-benzylcysteine, $NH_2$—$CH(CH_2CHEt_2)$-$COOH$, alpha-aminoheptanoic acid, $NH_2$—$CH(CH_2$-1-napthyl)-$COOH$, $NH_2$—$CH(CH_2$-2-napthyl)-$COOH$, $NH_2$—$CH(CH_2$-cyclohexyl)-$COOH$, $NH_2$—$CH(CH_2$-cyclopentyl)-$COOH$, $NH_2$—$CH(CH_2$-cyclobutyl)-$COOH$, $NH_2$—$CH(CH_2$-cyclopropyl)-$COOH$, trifluoroleucine, and hexafluoroleucine.

The Tetrapeptide α-Ketoacids are compounds of the structure:

$M_1$-AA-AA-AA-AA-CO—OH or a pharmaceutically acceptable salt, wherein
$M_1$ represents H, $NH_2$—CO—, $NH_2$—CS—, $NH_2$—$SO_2$—, X—NH—CO—, $X_2$N—CO—, X—NH—CS—, $X_2$N—CS—, X—NH—$SO_2$—, $X_2$N—$SO_2$—, $Y_1$—CO—, X—CS—, X—$SO_2$—, X—O—CO—, or X—O—CS—;

X is selected from the group consisting of $C_{1-10}$ alkyl, $C_{1-10}$ fluoroalkyl, $C_{1-10}$ alkyl substituted with J, $C_{1-10}$ fluoroalkyl substituted with J, 1-admantyl, 9-fluorenyl, phenyl, phenyl substituted with K, phenyl disubstituted with K, phenyl trisubstituted with K, naphthyl, naphthyl substituted with K, naphthyl disubstituted with K, naphthyl trisubstituted with K, $C_{1-10}$ alkyl with an attached phenyl group, $C_{1-10}$ alkyl with two attached phenyl groups, $C_{1-10}$ alkyl with an attached phenyl group substituted with K, and $C_{1-10}$ alkyl with two attached phenyl groups substituted with K, $C_{1-10}$ alkyl with an attached phenoxy group, and $C_{1-10}$ alkyl with an attached phenoxy group substituted with K on the phenoxy group;

$Y_1$ is selected from the group consisting of $C_{2-10}$ alkyl, $C_{1-10}$ fluoroalkyl, $C_{1-10}$ alkyl substituted with J, $C_{1-10}$ fluoroalkyl substituted with J, 1-admantyl, 9-fluorenyl, phenyl, phenyl substituted with K, phenyl disubstituted with K, phenyl trisubstituted with K, naphthyl, naphthyl substituted with K, naphthyl disubstituted with K, naphthyl trisubstituted with K, $C_{1-10}$ alkyl with an attached phenyl group, $C_{1-10}$ alkyl with two attached phenyl groups, $C_{1-10}$ alkyl with an attached phenyl group substituted with K, and $C_{1-10}$ alkyl with two attached phenyl groups substituted with K;

J is selected from the group consisting of halogen, COOH, OH, CN, $NO_2$, $NH_2$, $C_{1-10}$ alkoxy, $C_{1-10}$ alkylamine, $C_{2-12}$ dialkylamine, $C_{1-10}$ alkyl-O—CO—, $C_{1-10}$ alkyl-O—CO—NH—, and $C_{1-10}$ alkyl-S—;

K is selected from the group consisting of halogen, $C_{1-10}$ alkyl, $C_{1-10}$ perfluoroalkyl, $C_{1-10}$ alkoxy, $NO_2$, CN, OH, $CO_2H$, amino, $C_{1-10}$ alkylamino, $C_{2-12}$ dialkylamino, $C_1$-$C_{10}$ acyl, and $C_{1-10}$ alkoxy-CO—, and $C_{1-10}$ alkyl-S—;

AA is a side chain blocked or unblocked amino acid with the L configuration, D configuration, or no chirality at the α-carbon selected from the group consisting of alanine, valine, leucine, isoleucine, proline, methionine, methionine sulfoxide, phenylalanine, tryptophan, glycine, serine, threonine, cysteine, tyrosine, asparagine, glutamine, aspartic add, glutamic acid, lysine, arginine, histidine, phenylglycine, beta-alanine, norleucine, norvaline, alpha-aminobutyric acid, epsilon-aminocaproic acid, citrulline, hydroxyproline, ornithine, homoarginine, sarcosine, indoline 2-carboxylic acid, 2-azetidinecarboxylic acid, pipecolinic acid (2-piperidine carboxylic acid), O-methylserine, O-ethylserine, S-methylcysteine, S-ethylcysteine, S-benzylcysteine, $NH_2$—$CH(CH_2CHEt_2)$-$COOH$, alpha-aminoheptanoic acid, $NH_2$—$CH(CH_2$-1-napthyl)-$COOH$, $NH_2$—$CH(CH_2$-2-napthyl)-$COOH$, $NH_2$—$CH(CH_2$-cyclohexyl)-$COOH$, $NH_2$—$CH(CH_2$-cyclopentyl)-$COOH$, $NH_2$—$CH(CH_2$-cyclobutyl)-$COOH$, $NH_2$—$CH(CH_2$-cyclopropyl)-$COOH$, trifluoroleucine, and hexafluoroleucine.

The Amino Acid Peptide α-Ketoacids are compounds of the structure:

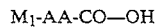

$M_1$-AA-CO—OH or a pharmaceutically acceptable salt, wherein
$M_1$ represents H, $NH_2$—CO—, $NH_2$—CS—, $NH_2$—$SO_2$—, X—NH—CO—, $X_2$N—CO—, X—NH—CS—, $X_2$N—CS—, X—NH—$SO_2$—, $X_2$N—$SO_2$—, $Y_2$—CO—, X—CS—, X—$SO_2$—, X—O—CO—, or X—O—CS—;

X is selected from the group consisting of $C_{1-10}$ alkyl, $C_{1-10}$ fluoroalkyl, $C_{1-10}$ alkyl substituted with J, $C_{1-10}$ fluoroalkyl substituted with J, 1-admantyl, 9-fluorenyl, phenyl, phenyl substituted with K, phenyl disubstituted with K, phenyl trisubstituted with K, naphthyl, naphthyl substituted with K, naphthyl disubstituted with K, naphthyl trisubstituted with K, $C_{1-10}$ alkyl with an attached phenyl group, $C_{1-10}$ alkyl with two attached phenyl groups, $C_{1-10}$ alkyl with an attached phenyl group substituted with K, and $C_{1-10}$ alkyl with two attached phenyl groups substituted with K, $C_{1-10}$ alkyl with an attached phenoxy group, and $C_{1-10}$ alkyl with an attached phenoxy group substituted with K on the phenoxy group;

$Y_2$ is selected from the group consisting of $C_{1-10}$ alkyl, $C_{1-10}$ fluoroalkyl, $C_{1-10}$ alkyl substituted with J, $C_{1-10}$ fluoroalkyl substituted with J, 1-admantyl, 9-fluorenyl, phenyl substituted with K, phenyl disubstituted with K, phenyl trisubstituted with K, naphthyl, naphthyl substituted with K, naphthyl disubstituted with K, naphthyl trisubstituted with K, $C_{1-10}$ alkyl with an attached phenyl group, $C_{1-10}$ alkyl with two attached phenyl groups, $C_{1-10}$ alkyl with an attached phenyl group substituted with K, and $C_{1-10}$ alkyl with two attached phenyl groups substituted with K;

J is selected from the group consisting of halogen, COOH, OH, CN, $NO_2$, $NH_2$, $C_{1-10}$ alkoxy, $C_{1-10}$ alkylamine, $C_{2-12}$ dialkylamine, $C_{1-10}$ alkyl-O—CO—, $C_{1-10}$ alkyl-O—CO—NH—, and $C_{1-10}$ alkyl-S—;

K is selected from the group consisting of halogen, $C_{1-10}$ alkyl, $C_{1-10}$ perfluoroalkyl, $C_{1-10}$ alkoxy, $NO_2$, CN, OH, $CO_2H$, amino, $C_{1-10}$ alkylamino, $C_{2-12}$ dialkylamino, $C_{1-10}$ acyl, and $CO_{1-10}$ alkoxy-CO—, and $C_{1-10}$ alkyl-S—;

AA is a side chain blocked or unblocked amino acid with the L configuration, D configuration, or no chirality at the α-carbon selected from the group consisting of alanine, valine, leucine, isoleucine, proline, methionine, methionine sulfoxide, phenylalanine, tryptophan, glycine, serine, threonine, cysteine, tyrosine, asparagine, glutamine, aspartic acid, glutamic acid, lysine, arginine, histidine, phenylglycine, beta-alanine, norleucine, norleucine, norvaline, alpha-aminobutyric acid, epsilon-aminocaproic acid, citrulline, hydroxyproline, ornithine, homoarginine, sarcosine, indoline 2-carboxylic acid, 2-azetidinecarboxylic acid, pipecolinic acid (2-piperidine carboxylic acid), O-methylserine, O-ethylserine, S-methylcysteine, S-ethylcysteine, S-benzylcysteine, $NH_2$—$CH(CH_2$-$CHEt_2)$-COOH, alpha-aminoheptanoic acid, $NH_2$—$CH(CH_2$-1-napthyl)-COOH, $NH_2$—$CH(CH_2$-2-napthyl)-COOH, $NH_2$—$CH(CH_2$-cyclohexyl)-COOH, $NH_2$—$CH(CH_2$-cyclopentyl)-COOH, $NH_2$—$CH(CH_2$-cyclobutyl)-COOH, $NH_2$—$CH(CH_2$-cyclopropyl)-COOH, trifluoroleucine, and hexafluoroleucine.

The following Peptide Ketoacid compounds are representative of the Peptide Keto-Compounds found to be useful as Calpain inhibitors within the context of the present invention:

Bz-DL-Lys-COOH
Bz-DL-Ala-COOH
Z-Leu-Phe-COOH
Z-Leu-Abu-COOH.

The peptide α-ketoamides are transition state analogue inhibitors for cysteine proteases, such as Calpain. We have found that Peptide α-ketoamides containing amino acid residues with hydrophobic side chains at the $P_1$ site are excellent inhibitors of several cysteine proteases including calpain I and calpain II.

We have found five subclasses of the peptide ketoamides to be particularly effective in inhibiting Calpain. These subclasses are referred to herein as Dipeptide α-Ketoamides (Subclass A), Dipeptide α-Ketoamides (Subclass B), Tripeptide α-Ketoamides, Tetrapeptide α-Ketoamides and Amino Acid α-Ketoamides. All of these subclasses are considered herein to be within the class of Peptide Keto-Compounds.

The Dipeptide a-Ketoamides (Subclass A) have the following structural formula:

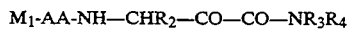

or a pharmaceutically acceptable salt, wherein
$M_1$ represents H, $NH_2$—CO—, $NH_2$—CS—, $NH_2$—$SO_2$—, X—NH—CO—, $X_2N$—CO—, X—NH—CS—, $X_2N$—CS—, X—NH—$SO_2$—, $X_2N$—$SO_2$—, X—CO—, X—CS—, X—$SO_2$—, X—O—CS—;

X is selected from the group consisting of $C_{1-10}$ alkyl, $C_{1-10}$ fluoroalkyl, $C_{1-10}$ alkyl substituted with J, $C_{1-10}$ fluoroalkyl substituted with J, 1-admantyl, 9-fluorenyl, phenyl, phenyl substituted with K, phenyl disubstituted with K, phenyl trisubstituted with K, naphthyl, naphthyl substituted with K, naphthyl disubstituted with K, naphthyl trisubstituted with K, $C_{1-10}$ alkyl with an attached phenyl group, $C_{1-10}$ alkyl with two attached phenyl groups, $C_{1-10}$ alkyl with an attached phenyl group substituted with K, $C_{1-10}$ alkyl with two attached phenyl groups substituted with K, $C_{1-10}$ alkyl with an attached phenoxy group, and $C_{1-10}$ alkyl with an attached phenoxy group substituted with K on the phenoxy group;

J is selected from the group consisting of halogen, COOH, OH, CN, $NO_2$, $NH_2$, $C_{1-10}$ alkoxy, $C_{1-10}$ alkylamine, $C_{2-12}$ dialkylamine, $C_{1-10}$ alkyl-O—CO—, $C_{1-10}$ alkyl-O—CO—NH—, and $C_{1-10}$ alkyl-S—;

K is selected from the group consisting of halogen, $C_{1-10}$ alkyl, $C_{1-10}$ perfluoroalkyl, $C_{1-10}$ alkoxy, $NO_2$, CN, OH, $CO_2H$, amino, $C_{1-10}$ alkylamino, $C_{2-12}$ dialkylamino, $C_1$–$C_{10}$ acyl, $C_{1-10}$ alkoxy-CO—, and $C_{1-10}$ alkyl-S—;

AA is a side chain blocked or unblocked amino acid with the L configuration, D configuration, or no chirality at the α-carbon selected from the group consisting of alanine, valine, leucine, isoleucine, proline, methionine, methionine sulfoxide, phenylalanine, tryptophan, glycine, serine, threonine, cysteine, tyrosine, asparagine, glutamine, aspartic acid, glutamic acid, lysine, arginine, histidine, phenylglycine, beta-alanine, norleucine, norvaline, α-aminobutyric acid, epsilon-aminocaproic acid, citrulline, hydroxyproline, ornithine, homoarginine, sarcosine, indoline 2-carboxylic acid, 2-azetidinecarboxylic acid, pipecolinic acid (2-piperidine carboxylic acid), O-methylserine, O-ethylserine, S-methylcysteine, S-ethylcysteine, S-benzylcysteine, $NH_2$—$CH(CH_2CHEt_2)$-COOH, α-aminoheptanoic acid, $NH_2$—$CH(CH_2$-1-napthyl)-COOH, $NH_2$—$CH(CH_2$-2-napthyl)-COOH, $NH_2$—$CH(CH_2$-cyclohexyl)-COOH, $NH_2$—$CH(CH_2$-cyclopentyl)-COOH, $NH_2$—$CH(CH_2$-cyclobutyl)-COOH, $NH_2$—$CH(CH_2$-cyclopropyl)-COOH, trifluoroleucine, and hexafluoroleucine;

$R_2$ is selected from the group consisting of $C_{1-8}$ branched and unbranched alkyl, $C_{1-8}$ branched and unbranched cyclized alkyl, and $C_{1-8}$ branched and unbranched fluoroalkyl;

$R_3$ and $R_4$ are selected independently from the group consisting of H, $C_{1-20}$ alkyl, $C_{1-20}$ cyclized alkyl, $C_{1-20}$ alkyl with a phenyl group attached to the $C_{1-20}$ alkyl, $C_{1-20}$ cyclized alkyl with an attached phenyl group, $C_{1-20}$ alkyl with an attached phenyl group substituted with K, $C_{1-20}$ alkyl with an attached phenyl group disubstituted with K, $C_{1-20}$ alkyl with an attached phenyl group trisubstituted with K, $C_{1-20}$ cyclized alkyl with an attached phenyl group substituted with K, $C_{1-10}$ alkyl with a morpholine [—$N(CH_2CH_2)O$] ring attached through nitrogen to the alkyl, $C_{1-10}$ alkyl with a piperidine ring attached through nitrogen to the alkyl, $C_{1-10}$ alkyl with a pyrrolidine ring attached through nitrogen to the alkyl, $C_{1-20}$ alkyl with an OH group attached to the alkyl, —$CH_2C$-$H_2OCH_2CH_2OH$, $C_{1-10}$ with an attached 4-pyridyl group, $C_{1-10}$ with an attached 3-pyridyl group, $C_{1-10}$ with an attached 2-pyridyl group, $C_{1-10}$ with an attached cyclohexyl group, —NH—$CH_2CH_2$-(4-hydroxyphenyl), and —NH—$CH_2CH_2$-(3-indolyl).

The Dipeptide α-Ketoamides (Subclass B) have the following structural formula:

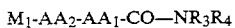

or a pharmaceutically acceptable salt, wherein $M_1$ represents H, $NH_2-CO-$, $NH_2-CS-$, $NH_2-SO_2-$, $X-NH-CO-$, $X_2N-CO-$, $X-NH-CS-$, $X_2N-CS-$, $X-NH-SO_2-$, $X_2N-SO_2-$, $X-CO-$, $X-CS-$, $X-SO_2-$, $X-O-CO-$, or $X-O-CS-$;

X is selected from the group consisting of $C_{1-10}$ alkyl, $C_{1-10}$ fluoroalkyl, $C_{1-10}$ alkyl substituted with J, $C_{1-10}$ fluoroalkyl substituted with J, 1-admantyl, 9-fluorenyl, phenyl, phenyl substituted with K, phenyl disubstituted with K, phenyl trisubstituted with K, naphthyl, naphthyl substituted with K, naphthyl disubstituted with K, naphthyl trisubstituted with K, $C_{1-10}$ alkyl with an attached phenyl group, $C_{1-10}$ alkyl with two attached phenyl groups, $C_{1-10}$ alkyl with an attached phenyl group substituted with K, $C_{1-10}$ alkyl with two attached phenyl groups substituted with K, $C_{1-10}$ alkyl with an attached phenoxy group, and $C_{1-10}$ alkyl with an attached phenoxy group substituted with K on the phenoxy group;

J is selected from the group consisting of halogen, COOH, OH, CN, $NO_2$, $NH_2$, $C_{1-10}$ alkoxy, $C_{1-10}$ alkylamine, $C_{2-12}$ dialkylamine, $C_{1-10}$ alkyl-$O-CO-$, $C_{1-10}$ alkyl-$O-CO-NH-$, and $C_{1-10}$ alkyl-$S-$;

K is selected from the group consisting of halogen, $C_{1-10}$ alkyl, $C_{1-10}$ perfluoroalkyl, $C_{1-10}$ alkoxy, $NO_2$, CN, OH, $CO_2H$, amino, $C_{1-10}$ alkylamino, $C_{2-12}$ dialkylamino, $C_{1-10}$ acyl, and $C_{1-10}$ alkoxy-$CO-$, and $C_{1-10}$ alkyl-$S-$;

$AA_1$ is a side chain blocked or unblocked amino acid with the L configuration, D configuration, or no chirality at the α-carbon selected from the group consisting of alanine, valine, leucine, isoleucine, proline, methionine, methionine sulfoxide, phenylalanine, tryptophan, serine, threonine, cysteine, tyrosine, asparagine, glutamine, aspartic acid, glutamic acid, lysine, arginine, histidine, phenylglycine, beta-alanine, norleucine, norvaline, α-aminobutyric acid, epsilon-aminocaproic acid, citrulline, hydroxyproline, ornithine, homoarginine, sarcosine, indoline 2-carboxylic acid, 2-azetidinecarboxylic acid, pipecolinic acid (2-piperidine carboxylic acid), O-methylserine, O-ethylserine, S-methylcysteine, S-ethylcysteine, S-benzylcysteine, $NH_2-CH(CH_2CHEt_2)-COOH$, α-aminoheptanoic acid, $NH_2-CH(CH_2-1-napthyl)-COOH$, $NH_2-CH(CH_2-2-napthyl)-COOH$, $NH_2-CH(CH_2-cyclohexyl)-COOH$, $NH_2-CH(CH_2-cyclopentyl)-COOH$, $NH_2-CH(CH_2-cyclobutyl)-COOH$, $NH_2-CH(CH_2-cyclopropyl)-COOH$, trifluoroleucine, and hexafluoroleucine;

$AA_2$ is a side chain blocked or unblocked amino acid with the L configuration, D configuration, or no chirality at the α-carbon selected from the group consisting of alanine, valine, leucine, isoleucine, proline, methionine, methionine sulfoxide, phenylalanine, tryptophan, glycine, serine, threonine, cysteine, tyrosine, asparagine, glutamine, aspartic acid, glutamic acid, lysine, arginine, histidine, phenylglycine, beta-alanine, norleucine, norvaline, α-aminobutyric acid, epsilon-aminocaproic acid, citrulline, hydroxyproline, ornithine, homoarginine, sarcosine, indoline 2-carboxylic acid, 2-azetidinecarboxylic acid, pipecolinic acid (2-piperidine carboxylic acid), O-methylserine, O-ethylserine, S-methylcysteine, S-ethylcysteine, S-benzylcysteine, $NH_2-CH(CH_2CHEt_2)-COOH$, α-aminoheptanoic acid, $NH_2-CH(CH_2-1-napthyl)-COOH$, $NH_2-CH(CH_2-2-napthyl)-COOH$, $NH_2-CH(CH_2-cyclohexyl)-COOH$, $NH_2-CH(CH_2-cyclopentyl)-COOH$, $NH_2-CH(CH_2-cyclobutyl)-COOH$, $NH_2-CH(CH_2-cyclopropyl)-COOH$, trifluoroleucine, and hexafluoroleucine;

$R_3$ and $R_4$ are selected independently from the group consisting of H, $C_{1-20}$ alkyl, $C_{1-20}$ cyclized alkyl, $C_{1-20}$ alkyl with a phenyl group attached to the $C_{1-20}$ alkyl, $C_{1-20}$ cyclized alkyl with an attached phenyl group, $C_{1-20}$ alkyl with an attached phenyl group substituted with K, $C_{1-20}$ alkyl with an attached phenyl group disubstituted with K, $C_{1-20}$ alkyl with an attached phenyl group trisubstituted with K, $C_{1-20}$ cyclized alkyl with an attached phenyl group substituted with K, $C_{1-10}$ alkyl with a morpholine $[-N(CH_2CH_2)O]$ ring attached through nitrogen to the alkyl, $C_{1-10}$ alkyl with a piperidine ring attached through nitrogen to the alkyl, $C_{1-10}$ alkyl with a pyrrolidine ring attached through nitrogen to the alkyl, $C_{1-20}$ alkyl with an OH group attached to the alkyl, $-CH_2CH_2OCH_2CH_2OH$, $C_{1-10}$ with an attached 4-pyridyl group, $C_{1-10}$ with an attached 3-pyridyl group, $C_{1-10}$ with an attached 2-pyridyl group, $C_{1-10}$ with an attached cyclohexyl group, $-NH-CH_2CH_2-(4-hydroxyphenyl)$, and $-NH-CH_2CH_2-(3-indolyl)$.

The Tripeptide α-Ketoamides have the following structural formula:

or a pharmaceutically acceptable salt, wherein $M_1$ represents H, $NH_2-CO-$, $NH_2-CS-$, $NH_2-SO_2-$, $X-NH-CO-$, $X_2N-CO-$, $X-N-CS-$, $X_2N-CS-$, $X-NH-SO_2-$, $X_2N-SO_2-$, $X-CO-$, $X-CS-$, $X-SO_2-$, $X-O-CO-$, or $X-O-CS-$;

X is selected from the group consisting of $C_{1-10}$ alkyl, $C_{1-10}$ fluoroalkyl, $C_{1-10}$ alkyl substituted with J, $C_{1-10}$ fluoroalkyl substituted with J, 1-admantyl, 9-fluorenyl, phenyl, phenyl substituted with K, phenyl disubstituted with K, phenyl trisubstituted with K, naphthyl, naphthyl substituted with K, naphthyl disubstituted with K, naphthyl trisubstituted with K, $C_{1-10}$ alkyl with an attached phenyl group, $C_{1-10}$ alkyl with two attached phenyl groups, $C_{1-10}$ alkyl with an attached phenyl group substituted with K, $C_{1-10}$ alkyl with two attached phenyl groups substituted with K, $C_{1-10}$ alkyl with an attached phenoxy group, and $C_{1-10}$ alkyl with an attached phenoxy group substituted with K on the phenoxy group;

J is selected from the group consisting of halogen, COOH, OH, CN, $NO_2$, $NH_2$, $C_{1-10}$ alkoxy, $C_{1-10}$ alkylamine, $C_{2-12}$ dialkylamine, $C_{1-10}$ alkyl-$O-CO-$, $C_{1-10}$ alkyl-$O-CO-NH-$, and $C_{1-10}$ alkyl-$S-$;

K is selected from the group consisting of halogen, $C_{1-10}$ alkyl, $C_{1-10}$ perfluoroalkyl, $C_{1-10}$ alkoxy, $NO_2$, CN, OH, $CO_2H$, amino, $C_{1-10}$ alkylamino, $C_{2-12}$ dialkylamino, $C_{1-10}$ acyl, and $C_{1-10}$ alkoxy-CO—, and $C_{1-10}$ alkyl-S—;

AA is a side chain blocked or unblocked amino acid with the L configuration, D configuration, or no chirality at the α-carbon selected from the group consisting of alanine, valine, leucine, isoleucine, proline, methionine, methionine sulfoxide, phenylalanine, tryptophan, glycine, serine, threonine, cysteine, tyrosine, asparagine, glutamine, aspartic acid, glutamic acid, lysine, arginine, histidine, phenylglycine, beta-alanine, norleucine, norvaline, α-aminobutyric acid, epsilon-aminocaproic acid, citrulline, hydroxyproline, ornithine, homoarginine, sarcosine, indoline 2-carboxylic acid, 2-azetidinecarboxylic acid, pipecolinic acid (2-piperidine carboxylic acid), O-methylserine, O-ethylserine, S-methylcysteine, S-ethylcysteine, S-benzylcysteine, $NH_2$—$CH(CH_2CHEt_2)$-COOH, α-aminoheptanoic acid, $NH_2$—$CH(CH_2$-1-napthyl)-COOH, $NH_2$—$CH(CH_2$-2-napthyl)-COOH, $NH_2$—$CH(CH_2$-cyclohexyl)-COOH, $NH_2$—$CH(CH_2$-cyclopentyl)-COOH, $NH_2$—$CH(CH_2$-cyclobutyl)-COOH, $NH_2$—$CH(CH_2$-cyclopropyl)-COOH, trifluoroleucine, and hexafluoroleucine;

$R_3$ and $R_4$ are selected independently from the group consisting of H, $C_{1-20}$ alkyl, $C_{1-20}$ cyclized alkyl, $C_{1-20}$ alkyl with a phenyl group attached to the $C_{1-20}$ alkyl, $C_{1-20}$ cyclized alkyl with an attached phenyl group, $C_{1-20}$ alkyl with an attached phenyl group substituted with K, $C_{1-20}$ alkyl with an attached phenyl group disubstituted with K, $C_{1-20}$ alkyl with an attached phenyl group trisubstituted with K, $C_{1-20}$ cyclized alkyl with an attached phenyl group substituted with K, $C_{1-10}$ alkyl with a morpholine [—$N(CH_2CH_2)O$] ring attached through nitrogen to the alkyl, $C_{1-10}$ alkyl with a piperidine ring attached through nitrogen to the alkyl, $C_{1-10}$ alkyl with a pyrrolidine ring attached through nitrogen to the alkyl, $C_{1-20}$ alkyl with an OH group attached to the alkyl, —$CH_2CH_2OCH_2CH_2OH$, $C_{1-10}$ with an attached 4-pyridyl group, $C_{1-10}$ with an attached 3-pyridyl group, $C_{1-10}$ with an attached 2-pyridyl group, $C_{1-10}$ with an attached cyclohexyl group, —NH—$CH_2CH_2$-(4-hydroxyphenyl), and —NH—$CH_2CH_2$-(3-indolyl).

The Tetrapeptide α-Ketoamides have the following structural formula:

or a pharmaceutically acceptable salt, wherein
$M_1$ represents H, $NH_2$—CO—, $NH_2$—CS—, $NH_2$—$SO_2$—, X—NH—CO—, $X_2N$—CO—, X—NH—CS—, $X_2N$—CS—, X—NH—$SO_2$—, $X_2N$—$SO_2$—, X—CO—, X—CS—, X—$SO_2$—, X—O—CO—, or X—O—CS—;

X is selected from the group consisting of $C_{1-10}$ alkyl, $C_{1-10}$ fluoroalkyl, $C_{1-10}$ alkyl substituted with J, $C_{1-10}$ fluoroalkyl substituted with J, 1-admantyl, 9-fluorenyl, phenyl, phenyl substituted with K, phenyl disubstituted with K, phenyl trisubstituted with K, naphthyl, naphthyl substituted with K, naphthyl disubstituted with K, naphthyl trisubstituted with K, $C_{1-10}$ alkyl with an attached phenyl group, $C_{1-10}$ alkyl with two attached phenyl groups, $C_{1-10}$ alkyl with an attached phenyl group substituted with K, $C_{1-10}$ alkyl with two attached phenyl groups substituted with K, $C_{1-10}$ alkyl with an attached phenoxy group, and $C_{1-10}$ alkyl with an attached phenoxy group substituted with K on the phenoxy group;

J is selected from the group consisting of halogen, COOH, OH, CN, $NO_2$, $NH_2$, $C_{1-10}$ alkoxy, $C_{1-10}$ alkylamine, $C_{2-12}$ dialkylamine, $C_{1-10}$ alkyl-O—CO—, $C_{1-10}$ alkyl-O—CO—NH—, and $C_{1-10}$ alkyl-S—;

K is selected from the group consisting of halogen, $C_{1-10}$ alkyl, $C_{1-10}$ perfluoroalkyl, $C_{1-10}$ alkoxy, $NO_2$, CN, OH, $CO_2H$, amino, $C_{1-10}$ alkylamino, $C_{2-12}$ dialkylamino, $C_1$-$C_{10}$ acyl, and $C_{1-10}$ alkoxy-CO—, and $C_{1-10}$ alkyl-S—;

AA is a side chain blocked or unblocked amino acid with the L configuration, D configuration, or no chirality at the α-carbon selected from the group consisting of alanine, valine, leucine, isoleucine, proline, methionine, methionine sulfoxide, phenylalanine, tryptophan, glycine, serine, threonine, cysteine, tyrosine, asparagine, glutamine, aspartic acid, glutamic acid, lysine, arginine, histidine, phenylglycine, beta-alanine, norleucine, norvaline, α-aminobutyric acid, epsilon-aminocaproic acid, citrulline, hydroxyproline, ornithine, homoarginine, sarcosine, indoline 2-carboxylic acid, 2-azetidinecarboxylic acid, pipecolinic acid (2-piperidine carboxylic acid), O-methylserine, O-ethylserine, S-methylcysteine, S-ethylcysteine, S-benzylcysteine, $NH_2$—$CH(CH_2CHEt_2)$-COOH, α-aminoheptanoic acid, $NH_2$—$CH(CH_2$-1-napthyl)-COOH, $NH_2$—$CH(CH_2$-2-napthyl)-COOH, $NH_2$—$CH(CH_2$-cyclohexyl)-COOH, $NH_2$—$CH(CH_2$-cyclopentyl)-COOH, $NH_2$—$CH(CH_2$-cyclobutyl)-COOH, $NH_2$—$CH(CH_2$-cyclopropyl)-COOH, trifluoroleucine, and hexafluoroleucine;

$R_3$ and $R_4$ are selected independently from the group consisting of H, $C_{1-20}$ alkyl, $C_{1-20}$ cyclized alkyl, $C_{1-20}$ alkyl with a phenyl group attached to the $C_{1-20}$ alkyl, $C_{1-20}$ cyclized alkyl with an attached phenyl group, $C_{1-20}$ alkyl with an attached phenyl group substituted with K, $C_{1-20}$ alkyl with an attached phenyl group disubstituted with K, $C_{1-20}$ alkyl with an attached phenyl group trisubstituted with K, $C_{1-20}$ cyclized alkyl with an attached phenyl group substituted with K, $C_{1-10}$ alkyl with a morpholine [—$N(CH_2CH_2)O$] ring attached through nitrogen to the alkyl, $C_{1-10}$ alkyl with a piperidine ring attached through nitrogen to the alkyl, $C_{1-10}$ alkyl with a pyrrolidine ring attached through nitrogen to the alkyl, $C_{1-20}$ alkyl with an OH group attached to the alkyl, —$CH_2CH_2OCH_2CH_2OH$, $C_{1-10}$ with an attached 4-pyridyl group, $C_{1-10}$ with an attached 3-pyridyl group, $C_{1-10}$ with an attached 2-pyridyl group, $C_{1-10}$ with an attached cyclohexyl group, —NH—$CH_2CH_2$-(4-hydroxyphenyl), and —NH—$CH_2CH_2$-(3-indolyl).

The Amino Acid α-Ketoamides have the following structural formula:

or a pharmaceutically acceptable salt, wherein $M_1$ represents H, $NH_2-CO-$, $NH_2-CS-$, $NH_2-SO_2-$, $X-NH-CO-$, $X_2N-CO-$, $X-NH-CS-$, $X_2N-CS-$, $X-NH-SO_2-$, $X_2N-SO_2-$, $X-CO-$, $X-CS-$, $X-SO_2-$, $X-O-CO-$, or $X-O-CS-$;

X is selected from the group consisting of $C_{1-10}$ alkyl, $C_{1-10}$ fluoroalkyl, $C_{1-10}$ alkyl substituted with J, $C_{1-10}$ fluoroalkyl substituted with J, 1-admantyl, 9-fluorenyl, phenyl, phenyl substituted with K, phenyl disubstituted with K, phenyl trisubstituted with K, naphthyl, naphthyl substituted with K, naphthyl disubstituted with K, naphthyl trisubstituted with K, $C_{1-10}$ alkyl with an attached phenyl group, $C_{1-10}$ alkyl with two attached phenyl groups, $C_{1-10}$ alkyl with an attached phenyl group substituted with K, $C_{1-10}$ alkyl with two attached phenyl groups substituted with K, $C_{1-10}$ alkyl with an attached phenoxy group, and $C_{1-10}$ alkyl with an attached phenoxy group substituted with K on the phenoxy group;

J is selected from the group consisting of halogen, COOH, OH, CN, $NO_2$, $NH_2$, $C_{1-10}$ alkoxy, $C_{1-10}$ alkylamine, $C_{2-12}$ dialkylamine, $C_{1-10}$ alkyl-$O-CO-$, $C_{1-10}$ alkyl-$O-CO-NH-$, and $C_{1-10}$ alkyl-S—;

K is selected from the group consisting of halogen, $C_{1-10}$ alkyl, $C_{1-10}$ perfluoroalkyl, $C_{1-10}$ alkoxy, $NO_2$, CN, OH, $CO_2H$, amino, $C_{1-10}$ alkylamino, $C_{2-12}$ dialkylamino, $C_{1-10}$ acyl, and $C_{1-10}$ alkoxy-$CO-$, and $C_{1-10}$ alkyl-S—;

AA is a side chain blocked or unblocked amino acid with the L configuration, D configuration, or no chirality at the $\alpha$-carbon selected from the group consisting of alanine, valine, leucine, isoleucine, proline, methionine, methionine sulfoxide, phenylalanine, tryptophan, glycine, serine, threonine, cysteine, tyrosine, asparagine, glutamine, aspartic acid, glutamic acid, lysine, arginine, histidine, phenylglycine, beta-alanine, norleucine, norvaline, $\alpha$-aminobutyric acid, epsilon-aminocaproic acid, citrulline, hydroxyproline, ornithine, homoarginine, sarcosine, indoline 2-carboxylic acid, 2-azetidinecarboxylic acid, pipecolinic acid (2-piperidine carboxylic acid), O-methylserine, O-ethylserine, S-methylcysteine, S-ethylcysteine, S-benzylcysteine, $NH_2-CH(CH_2-CHEt_2)-COOH$, $\alpha$-aminoheptanoic acid, $NH_2-CH(CH_2-1-napthyl)-COOH$, $NH_2-CH(CH_2-2-napthyl)-COOH$, $NH_2-CH(CH_2-cyclohexyl)-COOH$, $NH_2-CH(CH_2-cyclopentyl)-COOH$, $NH_2-CH(CH_2-cyclobutyl)-COOH$, $NH_2-CH(CH_2-cyclopropyl)-COOH$, trifluoroleucine, and hexafluoroleucine;

$R_3$ and $R_4$ are selected independently from the group consisting of H, $C_{1-20}$ alkyl, $C_{1-20}$ cyclized alkyl, $C_{1-20}$ alkyl with a phenyl group attached to the $C_{1-20}$ alkyl, $C_{1-20}$ cyclized alkyl with an attached phenyl group, $C_{1-20}$ alkyl with an attached phenyl group substituted with K, $C_{1-20}$ alkyl with an attached phenyl group disubstituted with K, $C_{1-20}$ alkyl with an attached phenyl group trisubstituted with K, $C_{1-20}$ cyclized alkyl with an attached phenyl group substituted with K, $C_{1-10}$ alkyl with a morpholine $[-N(CH_2CH_2)O]$ ring attached through nitrogen to the alkyl, $C_{1-10}$ alkyl with a piperidine ring attached through nitrogen to the alkyl, $C_{1-10}$ alkyl with a pyrrolidine ring attached through nitrogen to the alkyl, $C_{1-20}$ alkyl with an OH group attached to the alkyl, $-CH_2CH_2OCH_2CH_2OH$, $C_{1-10}$ with an attached 4-pyridyl group, $C_{1-10}$ with an attached 3-pyridyl group, $C_{1-10}$ with an attached 2-pyridyl group, $C_{1-10}$ with an attached cyclohexyl group, $-NH-CH_2CH_2-(4-hydroxyphenyl)$, and $-NH-CH_2CH_2-(3-indolyl)$.

The Applicants are aware of only a single peptide ketoamide reported in the literature. This compound is Z-Phe-NHCH$_2$CO—CO—NH-Et (Z-Phe-Gly-CO—NH-Et). The compound is reported in Hu and Abeles [*Arch. Biochem. Biophys.*. 281, 271–274 (1990)] to be an inhibitor of papain and cathepsin B.

The following Peptide Ketoamide compounds are representative of the Peptide Keto-Compounds found to be useful as Calpain inhibitors within the context of the present invention:

Z-Leu-Phe-CONH-Et
Z-Leu-Phe-CONH-nPr
Z-Leu-Phe-CONH-nBu
Z-Leu-Phe-CONH-iBu
Z-Leu-Phe-CONH-Bzl
Z-Leu-Phe-CONH—$(CH_2)_2$Ph
Z-Leu-Abu-CONH-Et
Z-Leu-Abu-CONH-nPr
Z-Leu-Abu-CONH-nBu
Z-Leu-Abu-CONH-iBu
Z-Leu-Abu-CONH-Bzl
Z-Leu-Abu-CO NH—$(CH_2)_2$Ph
Z-Leu-Abu-CO NH—$(CH_2)_3$—$N(CH_2CH_2)_2$O
Z-Leu-Abu-CONH—$(CH_2)_7CH_3$
Z-Leu-Abu-CONH—$(CH_2)_2$OH
Z-Leu-Abu-CONH—$(CH_2)_2O(CH_2)_2$OH
Z-Leu-Abu-CONH—$(CH_2)_{17}CH_3$
Z-Leu-Abu-CONH—$CH_2$—$C_6H_3(OCH_3)_2$
Z-Leu-Abu-CONH—$CH_2$—$C_4H_4N$

We studied the inhibition mechanism of the Peptide Keto-Compounds in both serine and thiol proteases. A crystal structure of one $\alpha$-ketoester bound into the active site of the serine protease, porcine pancreatic elastase, has been completed. The active site Ser-195 oxygen of the enzyme adds to the carbonyl group of the ketoester to form a tetrahedral intermediate which is stabilized by interactions with the oxyanion hole. This structure resembles the tetrahedral intermediate involved in peptide bond hydrolysis and proves that $\alpha$-ketoesters are transition-state analogs. His-57 is hydrogen bonded to the carbonyl group of the ester functional group, the peptide backbone on a section of the polypeptide backbone hydrogen bonds to the inhibitor to form a $\beta$-sheet, and the benzyl ester is directed toward the S' subsites. The side chain of the P1 amino acid residue is located in the S1 pocket of the enzyme. Interactions with ketoamides would be similar except that there is the possibility of forming an additional hydrogen bond with the NH group of the ketoamide functional group.

In the case of ketoacids, there would be no R group to interact with the S' subsites. Therefore, these inhibitors would be expected to be slightly less potent than the ketoesters and ketoamides. However, unexpectedly, certain ketoacid compounds have been found to have surprisingly high activity when used in the context of the present invention. In particular, Z-Leu-Phe-COOH and Z-Leu-Abu-COOH have been found to be extremely potent inhibitors of Calpains.

The active site of cysteine proteases shares several features in common with serine proteases including an active site histidine residue. In place of the Ser-195, cysteine proteases have an active site cysteine residue which would add to the ketonic carbonyl group of the peptide ketoacids, ketoesters, or ketoamides to form an adduct very similar to the structure described above except with a cysteine residue replacing the serine-195 residue. Additional interactions would occur between the extended substrate binding site of the cysteine protease and the inhibitor that would increase the binding affinity and specificity of the inhibitors.

The Peptide Keto-Compounds bind to the proteases inhibited thereby using many of the interactions that are found in complexes of a particular individual enzyme with its substrates. In order to design an inhibitor for a particular cysteine protease, it is necessary to: 1) find the amino acid sequences of good peptide substrates for that enzyme, and 2) place those or similar amino acid sequences into a Peptide Keto-Compound. This design strategy will also work when other classes of peptide inhibitors are used in place of the peptide substrate to gain information on the appropriate sequence to place in the Peptide Keto-Compound inhibitor. Thus, we are able to predict the structure of new inhibitors for other proteases based on knowledge of their substrate specificities. Once a good inhibitor structure for a particular enzyme is found, it is then possible to change other characteristics such as solubility or hydrophobicity by adding substituents to the M or R groups.

In the case of Calpain, a known inhibitor sequence is the peptide aldehyde, Ac-Leu-Leu-Nle-H (also known as Calpain Inhibitor 1 and hereinafter designated as "CI1"). This inhibitor, in addition to a related peptide aldehyde inhibitor Ac-Leu-Leu-Nme-H (also known as Calpain Inhibitor II) are commercially available from Calbiochem of La Jolla, Calif. We have discovered that peptide α-ketoesters with aromatic amino acid residues in P1 are good inhibitors of the thiol proteases, cathepsin B, papain and Calpain. Additionally, we have discovered that peptide α-ketoester and peptide α-ketoamides with either aromatic amino acid residues or small hydrophobic alkyl amino acid residues at P1 are good inhibitors of Calpain.

Our discovery of Peptide Keto-Compounds effective as Calpain Inhibitors was made through assay of the Peptide Keto-Compounds as reversible inhibitors. Various concentrations of inhibitors in dimethylsulfoxide (DMSO) were added to the assay mixture, which contained buffer and substrate. The reaction was started by the addition of the enzyme and the hydrolysis rates were followed spectrophotometrically or fluorimetrically. 88 mM $KH_2PO_4$, 12 mM $Na_2HPO_4$, 1.33 mM EDTA, 2.7 mM cysteine, pH 6.0 was used as a buffer for cathepsin B; and 20 mM Hepes, 10 mM $CaCl_2$, 10 mM β-mercaptoethanol, pH 7.2 buffer was utilized for calpain I and calpain II.

All peptide thioester hydrolysis rates were measured with assay mixtures containing 4,4'-dithiodipyridine [e324=19800 M−1 cm−1; Grasetti & Murray, Arch. Biochem. Biophys. 119, pp 41–49 (1967)]. Papain was assayed with Bz-Arg-AMC or Bz-Arg-NA [Kanaoka et al., Chem. Pharm. Bull. 25, 3126–3128 (1977)], and the AMC (7-amino-4-methylcoumarin) release was followed fluorimetrically (excitation at 380 nm, and emission at 460 nm). Cathepsin B was assayed with Z-Arg-Arg-AFC [Barrett and Kirschke, Methods Enzymol. 80, 535–561 (1981)], and the AFC (7-amino-4-trifluoromethylcoumarin) release was followed fluorimetrically (excitation at 400 nm, and emission at 505 nm). Calpain I from human erythrocytes and calpain II from rabbit were assayed using Suc-Leu-Tyr-AMC [Sasaki et al., J. Biol. Chem. 259, 12489–12494 (1984), hereby incorporated by reference], and the AMC (7-amino-4-methylcoumarin) release was followed fluorimetrically (excitation at 380 nm, and emission at 460 nm). Enzymatic hydrolysis rates were measured at various substrate and inhibitor concentrations, and $K_i$ values were determined by Dixon plot.

Table PKC1 shows the inhibition constants ($K_i$) for papain, cathepsin B, calpain I, and calpain II.

The inhibition constants for papain shown in Table PKC1 were measured in 0.05M Tris-HCl, pH 7.5 buffer, containing 2 mM EDTA, 5 mM cysteine (freshly prepared), 1% DMSO, at 25° C., using $N^\alpha$-Benzoyl-Arg-AMC as a substrate, except that those values of inhibition constants for papain marked with an "e" in Table PKC1 were measured in 50 mM Tris-HCl, pH 7.5 buffer, containing 20 mM EDTA, 5 mM cysteine, 9% DMSO, at 25° C., using $N^\alpha$-Benzoyl-Arg-NA as a substrate.

TABLE PKC1
Inhibition of Cysteine Proteases by Peptide Ketoesters and Ketoacids

| Compounds | $K_i$(mM) | | | |
|---|---|---|---|---|
| | P[a] | CB[b] | CI[c] | CII[d] |
| Z-Leu-Abu-COOEt | | | 0.04 | 0.4 |
| Z-Leu-Phe-COOEt | | | 0.23 | 0.4 |
| Z-Leu-Nle-COOEt | | | 0.12 | 0.18 |
| Z-Leu-Nva-COOEt | | 30 | | 1.2 |
| Bz-DL-Phe-COOEt | 500[e] | 64 | | |
| Z-Phe-DL-Phe-COOEt | 1.8 | 0.1 | | |
| Z-Phe-DL-Ala-COOEt | 3.6 | 3.2 | | |
| Z-Ala-Ala-DL-Ala-COOEt | 1.5 | 2.2 | 200 | |
| Z-Ala-Ala-DL-Abu-COOEt | 0.9 | 10 | 50 | 200 |
| Z-Ala-Ala-DL-Abu-COOBzl | 30 | 60 | | |
| Z-Ala-Ala-DL-Nva-COOEt | 30 | 0.1 | | |
| Z-Ala-Pro-DL-Ala-COOEt | 26 | 66 | | |
| MeO-Suc-Val-Pro-DL-Phe-COOMe | 1.1 2.9[e] | 0.1 | | |
| Z-Ala-Ala-Ala-DL-Ala-COOEt | 2.1 | 10.0 | | |
| MeO-Suc-Ala-Ala-Pro-Abu-COOMe | 0.7 | 6.0 | 100 | |

[a]P = Papain
[b]CB = Cathepsin B
[c]CI = Calpain I
[d]CII = Calpain II

It can be seen from the data in Table PKC1 that the dipeptide ketoesters with Abu, Phe, or Nle in the P1 site and Leu in the P2 site are potent inhibitors of calpain I and calpain II. Tripeptides with Abu or Ala in the P1 site and Ala in the P2 site are also seen to be inhibitors of Calpain, albeit somewhat weaker inhibitors than the dipeptides. Thus, in accordance with the foregoing description of the design of Peptide Keto-Compound inhibitors, we believe that Peptide Keto-Compounds based on these and similar structures will exhibit Calpain inhibitory activity.

The peptide α-ketoesters are prepared by a two step Dakin-West procedure. This procedure can be utilized with either amino acid derivatives, dipeptide derivatives, tripeptide derivatives, or tetrapeptide derivatives as shown in the following scheme:

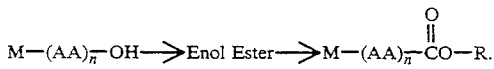

The precursor peptide $((AA)_n)$ can be prepared using standard peptide chemistry procedures, including those that are well described in publications such as The Peptides, Analysis, Synthesis, Biology, Vol. 1-9, published in 1979-1987 by Academic Press ("The Peptides") and Houben-Weyl Methoden der Organischen Chemie, Vol. 15, Parts 1 and 2, Synthese von Peptiden, published by Georg Thieme Verlag, Stuttgart in 1974 ("Houben-Weyl") (both references hereby incorporated herein by reference).

The M group can be introduced using a number of different reaction schemes. For example, it could be introduced directly on an amino acid as shown in the following scheme:

Alternatively, the M group can be introduced by reaction with an amino acid ester, followed by removal of the ester group to give the same product, as shown in the following scheme:

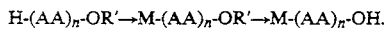

These and other techniques for introduction of the M group are well documented in the The Peptides, Houben-Weyl, and many other textbooks on organic synthesis. For example reaction with cyanate or p-nitrophenyl cyanate would introduce a carbamyl group ($M=NH_2CO—$). Reaction with p-nitrophenyl thiocarbamate would introduce a thio carbamyl group ($M=NH_2CS—$). Reaction with $NH_2S_4O_2Cl$ would introduce the $NH_2SO_2—$ group. Reaction with a substituted alkyl or aryl isocyanate would introduce the $X—NH—CO—$ group where X is a substituted alkyl or aryl group. Reaction with a substituted alkyl or aryl isothiocyanate would introduce the $X—NH—CS—$ group where X is a substituted alkyl or aryl group. Reaction with $X—SO_2—Cl$ would introduce the $X—SO_2—$ group. Reaction with a substituted alkyl or aryl acid chloride would introduce an acyl group ($M=Y—CO—$). For example, reaction with $MeO—CO—CH_2CH_2—CO—Cl$ would give the $Y—CO—$ group when Y is a C2 alkyl substituted with a C1 alkyl-OCO— group. Reaction with a substituted alkyl or aryl thioacid chloride would introduce a thioacyl group ($M=Y—CS—$). Reaction with an a substituted alkyl or aryl sulfonyl chloride would introduce an $X—SO2—$ group. For example reaction with dansyl chloride would give the $X—SO2—$ derivative where X was a napthyl group monosubstituted with a dimethylamino group. Reaction with a substituted alkyl or aryl chloroformate would introduce a $X—O—CO—$ group. Reaction with a substituted alkyl or aryl chlorothioformate would introduce a $X—O—CS—$. There are many alternate reaction schemes which could be used to introduce all of the above M groups to give either M-AA-OH or M-AA-OR'. The M-AA-OH derivatives could then be used directly in the Dakin-West reaction or could be converted into the dipeptides, tripeptides, and tetrapeptides M-AA-AA-OH, M-AA-AA-AA-OH, or M-AA-AA-AA-AA-OH which could be be used in the Dakin-West reaction. The substituted peptides M-AA-AA-OH, M-AA-AA-AA-OH, or M-AA-AA-AA-AA-OH could also be prepared directly from H-AA-AA-OH, H-AA-AA-AA-OH, or H-AA-AA-AA-AA-OH using the reactions described above for introduction of the M group. Alternately, the M group could be introduced by reaction with carboxyl blocked peptides M-AA-AA-OR', M-AA-AA-AA-OR', or M-AA-AA-AA-AA-OR', followed by the removal of the blocking group R'.

The R group in the ketoester structures is introduced during the Dakin-West reaction by reaction with an oxalyl chloride $Cl—CO—CO—O—R$. For example, reaction of M-AA-AA-OH with ethyl oxalyl chloride $Cl—CO—CO—O-Et$ gives the keto ester M-AA-AA—CO—O-Et. Reaction of M-AA-AA-AA-AA-OH with $Cl—CO—CO—O-Bzl$ would give the ketoester M-AA-AA-AA-AA-CO—O-Bzl. Clearly a wide variety of R groups can be introduced into the ketoester structure by reaction with various alkyl or arylalkyl oxalyl chlorides ($Cl—CO—CO—O—R$).

The oxalyl chlorides are easily prepared by reaction of an alkyl or arylalkyl alcohol with oxalyl chloride $Cl—CO—CO—Cl$. For example, Bzl-O—CO—CO—Cl and n-Bu-O—CO—CO—Cl are prepared by reaction of benzyl alcohol and butanol, respectively, with oxalyl chloride in yields of 50% and 80% [Warren, C. B., and Malee, E. J., *J. Chromatography* 64, 219-222 (1972); incorporated herein by reference].

Ketoacids M-AA-CO—OH, M-AA-AA-CO—OH, M-AA-AA-AA-CO—OH, M-AA-AA-AA-AA-CO—OH, are generally prepared from the corresponding ketoesters M-AA-CO—OR, M-AA-AA-CO—OR, M-AA-AA-AA-CO—OR, M-AA-AA-AA-AA-CO—OR by alkaline hydrolysis. In some cases, it may be necessary to use other methods such as hydrogenolysis of a benzyl group ($R=Bzl$) or acid cleavage ($R=t$-butyl) to obtain the ketoacid. The alternate methods would be used when the M group was labile to alkaline hydrolysis.

The various peptide ketoamide subclasses (M-AA-NH—$CHR_2$—CO—CO—$NR_3R_4$ (Dipeptide Ketoamides (Subclass A)), M-AA-AA-CO—$NR_3R_4$ (Dipeptide Ketoamides (Subclass B)), M-AA-AA-AA-CO—$NR_3R_4$ (Tripeptide Ketoamides), M-AA-AA-AA-AA-CO—$NR_3R_4$ (tetrapeptide ketoamides) and $M_1$-AA-CO—$NR_3R_4$ (Amino Acid Ketoamides)) were prepared indirectly from the corresponding ketoesters. The ketone carbonyl group was first protected as shown in the following scheme and then the ketoamide was prepared by reaction with an amine H—$NR_3R_4$. The illustrated procedure should also work with other protecting groups.

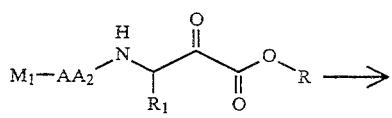

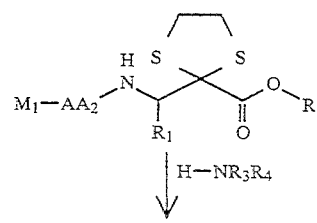

-continued

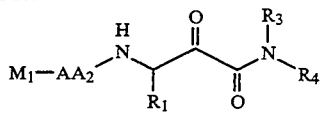

In addition to the scheme outlined above, a ketoacid could be used as a precursor to produce a corresponding ketoamide. Blocking the ketone carbonyl group of the ketoacid and then coupling with an amine H—NR$_3$R$_4$ using standard peptide coupling reagents would yield an intermediate which could then be deblocked to form the ketoamide.

General Synthetic Methods for Peptide Keto-Compounds

Unless otherwise noted, materials were obtained from commercial suppliers and used without further purification. Melting points were taken with a Büchi capillary apparatus and are uncorrected. $^1$H NMR spectra were determined on a Varian Gemini 300. Chemical shifts are expressed in ppm (δ) relative to internal tetramethylsilane. Flash column chromatography was performed with Universal Scientific Inc. silica gel 0-63. Electron-impact mass spectra (MS) of novel compounds were determined with a Varian MAT 112S spectrometer. The purity of all compounds was checked by thin-layer chromatography on Baker Si250F silica gel plates using the following solvent system: A, CHCl$_3$:MeOH=20:1 v/v; B, CHCl$_3$:MeOH=100:1 v/v; C, AcOEt; D, CHCl$_3$:MeOH=10:1 v/v; E, n-BuOH:AcOH:py:H$_2$O=4:1:1:2 v/v; F, CHCl$_3$:MeOH=5:1 v/v; G, AcOEt:MeOH=10:1 v/v; H, (i-Pr)$_2$O; I, CHCl$_3$:MeOH:AcOH=80:10:5 v/v; J, CHCl$_3$:MeOH:AcOH=95:5:3 v/v; K, AcOEt:AcOH=200:1 v/v; L, CHCl$_3$; M, CHCl$_3$:MeOH=50:1 v/v Amino acid methyl ester hydrochlorides were prepared according to M. Brenner et al.[*Helv. Chem. Acta* 33, 568 (1950); 36, 1109 (1953)] in a scale over 10 mmol or according to Rachele [*J. Org. Chem.* 28, 2898 (1963)] in a scale of 0.1–1.0 mmol.

|  | Yield (%) | mp (°C.) | m.p. (literature) |
|---|---|---|---|
| DL-Nva-OCH$_3$.HCl, | 100 | 113–116 | 116–117 |
| L-Ile-OCH$_3$.HCl, | 98 | 90–91 | 98–100 |
| L-Phe-OCH$_3$.HCl, | 98 | 159–161 | 158–160 |
| DL-Abu-OCH$_3$.HCl, | 100 | 148–150 | 150–151 |
| L-Leu-OCH$_3$.HCl | 100 | 145.5–146.5 | 147 |
| DL-Nle-OCH$_3$.HCl | 93 | 120–121 | 122–123 |
| 4-Cl-Phe-OCH$_3$.HCl | 98 | 184–185 (decomp.) | 185–186 |

N-Acylamino acids was synthesized via Schotten-Baumann reaction [M. Bergmann, L. Zervas, *Chem. Ber.* 65, 1192 (1932)] in the case when the acyl group was phenylsulphonyl, 2-naphthylsulphonyl or benzoyl.

|  | Yield (%) | mp (°C.) | TLC (R$_f$, eluent) |
|---|---|---|---|
| 2-NapSO$_2$-L-Leu-OH | 49 | 115–116 | 0.58I |
| 2-NapSO$_2$-DL-Abu-OH | 51 | 150–151 | 0.50I |
| 2-NapSO$_2$-L-Phe-OH | 57 | 148–148.5 | 0.48K |
| PheSO$_2$-DL-Abu-OH | 44 | 142–143 | 0.51K |
| PhCO-DL-Abu-OH | 64 | 141–142 | 0.64K |

N-Acylamino acids with 4-methylpentanoic, 2-(1-propyl)pentanoic and 7-phenylheptanoic group was synthesized in a two step synthesis. The N-acylamino acid methyl ester was obtained first and then was hydrolysed to the free N-acylamino acid.

N-Acylamino Acid Methyl Esters (General Procedure). To a chilled (10° C.) slurry of the appropriate amino acid methyl ester hydrochloride (20 mmol) in 100 ml benzene was added slowly (temp. 10°–15° C.) 40 mmol triethylamine or N-methylmorpholine and then the reaction mixture was stirred for 30 minutes at this temperature. Then 18 mmol of appropriate acid chloride (temp. 10°–15° C.) was added slowly to the reaction mixture and the reaction mixture was stirred overnight at room temperature. The precipitated hydrochloride was filtered, washed on a funnel with 2×20 ml benzene, and the collected filtrate was washed successively with 2×50 ml 1M HCl, 2×50 ml 5% NaHCO$_3$, 1×100 ml H$_2$O, 2×50 ml satd. NaCl and dried over MgSO$_4$. After evaporation of the solvent in vacuo (rotavaporator), the residue was checked for purity (TLC) and used for the next step (hydrolysis).

|  | Yield (%) | mp (°C.) |
|---|---|---|
| (CH$_3$)$_2$CH(CH$_2$)$_2$CO-DL-Abu-OCH$_3$ | 80 | oil |
| (CH$_3$CH$_2$CH$_2$)$_2$CHCO-DL-Abu-OCH$_3$ | 96 | 117–118 |
| Ph(CH$_2$)$_6$CO-DL-Abu-OCH$_3$ | 72 | oil |

Hydrolysis (General Procedure). To a solution of 10 mmole of the appropriate N-acylamino acid methyl ester in 100 ml of methanol was added in one portion 11.25 ml of 1M NaOH (11.25 mmol) and the reaction mixture was stirred three hours at room temperature. Then the reaction mixture was cooled to 0° C. (ice-salt bath) and acidified to pH=2 with 1M HCl aq. To this reaction mixture was added 100 ml ethyl acetate, transferred to a separatory funnel and organic layer separated. The water layer was saturated with solid NaCl or (NH$_4$)$_2$SO$_4$ and reextracted with 2×50 ml AcOEt. The collected organic layer was washed with 2×50 ml H$_2$O, decolorized with carbon, and dried over MgSO$_4$. After evaporation of the solvent in vacuo (rotavaporator), the residue was checked for purity (TLC) and in the case of contamination was crystallized from an appropriate solvent.

|  | Yield (%) | mp (°C.) |
|---|---|---|
| (CH$_3$)$_2$CH(CH$_2$)$_2$CO-DL-Abu-OH | 92 | 110.5–112 |
| (CH$_3$CH$_2$CH$_2$)$_2$CHCO-DL-Abu-OH | 99 | 126–127 (n-octane) |
| Ph(CH$_2$)$_6$CO-DL-Abu-OH | 89 | 110–112 (n-octane) |

N-Acyldipeptide methyl esters were synthesized via the HOBt-DCC method in a DMF solution [König and Geiger, *Chem. Ber.* 103, 788 (1970)].

|  | Yield (%) | mp (°C.) | TLC (R$_f$, eluent) |
|---|---|---|---|
| Z-Leu-DL-NVa-OCH$_3$ | 80 | 112–113 | 0.37 B |
| Z-Leu-L-Phe-OCH$_3$ | 83 | 86–87 | 0.85 A |
|  |  |  | 0.39 B |
| Z-Leu-L-Ile-OCH$_3$ | 97 | oil | 0.79 A |
|  |  |  | 0.43 B |
| Z-Leu-DL-Abu-OCH$_3$ | 99 | 86–88 | 0.33 B |
|  |  |  | 0.26 H |

-continued

| | Yield (%) | mp (°C.) | TLC (R_f, eluent) |
|---|---|---|---|
| Z-Leu-L-Leu-OCH$_3$ | 80 | 91–92 | 0.79 G |
| Z-Leu-DL-NLeu-OCH$_3$ | 97 | 111–111.5 | |
| Z-Leu-4-Cl-Phe-OCH$_3$ | 65 | 112–132 (liquid crystal?) | 0.77 J 0.68 K |
| 2-NapSO$_2$-Leu-DL-Abu-OCH$_3$ | 99 | oil | 0.59 A |
| 2-NapSO$_2$-Leu-L-Leu-OCH$_3$ | 90 | 97–98.5 | 0.63 A |

N-Acyldipeptides were obtained by hydrolysis of the appropriate methyl esters via a general hydrolysis procedure. In the case of N-sulphonyldipeptide methyl esters, 1 equivalent of the methyl ester was hydrolyzed with 2.25 equivalent of 1 molar NaOH because of form a sulfonamide sodium salt.

| | Yield (%) | mp (°C.) | TLC (R_f, eluent) |
|---|---|---|---|
| Z-Leu-DL-NVa-OH | 100 | 117–118.5 | 0.11 A |
| Z-Leu-L-Phe-OH | 92 | 105–106.5 | 0.28 C 0.55 G |
| Z-Leu-L-ILe-OH | 79 | 77–79 | 0.22 A 0.52 C |
| Z-Leu-DL-Abu-OH | 99 | glass | 0.61 G |
| Z-Leu-L-Leu-OH | 97 | glass | 0.56 I |
| Z-Leu-DL-NLeu-OH | 98 | 95–96 | |
| Z-Leu-4-Cl-Phe-OH | 87 | 104–114 (liquid crystal?) | 0.48 K |
| 2-NapSO$_2$-Leu-DL-Abu-OH | 97.4 | 180–195 (decomp) | 0.58 I |
| 2-NapSO$_2$-Leu-L-Leu-OH | 94.0 | 68–70 | 0.52 I |

N-Acytripeptide methyl esters were synthesized via HOBt-DCC method in DMF solution [König and Geiger, *Chem. Ber.* 103, 788 (1970)].

| | Yield (%) | mp (°C.) | TLC (R_f, eluent) |
|---|---|---|---|
| Z-Leu-Leu-Abu-OCH$_3$ | 87 | 140–141.5 | 0.50 A |
| Z-Leu-Leu-Phe-OCH$_3$ | 76 | 158–159 | 0.83 J |
| 2-NapSO$_2$-Leu-Leu-Abu-OCH$_3$ | 97 | >200 | 0.52 A |

N-Acyltripeptide were obtained through hydrolysis of the appropriate methyl esters via general hydrolysis procedure. In the case of N-sulphonyltripeptide methyl ester, 1 equivalent of methyl ester was hydrolyzed with 2.25 equivalent of 1 molar NaOH to form the sulfonamide sodium salt.

| | Yield | mp (°C.) | TLC (R_f, eluent) |
|---|---|---|---|
| Z-Leu-Leu-Abu-OH | 97 | glass | 0.69 I |
| Z-Leu-Leu-Phe-OH | 98 | glass | 0.44 K |
| 2-NapSO$_2$-Leu-Leu-Abu-OH | 85 | 193–195 (decomp.) | 0.53 I 0.32 J |

The following examples, Examples PKC1-PKC65, are given to illustrate the synthesis of Peptide Keto-Compounds:

EXAMPLE PKC1

Z-Ala-DL-Ala-COOEt. This compound was synthesized by a modified Dakin-West procedure [Charles et al., J. Chem. Soc. Perkin I, 1139–1146, (1980)]. To a stirred solution of Z-Ala-Ala-OH (880 mg, 3 mmole), 4-dimethylaminopyridine (15 mg, 0.31 mmole), and pyridine (0.8 mL, 10 mmole) in tetrahydrofuran (3 mL) was added ethyl oxalyl chloride (0.7 mL, 6 mmole) at a rate sufficient to initiate refluxing. The mixture was gently refluxed for 3.5 h. The mixture was treated with water (3 mL) and stirred vigorously at room temperature for 30 min. The mixture was extracted with ethyl acetate. The organic extracts were dried and evaporated to obtain the residue (1.45 g). The residue was chromatographed on silica gel and eluted with CH$_2$Cl$_2$ to give the enol ester product, oil (500 mg, 37%); single spot on tlc, R$_f^2$=0.67 (CHCl$_3$:MeOH=9:1); MS, m/e=451 (M$^+$ +1). To a stirred suspension of the enol ester (210 mg, 0.47 mmol) in anhydrous ethanol (1 mL) at room temperature was added dropwise a solution of sodium ethoxide in ethanol until a clear yellow solution resulted. The ethanol was then removed and the residue was treated with ether. The ether solution was washed with water, dried, and evaporated to give a residue. This residue was chromatographed on a silica gel and the product was eluted with methylene chloride. The solvent was removed, and the peptide ketoester Z-Ala-DL-Ala-CO$_2$Et was obtained as an semi-solid (150 mg, 92%); single spot on tlc, R$_f^1$ 0.58 (CHCl$_3$:MeOH=5:1); MS, m/e=351 (M$^+$ +1). Anal. Calcd. for C$_{17}$H$_{22}$O$_6$N$_2$.⅓ H$_2$O: C, 57.29; H, 6.22; N, 7.86. Found: C, 57.23; H, 6.36; N, 8.17.

EXAMPLE PKC2

Z-Ala-Ala-DL-Ala-CO$_2$Et. This compound was prepared from Z-Ala-Ala-Ala-OH using the same procedure as described in Example PKC1. The product was crystallized from ethyl ether in 23% yield; single spot on tlc, R$_f^2$=0.31 (CHCl$_3$:MeOH=9:1); mp 143°–144° C.; MS, m/e=421 (M$^+$). Anal. Calcd. for C$_{20}$H$_{27}$O$_7$N$_3$: C, 56.99; H, 6.46; N, 9.97. Found: C, 56.96; H, 6.49; N, 9.92.

EXAMPLE PKC3

Z-Ala-Ala-DL-Abu-CO$_2$Et. This compound was prepared from Z-Ala-Ala-DL-Abu-OH in 11% yield by the procedure described in Example PKC1; single spot on tlc, R$_f^2$ 0.60 (CHCl$_3$:MeOH=9:1); mp 111°–113° C.; MS, m/e=436 (M$^+$ +1). Anal. Calcd. for C$_{21}$H$_{29}$O$_7$N$_3$.⅓ H$_2$O: C, 57.13; H, 6.75; N, 9.51. Found: C, 57.38; H, 6.82; N, 9.62.

EXAMPLE PKC4

Z-Ala-Ala-DL-Nva-CO$_2$Et. This compound was prepared from Z-Ala-Nva-OH in 20% yield by the procedure described in Example PKC1; single spot on tlc, R$_f^1$=0.64 (CHCl$_3$:MeOH=5:1); MS, m/e=450 (M$^+$ +1). Anal. Calcd. for C$_{22}$H$_{31}$O$_7$N$_3$.H$_2$O: C, 56.51; H, 7.11; N, 8.99. Found: C, 56.42; H, 7.08; N, 9.06.

EXAMPLE PKC5

Z-Ala-Pro-DL-Ala-CO$_2$Et. This compound was prepared from Z-Ala-Pro-Ala-OH.dicyclohexylamine in 19% yield by the procedure described in Example PKC1; single spot on tlc, R$_f^2$=0.55 (CHCl$_3$:MeOH=9:1); MS, m/e=447 (M$^+$). Anal. Calcd. for C$_{22}$H$_{29}$O$_7$N$_3$.½ H$_2$O: C, 57.88; H, 6.62; N, 9.21. Found: C, 57.65; H, 6.68; N, 9.17.

EXAMPLE PKC6

Z-Ala-Ala-Ala-DL-Ala-CO$_2$Et. The compound was prepared from Z-Ala-Ala-Ala-Ala-OH in 7% yield by the procedure described in Example PKC1; single spot on tlc, $R_f^2=0.40$ (CHCl$_3$:MeOH=9:1); mp. 163°–165° C.; MS, m/e=493 (M$^+$+1). Anal. Calcd. for C$_{23}$H$_{32}$O$_8$N$_4$.½ H2O: C, 55.08; H, 6.63; N, 11.17. Found: C, 54.85; H, 6.53; N, 11.14.

EXAMPLE PKC7

Bz-DL-Phe-CO$_2$Et. This compound was prepared from Bz-Phe-OH in 36% yield by the procedure described in Example PKC1, oil, single spot on tlc, $R_f^2$0.61 (CHCl$_3$:MeOH=9:1); MS, m/e=325 (M$^+$). Anal. Calcd. for C$_{19}$H$_{19}$O$_4$N.⅓ H2O: C, 68.86; H, 5.98; N, 4.22. Found: C, 69.10; H, 6.09; N, 4.38.

EXAMPLE PKC8

MeO-Suc-Ala-DL-Ala-CO$_2$Me. This compound was prepared from MeO-Suc-Ala-Ala-OH in 22% yield by the same procedure as described in Example PKC1, except that sodium methoxide in methanol was used for enol ester hydrolysis, single spot on tlc, $R_f^2=0.43$ (CHCl$_3$:MeOH=9:1); MS, m/e=317 (M$^+$+1). Anal. Calcd. for C$_{13}$H$_{20}$O$_7$N$_4$.⅓ H2O: C, 48.44; H, 6.46; N, 8.69. Found: C, 48.56; H, 6.39; N, 8.69.

EXAMPLE PKC9

MeO-Suc-Ala-Ala-Pro-DL-Abu-CO$_2$Me. This compound was prepared from MeO-Suc-Ala-Ala-Pro-DL-Abu-OH in 22% yield by the procedure described in Example PKC8; foam, single spot on tlc, $R_f^4=0.66$ (CHCl$_3$:MeOH=5:1). Anal. Calcd. for C$_{22}$H$_{34}$O$_9$N$_4$.-H2O: C, 51.53; H, 7.02; N, 10.85. Found: C. 51.11; H, 7.03; N, 10.88.

EXAMPLE PKC10

MeO-Suc-Val-Pro-DL-Phe-CO$_2$Me. This compound was prepared from MeO-Suc-Val-Pro-Phe-OH in 42% yield by the same procedure as described in Example PKC8; foam, single spot on tic, $R_f^2$ 0.57 (CHCl$_3$:MeOH=9:1); MS, m/e=517 (M$^+$). Anal. Calcd. for C$_{26}$H$_{35}$O$_8$N$_3$.⅔ H2O: C, 58.96; H, 6.90; N, 7.93. Found: C, 58.92; H, 6.96; N, 7.89.

EXAMPLE PKC11

Bz-DL-Ala-CO$_2$-n-Bu. This compound was prepared from Bz-Ala-OH in 45% yield by the procedure described in Example PKC1, except that n-butyl oxalyl-chloride was used for the Dakin-West reaction and sodium n-butoxide in n-butanol was used for enol ester hydrolysis; colorless oil, single spot on tlc, $R_f^2=0.72$ (CHCl$_3$:MeOH=9:1); MS, m/e=277 (M$^+$).

EXAMPLE PKC12

Bz-DL-Ala-CO$_2$Bzl. This compound was prepared from Bz-Ala-OH in 26% yield by the procedure described in Example PKC1, except that benzyl oxalyl chloride was used in place of ethyl oxayl chloride and sodium benzyloxide in benzyl alcohol was used for enol ester hydrolysis; single spot on tlc, $R_f^2=0.69$ (CHCl$_3$:MeOH=9:1); mp 95°–97° C.; MS, m/e=312 (M$^+$+1). Anal. Calcd. for C$_{18}$H$_{17}$O$_4$N.⅓ H2O: C, 67.48; H, 5.66; N, 4.37. Found: C, 67.78; H, 5.55; N, 4.66.

EXAMPLE PKC13

Z-Ala-DL-Ala-CO$_2$-n-Bu. This compound was prepared from Z-Ala-Ala-OH in 14% yield by the procedure described in Example PKC1, except that n-butyl oxalyl chloride was used in the Dakin-West reaction and sodium n-butoxide was used for enol ester hydrolysis; oil, single spot on tlc, $R_f^2=0.45$ (CHCl$_3$:MeOH=9:1); MS, m/e=378 (M$^+$). Anal. Calcd. for C$_{19}$H$_{26}$O$_6$N$_2$.⅓ H2O: C, 59.35; H, 7.00; N, 7.29. Found: C, 59.41; H, 7.03; N, 7.10.

EXAMPLE PKC14

Z-Ala-DL-Ala-CO$_2$Bzl. This compound was prepared from Z-Ala-Ala-OH in 36% yield by the procedure described in Example PKC1, except that benzyl oxalyl chloride was used in the Dakin-West reaction and sodium benzyloxide in benzyl alcohol was used for enol ester hydrolysis; single spot on tlc, $R_f^2=0.55$ (CHCl$_3$:MeOH=9:1); MS, m/e=413 (M$^+$+1). Anal. Calcd. for C$_{22}$H$_{24}$O$_6$N$_2$: C, 64.06; H, 5.87; N, 6.79. Found: C, 63.79; H, 5.95; N, 6.72.

EXAMPLE PKC15

Z-Ala-Ala-DL-Abu-CO$_2$Bzl. This compound was prepared from Z-Ala-Ala-Abu-OH in 31% yield by the procedure described in Example PKC1, except that benzyl oxalyl chloride was used in the Dakin-West reaction and sodium benzyloxide in benzyl alcohol was used for enol ester hydrolysis; single spot on tlc, $R_f^2=0.40$ (CHCl$_3$:MeOH=9:1); mp 124°–125° C.; MS, m/e=498 (M$^+$+1). Anal. Calcd. for C$_{26}$H$_{31}$O$_7$N$_3$.⅔ H2O: C, 61.28; H, 6.39; N, 8.24. Found: C, 61.14; H, 6.65; N, 7.94.

EXAMPLE PKC16

Bz-DL-Ala-COOH. The hydrolysis procedure of Tsushima et al. [J. Org. Chem. 49, 1163–1169 (1984)] was used. Bz-DL-Ala-CO$_2$Et (540 mg, 2.2 mmol) was added to a solution of 650 mg of sodium bicarbonate in an aqueous 50% 2-propanol solution (7.5 mL of H$_2$O and 2-propanol) and stirred at 40° C. under nitrogen. After adding ethyl acetate and a saline solution to the reaction mixture, the aqueous layer was separated and acidified with 2N HCl and extracted with ethyl acetate. The organic layer was dried over magnesium sulfate and the solvent was removed under reduced pressure. The crude hydrolysis product was chromatographed on silica gel and eluted with methylene chloride and methanol to obtain an oil (150 mg, 31%); single spot on tlc, $R_f^4=0.68$ (n-butanol:acetic acid:pyridine:H$_2$O=4:1:1:2). Anal. Calcd. for C$_{11}$H$_{11}$O$_4$N.⅔ H2O: C, 56.28; H, 5.37; N, 5.97. Found: C, 56.21; H, 5.46; 5.66.

EXAMPLE PKC17

Z-Leu-DL-Nva-COOEt. This compound was prepared from Z-Leu-Nva-OH in 60% yield by the procedure described in Example PKC1; oil, one spot on tlc, $R_f=0.49$ (CHCl$_3$:MeOH=20:1). NMR (CDCl$_3$) δ: 0.91 (t, 9H), CH$_3$; 1.25 (t, 3H), CH$_3$; 1.38 (q, 2H), OCH$_2$CH$_3$; 1.64 (m, 6H), CH$_2$; 1.85 (m, 1H), CH(CH$_3$)$_2$; 4.34 (m, 1H) CH$_2$CH(NHCOOCH$_2$Ph)CONH; 5.12 (d, 3H) NHCH(CO)CH$_2$ and OCH$_2$Ph; 5.32 (d, 1H) NH; 6.71 (d, 1H) NH; 7.36 (s, 5H) Ph.

Z-Leu-DL-Nva-enol ester, the precursor of Z-Leu-DL-Nva-COOEt was synthesized by the same procedure as described in Example PKC1 and purified by column chromatography, oil, one spot on tlc. NMR (CDCl$_3$) δ: 0.96 (t, 9H); 1.25 (t, 3H); 1.41 (t, 2H); 1.54 (m, 4H); 1.72 (m, 3H); 2.80 (t, 2H); 4.20 (q, 2H); 4.43 (q, 2H); 5.16 (q, 2H); 5.23 (s, 1H); 7.37 (m, 5H); 11.33 (s, 1H).

EXAMPLE PKC18

Z-Leu-DL-Phe-COOEt. This compound was prepared from Z-Leu-Phe-OH in 30% yield by the procedure described in Example PKC1; oil, one spot on tlc, $R_f=0.47$ (CHCl$_3$:MeOH=50:1). NMR (CDCl$_3$) δ: 0.88 (d, 9H), OCH$_2$CH$_3$ and (CH$_3$)$_2$CH; 1.35 (q, 2H), OCH$_2$CH$_3$; 1.56 (q, 2H), (CH$_3$)$_2$CHCH$_2$CH; 3.03 (m, 1H), (CH$_3$)$_2$CH; 4.32 (m, 2H), NHCH(CO)CH$_2$; 5.08 (s, 4H) CH$_2$Ph; 5.40 (m, 1H) NH; 6.61 (d, 1H) NH; 7.31 (s, 5H) Ph; 7.35.(s, 5H) Ph.

Z-Leu-DL-Phe-enol ester, the precursor of Z-Leu-DL-Phe-COOEt was synthesized by the same procedure as described in Example PKC1 and purified by column chromatography, oil, one spot on tlc. NMR (CDCl$_3$) δ: 0.86 (t, 3H); 0.99 (t, 3H); 1.24 (t, 3H); 1.40 (t, 3H); 1.52 (m, 2H), 1.83 (m, 2H); 4.23 (m, 4H); 4.39 (q, 2H); 5.10 (t, 2H); 5.18 (s, 1H); 7.26 (m, 5H); 7.34 (m, 5H); 8.89 (s, 1H).

EXAMPLE PKC19

Z-Leu-DL-Abu-COOEt. This compound was prepared from Z-Leu-Abu-OH in 33% yield by the procedure described in Example PKC1; oil, one spot on tlc, $R_f=0.66$ (CHCl$_3$:MeOH=20:1). NMR (CDCl$_3$) δ: 0.96 (t, 9H), OCH$_2$CH$_3$ and (CH$_3$)$_2$CH; 1.26 (t, 3H), CH$_2$CH$_2$CH$_3$; 1.37 (q, 2H), OCH$_2$CH$_3$; 1.66 (q, 2H), (CH$_3$)$_2$CHCH$_2$CH; 2.00 (m, 1H), CH(CH$_3$)$_2$; 4.12 (q, 2H) CHCH$_2$CH$_3$; 4.34 (m, 1H) NHCH(CONH)CH$_2$CH(CH$_3$)$_2$; 5.12 (q, 3H) CH$_2$Ph and CONH(Et)CHCOCOO; 5.29 (t, 1H) NH; 6.79 (d, 1H) NH; 7.35 (s, 5H) Ph.

Z-Leu-DL-Abu-enol ester, the precursor of Z-Leu-DL-Abu-COOEt was synthesized by the same procedure as described in Example PKC1 and purified by column chromatography, oil, one spot on tlc. NMR (CDCl$_3$) δ: 0.98 (t, 6H); 1.12 (t, 3H); 1.24 (t, 3H); 1.41 (t, 3H); 1.73 (m, 4H); 2.86 (q, 2H); 4.20 (q, 2H); 4.31 (m, 1H); 4.42 (q, 2H); 5.15 (q, 2H); 5.21 (s, 1H); 7.34 (m, 5H); 11.29 (s, 1H).

EXAMPLE PKC20

Ala-DL-Lys-COOEt.HCl. To a solution of N-carbobenzyloxyalanyl-N$^ε$-carbobenzyloxylysine (1.88 g, 3.9 mmol), 4-dimethylaminopyridine (21 mg, 0.17 mmol), and pyridine (1.0 mL, 12.4 mmol) in THF (7 mL) was added ethyl oxalyl chloride (0.9 mL, 8.0 mmol) at a rate sufficient to start refluxing. The mixture was refluxed gently for 3 hr, treated with water (4 mL), and stirred vigorously at room temperature for 30 min. The mixture was extracted with ethyl acetate, the organic extracts were washed with water, dried over MgSO$_4$ and evaporated to give an oily residue (1.56 g). To a solution of the enol ester (1.56 g, 2.7 mmol) in anhydrous ethanol was added dropwise a solution of sodium ethoxide in ethanol at room temperature until the solution turned clear yellow. Ethanol was removed and the residue was dissolved in ethyl acetate. The organic solution was washed with water, dried over MgSO$_4$, and evaporated to give a residue. This residue was then purified by column chromatography and the product was eluted with chloroform-methanol. The solvent was removed and Z-Ala-DL-Lys(Z)-CO$_2$Et was obtained as a hygroscopic powder (328 mg, 16%), single spot on tlc, $R_f^2=0.53$ (CHCl$_3$:MeOH=9:1); MS, m/e=542 (M$^+$+1).

N-Carbobenzoxyalanyl-DL-N$^ε$carbobenzoxylysine keto ethyl ester, Z-Ala-DL-Lys(Z)-CO$_2$Et (328 mg, 0.61 mmol) was deprotected with liquid HF containing anisole at 0° C. for 30 min. The HF was removed under reduced pressure. The residual oil was dissolved in absolute ethanol. HCl/ethanol was added to the solution, and ethanol was removed in vacuo. The residue was washed by decantation with ether to give a semi solid (216 mg, 100%); single spot on tlc (n-butanol:acetic acid:pyridine:H$_2$O=4:1:1:2).

EXAMPLE PKC21

Bz-DL-Lys-COOEt.HCl. This compound was prepared from Bz-DL-Lys(Z)-COOEt in 62% yield by the procedure described in Example PKC20; one spot on tlc, $R_f^4=0.57$ (n-butanol:acetic acid:pyridine:H$_2$O=4:1:1:2). The precursor, Bz-DL-Lys(Z)-COOEt was prepared from Bz-Lys(Z)-OH in 100% yield by the procedure described in Example PKC1; powder, one spot on tlc, $R_f^2=0.75$ (CHCl$_3$:MeOH=9:1); MS, m/e=440 (M$^+$). Anal. Calcd. for C$_{24}$H$_{28}$O$_6$N$_2$.⅔ H$_2$O: C, 63.70; H, 6.53; N, 6.19. Found: C, 63.49; H, 6.51; N, 5.92.

EXAMPLE PKC22

Bz-DL-Arg-COOEt.HCl. This compound was prepared from Bz-DL-Arg(Z)-COOEt in 99% yield by the procedure described in Example PKC20; one spot on tlc, $R_f^4=0.71$ (n-butanol:acetic acid:pyridine:H$_2$O=4:1:1:2), Sakaguchi reagent positive. Bz-DL-Arg(Z)-COOEt was prepared from Bz-DL-Arg(Z)-OH in 19% yield by the procedure described in Example PKC20, $R_f^2=0.38$ (CHCl$_3$:MeOH=9:1); mp 140°–142° C.; MS, m/e=468 (M$^+$). Anal. Calcd. for C$_{24}$H$_{28}$O$_6$N$_4$: C, 61.53; H, 6.02; N, 11.96. Found: C, 61.96; H, 6.48; N, 12.34.

EXAMPLE PKC23

H-Gly-DL-Lys-COOEt.2HCl. This compound was prepared from Z-Gly-DL-Lys(Z)-COOEt in 92% yield by the procedure described in Example PKC20; $R_f^4=0.21$ (n-butanol:acetic acid:pyridine:H$_2$O=4:1:1:2). Z-Gly-DL-Lys(Z)-COOEt was prepared from Z-Gly-Lys(Z)-OH in 9% yield by the procedure described in Example PKC20, one spot on tlc, $R_f^1=0.68$ (CHCl$_3$:MeOH=5:1); MS, m/e=528 (M$^+$+1).

EXAMPLE PKC24

H-Pro-DL-Lys-COOEt.2HCl. This compound was prepared from Z-Pro-DL-Lys(Z)-COOEt in 100% yield by the procedure described in Example PKC20; one spot on tlc (n-butanol:acetic acid:pyridine:H$_2$O=4:1:1:2). Z-Pro-DL-Lys(Z)-COOEt was prepared from Z-Pro-Lys(Z)-OH in 15% yield by the procedure described in Example PKC20; $R_f^2=0.73$ (CHCl$_3$:MeOH=9:1); MS, m/e 568 (M$^+$+1).

EXAMPLE PKC25

H-Phe-DL-Lys-COOEt.2HCl. This compound was prepared from Z-Phe-DL-Lys(Z)-COOEt in 39% yield by the procedure described in Example PKC20; one spot on tlc (n-butanol:acetic acid:pyridine:H$_2$O=4:1:1:2). Z-Phe-DL-Lys(Z)-COOEt was prepared from Z-Phe-Lys(Z)-OH as previously described in 9% yield, $R_f^2=0.68$ (CHCl$_3$:MeOH=9:1); MS, m/e=482 (M$^+$).

EXAMPLE PKC26

H-Leu-Ala-DL-Lys-COOEt.2HCl. This compound was prepared from Z-Leu-Ala-DL-Lys(Z)-COOEt in 52% yield by the procedure described in Example PKC20; one spot on tlc (n-butanol:acetic acid:pyridine:H$_2$O=4:1:1:2).

Z-Leu-Ala-DL-Lys(Z)-COOEt was prepared from Z-Leu-Ala-DL-Lys(Z)-OH in 5% yield by the previously described Dakin West reaction, $R_f^3$=0.34 (CHCl$_3$:MeOH=19:1); MS, m/e=609 (M$^+$—OCH$_2$CH$_3$).

EXAMPLE PKC27

Simple Amino Acid, Di- and Tripeptide Enol Esters (General Procedure). A modified Dakin-West procedure was used [Charles et al., *J. Chem. Soc. Perkin I,* 1139 (1980)] and is illustrated with the synthesis of Z-Leu-DL-Phe-EE. To a stirred solution of Z-Leu-Phe-OH (6.19 g, 15.0 mmol), 4- dimethylaminopyridine (0.183 g; 1,5 mmol) and pyridine (4.75 g, 4,85 ml, 60 mmol) in tetrahydrofuran (45 ml) warmed 50° C. was added ethyl oxalyl chloride (4.30 g, 3.52 ml, 31.5 mmol) at a rate sufficient to initiate refluxing. The mixture was then heated at a gentle reflux for 4 h. After cooling to room temperature the mixture was treated with water (25 ml) and stirred vigorously at room temperature for 30 min. The mixture was extracted with ethyl acetate (150 ml) and after separation of the organic layer, the water layer was saturated with solid (NH$_4$)$_2$SO$_4$ and re-extracted 2-times with 25 ml ethyl acetate. The combined organic phases were washed 2-times with 75 ml water, 2-times with 50 ml of satd. NaCl, decolorized with carbon and dried over MgSO$_4$. After evaporation of the solvent, the crude enol ester (8,36 g, 98%) was flash-chromatographed on silica gel and the product was eluted with a AcOEt. The solvent was evaporated in vacuo (rotavaporator) and the pure enol ester was obtained as a oil (7.22 g, 85%); single spot on TLC, $R_f$=0.84, A; 0.68, C.

Z-Leu-Nva-EE. This compound was prepared from Z-Leu-Nva-OH using the general procedure and purified by flash chromatography on silica gel using CHCl$_3$:MeOH=50:1 v/v as eluent. Yield 95%, single spot on TLC, $R_f$=0.92, C; 0.28, L.

Z-Leu-Abu-EE. This compound was prepared from Z-Leu-Abu- OH in 78% yield the general procedure described above. Purification by flash chromatography on silica gel. Eluent, CHCl$_3$:MeOH=50:1 v/v, single spot on TLC, Rf=0,86, A.

PhCO-Abu-EE. This compound was prepared from PhCO-Abu-OH in 26% yield by the general procedure as described above. Purification by flash chromatography on silica gel. Eluent CHCl$_3$, single spot on TLC, $R_f$=0.60, M.

(CH3)$_2$CH(CH$_2$)$_2$CO-Abu-EE. This compound was prepared from (CH$_3$)$_2$CH(CH$_2$)$_2$CO-Abu-OH in 82% yield by the general procedure as described above. Purification by flash chromatography on silica gel. Eluent AcOEt, single spot on TLC, $R_f$=0.72, C.

(CH$_3$CH$_2$CH$_2$)$_2$ CH CO-Abu-EE. This compound was prepared from (CH$_3$CH$_2$CH$_2$)$_2$CH CO-Abu-OH in 100% yield by the general procedure described above. Purification by flash chromatography on silica gel. Eluent AcOEt, single spot on TLC, $R_f$=0.78, C; 0.81, K.

Ph(CH$_2$)$_6$CO-Abu-EE. This compound was prepared from Ph(CH$_2$)$_6$CO-Abu-OH in 86% yield by the general procedure described above. Purification by flash chromatography on silica gel. Eluent AcOEt. Single spot on TLC, $R_f$=0.74, C.

Z-Leu-4-Cl-Phe-EE. This compound was prepared from Z-Leu-4-Cl-Phe-OH in 69% yield by the general procedure described above. Purification by flash chromatography on silica gel. Eluent AcOEt, single spot on TLC, $R_f$=0.77, C; 0.78, K.

Z-Leu-Leu-Abu-EE. This compound was prepared from Z2-Leu- Leu-Abu-OH in 62% yield by the general procedure described above. Purification by flash chromatography on silica gel. Element CHCl$_3$:MeOH=50:1 v/v. Single spot on TLC, $R_f$=0.89, A; 0.75, M.

Z-Leu-Leu-Phe-EE. This compound was prepared from Z-Leu-Leu-Phe-OH in 60% yield by the general procedure described above. Purification by flash chromatography on silica gel. Eluent CHCl$_3$:MeOH=50:1 v/v. Single spot on TLC, $R_f$=0.80, K; 0.70, M.

2-NapSO$_2$-Leu-Leu-Abu-EE. This compound was prepared from 2-NapSO$_2$-Leu-Abu-OH in 73% yield by the general procedure described above. Purification by flash chromatography on silica gel. Eluent AcOEt, single spot on TLC, $R_f$=0.71, K; 0.54, C.

2-NapSO$_2$-Leu-Leu-Abu-EE. This compound was prepared from 2-NapSO$_2$-Leu-Leu-Abu-OH in 74% yield by the general procedure described above. Purification by flash chromatography on silica gel. Eluent AcOEt: AcOH=200:1 v/v. Single spot on TLC, $R_f$=0.69. K.

Z-Leu-Phe-COOEt. Single Aminoacid, Di- and Tripeptide-ketoesters (General Procedure). To a stirred solution of 8.53 g (15.0 mmol) of Z-Leu-Phe-EE in 40 ml anhydrous ethanol at room temperature was added dropwise a solution of sodium ethoxide (0.204 g; 3.0 mmol) in 20.0 ml anhydrous ethanol. The color of the reaction mixture change from colorless or pall yellow to deep yellow or orange dependent on enol-ester. Then the reaction mixture was stirred at room temperature for 4–5 hours, the ethanol was then evaporated in vacuo (rotavaporator) and the residue treated with 200 ml ethyl ether (or 200 ml ethyl acetate in the case of the tripeptide). The ether (ethyl acetate) solution was washed with 2×75 ml H$_2$O, 2×75 ml satd. NaCl, decolorized with carbon and dried over MgSO$_4$. After evaporation of solvent, the crude product 6.09 g (89.7%) was flash chromatographed on silica gel using CHCl$_3$: MeOH=50:1 v/v. Evaporation of solvent give pure Z-Leu-Phe-COOEt (4.08 g; 58.0%) as a thick oil. Single spot on TLC, $R_f$=0.60, A; 0.47, M. Mass spectrum, FB-MS [(M+1)/Z]=469.

EXAMPLE PKC28

2-Leu-Nva-COOEt. This was prepared by the preceding general procedure. Purification by flash chromatography on silica gel, eluent CHCl$_3$: MeOH=100:1 v/v, yield 86.6%, thick, colorless oil, single spot on TLC, $R_f$=0.49, A; 0.37, M. Mass spectrum FB-MS [(M+1)/Z]=421.

EXAMPLE PKC29

Z-Len-Abu-COOEt. This was prepared by the preceding general procedure. Purification by flash chromatography on silica gel, eluent CHCl$_3$, yield 82%, thick, pale yellow oil, single spot on TLC, $R_f$=0.66, A. Mass spectrum, CI-MS [(M+1)/Z]=407.

EXAMPLE PKC30

PhCO-Abu-COOEt. This was prepared by the preceding general procedure. Purification by flash chromatography on silica gel, eluent CHCl$_3$:MeOH=50:1 v/v, yield 83%, oil, single spot on TLC, $R_f$=0.44, M. Mass spectrum, M/Z 263 (M+); CI-MS, 264 ((M+1)/Z).

EXAMPLE PKC31

(CH$_3$)$_2$CH(CH$_2$)$_2$CO-Abu-COOEt. This was prepared by the preceding general procedure. Purification by flash chromatography on silica gel, eluent AcOEt, yield 43%, oil, single spot on TLC, $R_f$=0.56, C. Mass spectrum EI-MS M/Z 257 (M+); FB-MS, [(M+1)/Z]=258.

EXAMPLE PKC32

$CH_3CH_2CH)_2CHCO$-Abu-COOEt. This was prepared by the preceding general procedure. Purification by flash chromatography on silica gel, eluent $CHCl_3$:MeOH=50:1 v/v, thick, yellowish oil, yield 66%, single spot on TLC, $R_f$=0.80, C; 0.66, M. Mass spectrum EI-MS M/Z=285 (M+); CI-MS, [(M+1)/Z]=286.

EXAMPLE PKC33

$Ph(CH_2)_6$CO-Abu-COOEt. This was prepared by the preceding general procedure. Purification by flash chromatography on silica gel, eluent $CHCl_3$:MeOH=50:1 v/v, yield 64%, pale yellow oil, single spot on TLC, $R_f$=0.29, M. Mass spectrum EI-MS M/Z=347 (M+), FB-MS, [(M+1)/Z]=348.

EXAMPLE PKC34

Z-Leu-4-Cl-Phe-COOEt. This was prepared by the preceding general procedure. Purification by flash chromatography on silica gel, eluent AcOEt, yield 100%, colorless oil, single spot on TLC, $R_f$=0.71, C. Mass spectrum FB-MS M/Z=503(M+).

EXAMPLE PKC35

Z-Leu-Leu-Abu-COOEt. This was prepared by the preceding general procedure. Purification by flash chromatography on silica gel, eluent $CHCl_3$:MeOH=50:1 v/v, yield 79.2%, very thick, colorless oil, single spot on TLC, $R_f$=0.28. M. Mass spectrum FB-MS, [(M+1)/Z]=520.

EXAMPLE PKC36

Z-Leu-Leu-Phe-COOEt. This was prepared by the preceding general procedure. Purification by flash chromatography on silica gel, eluent $CHCl_3$:MeOH=50:1 v/v, yield 33%, oil, single spot on TLC, $R_f$=0.56, M. Mass spectrum, FB-MS, [(M+1)/Z]=582.

EXAMPLE PKC37

2-$NapSO_2$-Leu-Abu-COOEt. This was prepared by the preceding general procedure. Purification by flash chromatography on silica gel, eluent $CHCl_3$:MeOH=50:1 v/v, yield 38%, thick oil, single spot on TLC, $R_f$=0.71, K; 0.54, A. Mass spectrum FB-MS, [(M+1)/Z]=463.

EXAMPLE PKC38

2-$NapSO_2$-Leu-Leu-Abu-COOEt. This was prepared by the preceding general procedure. Purification by flash chromatography on silica gel, eluent AcOEt:AcOH=200:1 v/v, yield 61%, semi-solid, single spot on TLC, $R_f$=0.67, K. Mass spectrum FB-MS, [(M+1)/Z]=576.

EXAMPLE PKC39

Z-Leu-Met-$CO_2$Et. This compound was prepared by the above procedure. Yellow oil, single spot on TLC, $R_f$=0.52 ($CHCl_3$:$CH_3$OH=50:), yield 46% (from dipeptide), MS (FAB) 454 (m+1).

EXAMPLE PKC40

Z-Leu-NLeu-$CO_2$Et. This compound was prepared by the above procedure. Pale yellow oil, single spot on TLC, $R_f$=0.57 ($CHCl_3$:$CH_3$OH=50:1), yield 53% (from dipeptide), MS (FAB) 434 (m+1).

EXAMPLE PKC41

Synthesis of n-Butyl Oxalyl Chloride. This was prepared by a literature procedure [Warren and Malee, *J. Chromat.* 64, 219–222 (1972)]. N-Butanol (0.1 mol. 7.41 g) was added dropwise to oxalyl chloride (0.5 mol. 63.5 g) at −10° C. After the addition was completed, the reaction mixture was stirred for 20 min. at r.t. and distilled, giving 15.0 g (91.18 mol. 91%) of the product n-butyl oxalyl chloride, bp 58°–60° C. (0.6 mm Hg).

Z-Leu-Phe-$CO_2$Bu. This compound was prepared from Z-Leu-Phe-OH and butyl oxalyl chloride in 43% yield by the procedure described for the synthesis of Z-Leu-Phe-$CO_2$Et, except that butyl oxalyl chloride was used in place of ethyl oxalyl chloride and sodium butyloxide in butanol was used for enol ester hydrolysis. Single spot on TLC, $R_f$=0.54 ($CHCl_3$:$CH_3$OH=50:1) MS(FAB) m/e=497 (m+1), $^1$H NMR ($CDCl_3$) ok.

EXAMPLE PKC42

Z-Leu-Abu-$CO_2$Bu. This compound was prepared by the above procedure. Single spot on TLC, $R_f$=0.53 ($CHCl_3$:$CH_3$OH=50:1), yield=36%, pale yellow oil, MS (FAB) m/e=435 (M+1), $^1$H NMR ($CDCl_3$) ok.

EXAMPLE PKC43

Synthesis of Benzyl Oxalyl Chloride. Benzyl alcohol (0.15 mol. 16 g) was added dropwise to oxalyl chloride (0.75 mol. 95 g) at 5°–10° C. After the addition was complete, the reaction was stirred for 20 min. at r.t. The excess oxalyl chloride was distilled and recycled. Then the mixture was distilled under vacuo, giving 26 g (0.12 mol. 86%) of benzyl oxalyl chloride, bp. 110°–112° C. (0.6 mm-Hg). H$^1$NMR ($CDCl_3$) 7.39 (s, 5H), 5,33 (s.2H).

Z-Leu-Phe-$CO_2$Bzl. This compound was prepared from Z-Leu-Phe-OH and benzyl oxalyl chloride in 17% yield by the procedure described in the synthesis of Z-Leu-Phe-$CO_2$Et, except that benzyl oxalyl chloride was used in place of ethyl oxalyl chloride and sodium benzyloxide in benzyl alcohol was used for enol ester hydrolysis. Single spot on TLC, $R_f$=0.63 ($CHCl_3$:$CH_3$OH=50:1). Pale yellow solid, mp 117°–119° C. MS(FAB) m/e=532 (m+1). H$^1$NMR ok.

EXAMPLE PKC44

Z-Leu-Abu-$CO_2$Bzl. This compound was prepared by the above procedure. Single spot on TLC. $R_f$=0.51 ($CHCl_3$:$CH_3$OH=50:1), pale yellow oil, MS(FAB) m/e=469 (m+1), yield=26%.

EXAMPLE PKC45

Z-Leu-Phe-COOH. Dipeptide Ketoacids (General Procedure). To a stirred solution of 0.53 g (1,13 mmol) Z-Leu-Phe-COOEt in 6.0 ml methanol was added 1.27 ml (1.27 mmol) 1M NaOH. The color of the reaction mixture turned dark yellow and a small amount of solid was deposited. The reaction was run at room temperature and progress of the hydrolysis was checked on TLC. After 24 h. no more substrate was detected. The reaction mixture was chilled in one ice bath at 5° C., acidified with 1M HCl to pH=3 and extracted with AcOEt (2×50 mL). The organic extract were washed with 2×50 ml H$_2$O and if necessary, decolorized with carbon and dried over MgSO$_4$. After evaporation of the solvent (rotavaporator), the residue (thick oil) were titurated with 2×25 ml n-hexane and dried in vacuo. Yield 0.39 g (78%) of colorless, very thick oil. TLC, main spot at R$_f$=0.24, trace of impurity at R$_f$=0.78, I. Mass spectrum, FB-MS [(M+1)/Z]=441.

EXAMPLE PKC46

Z-Leu-Abu-COOH. This compound was prepared from Z-L-Leu-Abu-COOEt in 83% yield by the general procedure as described above; TLC, main spot at R$_f$=0.14, trace of impurity at R$_f$=0.73, I. Mass spectrum, FB-MS [(M+1)/Z]=379.

EXAMPLE PKC47

Z-Leu-Phe-CONH-Et. To a stirred solution of Z-Leu-Phe-OH (20 g, 48.5 mmole), 4-dimethylaminopyridine (0.587 g, 4.8 mmole), and pyridine (15.7 ml, 194 mmole) in anhydrous THF (100 ml) was added ethyl oxalyl chloride (11.4 ml, 101.8 mmole) at a rate sufficient to initiate refluxing. The mixture was gently refluxed for 4 hours, cooled to room temperature, and water (80 ml) was added. The reaction mixture was stirred vigorously for 30 min, and extracted with ethyl acetate (3×100 ml). The combined organic layers were washed with water (2×100 ml), saturated sodium chloride (2×100 ml), decolorized with decolorizing carbon, dried over magnesium sulfate, and concentrated, leaving a dark orange oil. Chromatography on a silica gel column with CHCl$_3$/CH$_3$OH (50:1 v/v) afforded 14.63 g (y=53%) of Z-Leu-Phe-enolester. The product was a yellow oil. Single spot on TLC, R$_f$=0.77 (CHCL$_3$/CH$_3$OH 50:1). NMR (CDCl$_3$) ok.

To a stirred pale yellow solution of the Z-Leu-Phe-enolester (14.63 g, 25.73 mmole) in anhydrous ethanol (50 ml) was added a solution of sodium ethoxide (0.177 g, 2.6 mmole) in ethanol (5 ml). The orange solution was stirred for 3 hours at room temperature, then the ethanol was evaporated and the residue was treated with ethyl ether (300 ml). The ether layer was washed with water (2×100 ml), saturated sodium chloride (2×100 ml), dried over magnesium sulfate, and concentrated, leaving a orange oil. Chromatography on a silica gel column with CHCl$_3$/CH$_3$OH (50:1 v/v) afforded 7.76 g (y=64%) of the α-ketoester Z-Leu-Phe-COOEt. The product was a yellow oil. Single spot on TLC, R$_f$=0.44 (CHCl$_3$/CH$_3$OH 50:1). NMR (CDCl$_3$) ok. MS (FAB, calcd. for C$_{26}$H$_{32}$N$_2$O$_6$: 468.6), m/e=469 (M+1).

The α-carbonyl group of Z-Leu-Phe-COOEt was protected by following procedure. A solution of Z-Leu-Phe-COOEt (1 g, 2.13 mmole) in 5 ml of CH$_2$Cl$_2$ was added 1,2-ethanedithiol (0.214 ml, 2.55 mmole), followed by 0.5 ml of boron trifluoride etherate. The solution was stirred overnight at room temperature. Water (20 ml) and ethyl ether (20 ml) were added. The organic layer was separated, washed with water (2×10 ml), saturated sodium chloride (2×10 ml), dried over magnesium sulfate, and evaporated to afford 0.98 g (y=84%) yellow semisolid.

The protected α-ketoester (0.98 g, 1.8 mmole) was dissolved in ethanol (5 ml), cooled to 0°–5° C. in a ice bath, and ethylamine was bubbled through the solution until 2.43 g (54 mmole) had been added. The reaction mixture was allowed to warm to room temperature slowly, and stirred overnight. The mixture was filtered, a white precipitate was removed, leaving a yellow semisolid. Chromatography on a silica gel column with CHCl$_3$/CH$_3$OH (30:1 v/v) afford 0.63 g (y=75%) of Z-Leu-Phe-CONH-Et. The product was a pale yellow solid. Single spot on TLC, R$_f$=0.60 (CHCl$_3$/CH$_3$OH 20:1); mp 145°–147° C. Anal. calcd. for C$_{26}$H$_{33}$N$_3$O$_5$: 467.56; C, 66.79; H, 7.11; N,8.99; found: C, 66.59; H, 7.09; N, 8.95. NMR (CDCl$_3$) ok. MS (FAB) m/e=468 (M+1).

EXAMPLE PKC48

Z-Leu-Phe-CONH-nPr. This compound was synthesized from the protected α-ketoester and propylamine in 92% yield by the procedure described in Example PKC47. Single spot on TLC, R$_f$=0.50 (CHCl$_3$/CH$_3$OH 50:1); mp 152°–153° C. Anal. calcd. for C$_{27}$H$_{35}$N$_3$O$_5$: 481.57; C, 67.33; H, 7.33; N, 8.72. Found: C, 67.21; H, 7.38; N, 8.64. NMR (CDCl$_3$) ok. MS (FAB) m/e=482 (M+1).

EXAMPLE PKC49

Z-Leu-Phe-CONH-nBu. This compound was synthesized from the protected α-ketoester and butylamine in 67% yield by the procedure described in Example PKC47. Single spot on TLC, R$_f$=0.50.(CHCl$_3$/CH$_3$OH 50:1); mp 152°–153° C. Anal. calcd. for C$_{28}$H$_{37}$N$_3$O$_5$: 495.59; C, 67.85; H, 7.52; N, 8.48. Found: C, 67.70; H, 7.57; N, 8.43. NMR (CDCl$_3$) ok. MS (FAB) m/e=496 (M+1).

EXAMPLE PKC50

Z-Leu-Phe-CONH-iBu. This compound was synthesized from the protected α-ketoester and isobutylamine in 53% yield by the procedure described in Example PKC47. Single spot on TLC, R$_f$=0.54 (CHCl$_3$/CH$_3$OH 50:1); mp 152° C. Anal. calcd. for C$_{28}$H$_{37}$N$_3$O$_5$: 495.59; C, 67.85; H, 7.52; N, 8.48. Found: C, 67.77; H, 7.56; N, 8.40. NMR (CDCl$_3$) ok. MS (FAB) m/e=496 (M+1).

EXAMPLE PKC51

Z-Leu-Phe-CONH-Bzl. This compound was synthesized from the protected α-ketoester and benzylamine in 40% yield by the procedure described in Example PKC47. After reacting overnight, ethyl acetate (60 ml) was added. The mixture was filtered to remove a white precipitate. The solution was washed with cooled 1N HCl (3×25 ml), water (1×20 ml), saturated sodium chloride (2×20 ml), and dried over magnesium sulfate. The solution was evaporated leaving a yellow solid. Chromatography on a silica gel column with CHCl$_3$/CH$_3$OH 30:1 v/v) afforded a yellow solid. Single spot on TLC, R$_f$=0.45 (CHCl$_3$/CH$_3$OH 30:1); mp 160°–162° C. Anal. calcd. for C$_{31}$H$_{35}$N$_3$O$_5$: 529.61; C, 70.30; H, 6.66; N, 7.93. Found: C, 70.18; H, 6.67; N, 7.99. NMR (CDCl$_3$) ok. MS (FAB) m/e=530 (M+1).

EXAMPLE PKC52

Z-Leu-Phe-CONH-(CH$_2$)$_2$Ph. This compound was synthesized from the protected α-ketoester and phenethylamine in 50% yield by the procedure described in Example PKC51. Single spot on TLC, R$_f$=0.50 (CHCl$_3$/CH$_3$OH 30:1); mp 151°–153° C. Anal. calcd. for C$_{32}$H$_{37}$N$_3$O$_5$: 543.66; C, 70.70; H, 6.86; N, 7.73. Found: C, 70.54; H, 6.88; N, 7.74. NMR (CDCl$_3$) ok. MS (FAB) m/e=544 (M+1).

EXAMPLE PKC53

Z-Leu-Abu-CONH-Et. This compound was synthesized from protected α-ketoester derived from Z-Leu-Abu-CO$_2$Et and ethylamine in 64% yield by the procedure described in Example PKC47. Single spot on TLC, R$_f$=0.36 (CHCl$_3$/CH$_3$OH 50;1); mp 130°–132° C. Anal. calcd. for C$_{21}$H$_{31}$N$_3$O$_5$: 405.45; C, 62.20; H, 7.71; N, 10.36. Found: C, 61.92; H, 7.62; N, 10.31. NMR (CDCl$_3$) ok. MS (FAB) m/e=406 (M+1).

EXAMPLE PKC54

Z-Leu-Abu-CONH-nPr. This compound was synthesized from the corresponding protected α-ketoester and propylamine in 47% yield by the procedure described in Example PKC47. Single spot on TLC, R$_f$=0.28 (CHCl$_3$/CH$_3$OH 50:1); mp 134°–135 ° C. Anal. calcd. for C$_{22}$H$_{33}$N$_3$O$_5$: 419.50; C, 62.98; H, 7.93; N 10.02. Found: C, 62.84; H, 7.97; N, 9.94. NMR (CDCl$_3$) ok. MS (FAB) m/e=420 (M+1).

EXAMPLE PKC55

Z-Leu-Abu-CONH-nBu. This compound was synthesized from the corresponding protected α-ketoester and butylamine in 42% yield by the procedure described in Example PKC47. Single spot on TLC, R$_f$=0.54 (CHCl$_3$/CH$_3$OH 50:1); mp 135°–136° C. Anal. calcd. for C$_{23}$H$_{35}$N$_3$O$_5$: 433.53; C, 63.71; H, 8.13; N, 9.69. Found: C, 63.48; H, 8.07; N, 9.67. NMR (CDCl$_3$) ok. MS (FAB) m/e=434 (M+1).

EXAMPLE PKC56

Z-Leu-Abu-CONH-iBu. This compound was synthesized from the corresponding protected α-ketoester and isobutylamine in 65% yield by the procedure described in Example PKC47. Single spot on TLC, R$_f$=0.25 (CHCl$_3$/CH$_3$OH 50:1); mp 133°–135° C. Anal. calcd. for C$_{23}$H$_{35}$N$_3$O$_5$: 433.52; C, 63.72; H, 8.14; N, 9.69. Found: C, 63.46; H, 8.10; N, 9.60. NMR (CDCl$_3$) ok. MS (FAB) m/e=434 (M+1).

EXAMPLE PKC57

Z-Leu-Abu-CONH-Bzl. This compound was synthesized from the corresponding protected α-ketoester and benzylamine in 29% yield by the procedure described in Example PKC51. Single spot on TLC, R$_f$=0.56 (CHCl$_3$/CH$_3$OH 30:1); mp 140°–141° C. Anal. calcd. for C$_{26}$H$_{33}$N$_3$O$_5$: 467.54; C, 66.79; H, 7.11; N, 8.99. Found: C, 66.65; H, 7.07; N, 8.93. NMR (CDCl$_3$) ok. MS (FAB) m/e=468 (M+1).

EXAMPLE PKC58

Z-Leu-Abu-CONH-(CH$_2$)$_2$Ph. This compound was synthesized from the corresponding protected α-ketoester and phenethylamine in 51% yield by the procedure described in Example PKC51. Single spot on TLC, R$_f$=0.44 (CHCl$_3$/CH$_3$OH 30:1); mp 156°–157° C. Anal. calcd. for C$_{27}$H$_{35}$N$_3$O$_5$: 481.59; C, 67.34; H, 7.33; N, 8.72. Found: C, 67.38; H, 7.33; N, 8.78. NMR (CDCl$_3$) ok. MS (FAB) m/e=482 (M+1).

EXAMPLE PKC59

Z-Leu-Abu-CONH—(CH$_2$)$_3$-N(CH$_2$CH$_2$)$_2$O. This compound was synthesized from protected α-ketoester and 4(3-aminopropyl)morpholine in 33% yield by the procedure described in Example PKC47. After reacting overnight, ethyl acetate (80 ml) was added. The mixture was filtered to remove a white precipitate. The solution was washed with water (3×20 ml), saturated sodium chloride (2×20 ml), and dried over magnesium sulfate. The solution was evaporated leaving a yellow oil. Chromatography on a silica gel column with CHCl$_3$/CH$_3$OH (10:1 v/v) afforded a yellow semisolid, which was recrystallized from ethyl acetate/hexane to obtain a pale yellow solid. Single spot on TLC, R$_f$=0.42 (CHCl$_3$/CH$_3$OH 10:1); mp 125°–126° C. Anal. calcd. for C$_{26}$H$_{40}$N$_4$O$_6$: 504.63; C, 61.88; H, 7.99; N, 11.10. Found: C, 61,69; H, 7.95; N, 11.07. NMR (CDCl$_3$) ok. MS (FAB) m/e=505 (M+1).

EXAMPLE PKC60

Z-Leu-Abu-CONH—(CH$_2$)$_7$CH$_3$. This compound was synthesized from the corresponding protected α-ketoester and octylamine in 67% yield by the procedure described in Example PKC51. It was white solid. Single spot on TLC, R$_f$=0.55 (CHCl$_3$/CH$_3$OH 30:1); mp 134°–135° C. Anal. calcd. for C$_{27}$H$_{43}$N$_3$O$_5$: 489.66; C, 66.23; H, 8.85; N, 8.58. Found: C, 66.19; H, 8.81; N, 8.61. NMR (CDCl$_3$) ok. MS (FAB) m/e=490 (M+1).

EXAMPLE PKC61

Z-Leu-Abu-CONH-(CH$_2$)$_2$OH. This compound was synthesized from the corresponding protected α-ketoester and ethanolamine in 29% yield by the procedure described in Example PKC59. The product was a white sticky solid. Single spot on TLC, R$_f$=0.42 (CHCl$_3$/CH$_3$OH 10:1); mp 151°–153° C. Anal. calcd. for C$_{21}$H$_{31}$N$_3$O$_6$: 421.49; C, 59.84; H, 7.41; N, 9.97. Found: C, 59.11; H, 7.44; N, 9.81. NMR (CDCl$_3$) ok. MS (FAB) m/e=422 (M+1).

EXAMPLE PKC62

Z-Leu-Abu-CONH—(CH$_2$)$_2$O(CH$_2$)$_2$OH. This compound was synthesized from the corresponding protected α-ketoester and 2-(2-aminoethoxy)ethanol in 34% yield by the procedure described in Example PKC59. The product was white sticky solid. Single spot on TLC, R$_f$=0.42 (CHCl$_3$/CH$_3$OH 10:1); mp 103°–105° C. Anal.: calcd. for C$_{23}$H$_{35}$N$_3$O$_7$: 465.55; C, 59.34; H, 7.58; N, 9.03. Found: C, 59.23; H, 7.58; N, 9.01. NMR CDCl$_3$) ok. MS (FAB) m/e=466 (M+1).

EXAMPLE PKC63

Z-Leu-Abu-CONH—(CH$_2$)$_{17}$CH$_3$. This compound was synthesized from the corresponding protected α-ketoester and octadecylamine in 12% yield by the procedure described in Example PKC51. The product was a pale yellow solid. Single spot on TLC, R$_f$=0.54 (CHCl$_3$/CH$_3$OH 30:1); mp 134°–136° C. Anal: calcd. for C$_{37}$H$_{63}$N$_3$O$_5$: 629.92; C, 70.55; H, 10.08; N, 6.67. Found: C, 70.71; H, 10.14; N, 6.75. NMR (CDCl$_3$) ok. MS (FAB) m/e=630.2 (M+1).

EXAMPLE PKC64

Z-Leu-Abu-CONH—CH$_2$—C$_6$H$_3$(OCH$_3$)$_2$. This compound was synthesized from the corresponding protected α-ketoester and 3,5-dimethoxybenzylamine in 45% yield by the procedure described in Example PKC51. The product was yellow sticky solid. Single spot on TLC, R$_f$=0.44 (CHCl$_3$/CH$_3$OH 30:1); mp 153°–155° C. Anal.: calcd. for C$_{28}$H$_{37}$N$_3$O$_7$: 527.62; C, 63.74; H, 7.07; N, 7.96. Found: C, 63.66; H, 7.09; N, 7.92. NMR (CDCl$_3$) ok. MS (FAB) m/e=528.8 (M+1).

EXAMPLE PKC65

Z-Leu-Abu-CONH—$CH_2$—$C_4H_4N$. This compound was synthesized from the corresponding protected α-ketoester and 4-(aminomethyl)pyridine in 45% yield by the procedure described in Example PKC59. The product was greenish yellow solid. Single spot on TLC, $R_f$=0.55 ($CHCl_3$/$CH_3OH$ 10:1); mp 124°–126° C. Anal: calcd. for $C_{25}H_{32}N_4O_5$: 468.55; C, 64.08; H, 6.88; N, 11.96. Found: C, 63.88; H, 6.87; N, 11.96. NMR ($CDCl_3$) ok. MS (FAB) m/e=469 (M+1).

D. HALO-KETONE PEPTIDES

Halomethyl ketone peptides are irreversible inhibitors for serine proteases and cysteine proteases. This class of compounds includes peptides having a variety of halomethyl groups at their C-terminus. These halomethyl groups include —$CH_2X$, —$CHX_2$ and $CX_3$, where X represents any halogen. A number of analogous compounds have been synthesized, including the amino-halo ketones and the diazo-ketone peptides. Although these analogous compounds are chemically distinguishable, all of these haloketone compounds are believed to have a similar mechanism of action. Accordingly, for simplicity, all of the foregoing compounds will be referred to collectively herein as the "Halo-Ketone Peptides."

The reactivity of haloketones has generally been found to be in the order I>Br>Cl>F. However, increasing the reactivity of the haloketone in this way can lead to acceleration of competing side effects. Thus, it is preferable to increase the reactivity of the halomethyl ketone peptides by altering the peptide structure.

In selecting a proper inhibitor for Calpain, the same basic peptide structure selection techniques as used for the Peptide Keto-Compounds can be used. Once a peptide structure has been identified, the most effective C-terminus grouping can be empirically determined through kinetic inhibition studies of each of the compounds with Calpain.

Many of the Halo-Ketone Peptides are available commercially. For example, Leu-$CH_2Cl$, Phe-$CH_2Cl$, Z-lys-$CH_2Cl$, Tosyl-Lys$CH_2Cl$ (TLCK), Tosyl-PheCH$_2$Cl (TPCK), Z-Gly-Leu-Phe-$CH_2Cl$, Z-Phe-Ala-$CH_2Cl$, z-Phe-Phe-$CH_2Cl$, D-Phe-Pro-Arg-$CH_2Cl$, MeoSuc-Phe-Gly-Gly-Ala-$CH_2Cl$, MeoSuc-Ala-Ala-Pro-Ala-$CH_2Cl$, MeoSuc-Ala-Ala-Pro-Val-$CH_2Cl$, Ala-Ala-Pro-Val-$CH_2Cl$, Ala-Ala-Phe-$CH_2Cl$, Suc-Ala-Ala-Pro-Phe-$CH_2Cl$ and D-Val-Leu-Lys-$CH_2Cl$ are all available from suppliers such as Enzyme Systems Products of Livermore, Calif. From the same suppliers, the following diazomethyl ketone peptides are available: Leu-$CHN_2$, Z-Phe-Phe-$CHN_2$, Z-Phe-Ala-$CHN_2$, Z-Phe-Pro-$CHN_2$, Z-Lys-$CHN_2$ and Gly-Phe-$CHN_2$. In addition, the production of α-amino fluoro ketone peptides has been described in U.S. Pat. No. 4,518,528 to David W. Rasnick, the disclosure of which is hereby incorporated by this reference.

The preparation of various Halo-Ketone Peptides is reviewed in *Methods in Enzymology*, 46:197–208 (1977), the disclosure of which is hereby incorporated by reference. Briefly, halomethyl ketone derivatives of blocked amino acids are readily prepared by the reaction of mineral acids (hydrohalic) with the corresponding diazomethyl ketone. Iodomethyl ketones are prepared by reaction of a halo-ketone with NaI, since reaction with HI with a diazomethyl ketone yields the methyl ketone. A number of different blocking groups can be used, including benzyloxycarbonyl (Z) and t-butyloxycarbonyl (Boc). The diazomethyl ketone is prepared by reaction of diazomethane with the appropriate acid activated by means of dicyclohexylcarbodiimide (DCCI), by the mixed anhydride method.

Unblocked amino acid chloromethyl ketones can be prepared by reaction of benzyloxycarbonyl blocked derivatives with HBr or HOAc, trifluoroacetic acid, or by hydrogenation.

Synthesis of peptide chloromethyl ketones can be accomplished simply by coupling an appropriate peptide or amino acid with an unblocked amino acid chloromethyl ketone. A few dipeptides can be converted directly to the chloromethyl ketone using the mixed anhydride and $CH_2N_2$ followed by HCl.

Various synthetic problems are encountered in the preparation of chloromethyl ketone derivatives of basic amino acids. The side chain usually must be blocked during synthesis, and difficulties are often encountered during removal of the blocking group. Use of trifluoroacetic acid or HF was eventually found to give a good conversion to product.

A number of examples of the preparation of Halo-Ketone Peptides have been reported in the literature, including a comprehensive review of over 100 amino acid derivatives and approximately 60 peptide derivatives listed in J. C. Powers, in "Chemistry and Biochemistry of Amino Acids, Peptides and Proteins," Vol. 4, Dekker, N.Y. (1977), the disclosure of which is hereby incorporated by reference. Those of skill in the art will recognize how to locate a multitude of examples of the production of the Halo-Ketone Peptides. Accordingly, no additional examples are provided herein.

E. IN VITRO USES

In addition to the foregoing classes of compounds now discovered to possess Calpain inhibitory activity, we believe that a large number of other such compounds exist. In view of the large number of inhibitors of Calpain of different classes we disclose herein, all of the known, newly discovered and yet undiscovered inhibitors of Calpain shall be referred to hereinafter collectively, using the term "Calpain Inhibitor."

The Calpain Inhibitors may be used in vitro for a variety of purposes to inhibit unwanted Calpain activity. For example, the Calpain Inhibitors may be used in vitro to prevent proteolysis that occurs in the process of production, isolation, purification, storage or transport of peptides and proteins.

The Calpain Inhibitors described herein can also be used in vitro to prevent further degradation of tissue samples from occurring after preparation of the samples. This in vitro prevention of degradation can be especially useful in the preparation of assays for neurodegeneration wherein the assay comprises a test for the products of Calpain activity in the tissues, such as assays for breakdown products (BDP's) of cytoskeletal components such as spectrin, MAP2, actin binding protein and tau. P. Seubert et al., in *Neuroscience*, 31:195 (1989), the disclosure of which is hereby incorporated by reference, disclose an exemplary method of quantitating the amount of spectrin BDP's as an indication of Calpain activity.

The Calpain Inhibitors of this invention are also useful in a variety of other experimental procedures where proteolysis due to Calpains is a significant problem. For example, inclusion of the Calpain Inhibitors in radioimmunoassay experiments can result in higher sensitivity. The use of the Calpain Inhibitors in plasma fractionation procedures can result in higher yields of valuable plasma proteins and can make purification of the proteins easier. The Calpain Inhibitors disclosed here can be used in cloning experiments utilizing recombinant or transfected bacterial or eukaryotic cell cultures in order to increase yield of purified recombinant product.

To use the Calpain Inhibitors in vitro, the Calpain Inhibitors are dissolved in an organic acid, such as dimethylsulfoxide (DMSO) or ethanol, and are added to an aqueous solution containing the protease which is to be inhibited, such that the final concentration of organic solvent is 25% or less. The Calpain Inhibitors may also be added as solids or in suspension.

F. TREATMENT OF NEURODEGENERATION

We have discovered that the Calpain Inhibitors are useful in vivo to treat pathologies in which excess proteolysis by Calpains is involved. Such pathologies are believed to include neuropathologies such as neurodegeneration resulting from excitotoxicity, HIV-induced neuropathy, ischemia, denervation, injury, subarachnoid hemorrhage, stroke, multiple infarction dementia, Alzheimer's Disease (AD), Huntington's Disease, surgery-related brain damage, Parkinson's Disease, and other pathological conditions.

1. Identification of Inhibitors

In order to identify Calpain Inhibitors that are useful in the practice of the present invention for treatment or inhibition of neurodegenerative conditions and diseases, it is important to identify those inhibitors posessing significant Calpain inhibitory activity. It is also important to identify those Calpain Inhibitors having a high degree of specificity for inhibition of Calpain, in order to avoid interference with other biological processes when the Calpain Inhibitor is introduced into a mammal requiring treatment for neurodegeneration. Because all thiol proteases are believed to exert their effect through a similar mechanism of action, our primary concern was to identify those Calpain Inhibitors having substantial inhibitory activity against Calpain, but relatively weak or no activity against other thiol proteases. Accordingly, in order to identify such Calpain Inhibitors, we tested a variety of Calpain Inhibitors for their ability to inhibit calpains I and II, and compared this data with the ability of the same Calpain Inhibitors to inhibit Cathepsin B, another thiol protease. Those Calpain Inhibitors with high in vitro inhibitory activity against Calpain and a relatively lower activity against Cathepsin B are believed to be most useful for in vivo therapy. Examples 1A through 1C show the results of these studies for a variety of Calpain Inhibitors.

EXAMPLE 1A

Inhibition by Substituted Heterocyclic Compounds

The isocoumarins are irreversible inhibitors of Calpain. We obtained $IC_{50}$ values for a variety of these Calpain Inhibitors as a kinetic analysis of these compounds. Purified Calpains can be assayed using the fluorogenic substrate succinyl-leucine-tyrosine-methylaminocoumarin (available commercially) or by measuring the release of acid-soluble peptides from casein because we have found that the isocoumarins inhibit casein proteolysis by Calpain.

Calpains I and II were purified by the method of (Yoshimura, et al. 1983). (Kitahara 1984) provides an alternative purification scheme. Calpain II may alternatively be purchased from Sigma Chemical Co. as "Calcium Activated Neutral Protease." In this assay, purified Calpain was incubated with $^{14}C$-methylated casein in the presence of various Heterocyclic Compounds and the amount of acid-soluble radioactivity released by the action of Calpain was measured. The $IC_{50}$ values were determined as the concentration of Heterocyclic Compound compound at which 50% of the Calpain activity was inhibited. Table 1A shows $IC_{50}$ values for various Isocoumarin Compounds.

TABLE 1A

| INHIBITION OF CALPAINS BY SUBSTITUTED ISOCOUMARINS | | |
|---|---|---|
| | $IC_{50}$ ($\mu M$) | |
| | Calpain I | Calpain II |
| CiTprOIC | 100 | 70 |
| NH$_2$-CiTPrOIC (ACITIC) | 10 | 120 |
| PhCH$_2$NHCONH-CiTPrOIC | 80 | 30 |
| CH$_3$CONH-CiTPrOIC | 700 | 80 |
| L-Phe-NH-CiTPrOIC | | 30 |
| BOC-L-Phe-NH-CiTPrOIC | no inhibition | >200 |
| PhCH$_2$NHCONH-CiTEtOIC | 90 | |
| PhCH$_2$CONH-CiTEtOIC | 30 | |
| D-Phe-NH-CiTEtOIC | 200 | |

Thus, it can be seen from Table 1A that a variety of the Isocoumarin Compounds have significant Calpain inhibitory activity at low concentrations.

EXAMPLE 1B(i)

Protease Inhibition by Peptide Keto-Compounds

The Peptide Keto-Compounds are reversible inhibitors of Calpains and other thiol proteases. The $K_i$ values for the inhibition of calpain I, calpain II and Cathepsin B were determined for several Peptide Keto-Compounds, Inhibition of calpain I from human erythrocytes and calpain II from rabbit muscle were assayed using Suc-Leu-Tyr-amidomethylcoumarin as substrate in an assay buffer of 20 mM HEPES pH=7.2, 10 mM CaCl$_2$, 10 mM $\beta$-mercaptoethanol. Cathepsin B from bovine spleen was assayed using Z-Lys-4-nitrophenylphosphate as substrate.

Table 1B(i) shows the results of the studies of Example 1B(i). The Ki value for the inhibition of Calpains and cathepsin B by several Peptide Keto-Compounds are shown in $\mu M$ (micromolar). The values for leupeptin, which is commercially available from Calbiochem of La Jolla, Calif., are shown for comparison.

TABLE 1B(i)

| $K_i$ VALUES FOR PEPTIDE KETO-COMPOUNDS | | | |
|---|---|---|---|
| Inhibitor | Calpain I | Calpain II | Cathepsin B |
| Leupeptin | 0.32 | 0.43 | 6 |
| Z-Ala-Ala-Ala-CO$_2$Me | 200 | — | 1.5 |
| Z-Ala-Ala-Abu-CO$_2$Et | 50 | 200 | 0.9 |
| Z-Leu-Phe-CO$_2$Et | 0.23 | 0.4 | >50 |
| Z-Leu-Nle-CO$_2$Et | 0.12 | 0.18 | 18 |
| Z-Leu-Abu-CO$_2$Et | 0.04 | 0.4 | 14 |
| Z-Leu-Nva-COOEt | | 1.2 | 30 |

It can be seen from the results in Table 1B(i) that the Peptide Keto-Compounds inhibit Calpain with Ki values similar or superior to leupeptin. In particular, Z-Leu-Phe-CO$_2$Et, Z-Leu-Nle-CO$_1$Et and Z-Leu-Abu-CO$_2$Et were found to possess greater Calpain inhibitory activity than leupeptin. In addition, these particular compounds were highly specific to Calpain, with lower inhibitory activity toward Cathepsin B than leupeptin.

EXAMPLE 1B(ii)

Protease Inhibition of Peptide Keto-Compounds

We tested the ability of an additional group of Peptide Keto-Compounds to inhibit several proteases in order to evaluate their specificity for Calpain. The results of these studies are shown in Table 1B(ii).

TABLE 1B(ii)

Inhibition of Calpain I, Calpain II, Cathepsin B, PP Elastase and Papain

| Inhibitor | $K_I(\mu M)$ | | | | | |
|---|---|---|---|---|---|---|
| | Calpain I | Calpain II | CathB | Chym | elastase | papain |
| Z-Leu-Abu-COOEt | 4.5 | 0.4 | 30 | >100 | >100 | 220 |
| Z-Leu-Abu-COOnBu | 1.8 | | 4 | >100 | 25 | 10 |
| Z-Leu-Abu-COOBz | 9.5 | 0.47 | 4 | >100 | >100 | 40 |
| Z-Leu-Leu-Abu-COOEt | 1.8 | 2.6 | 22 | >100 | 25 | |
| 2-NapSO$_2$-Leu-Leu-Abu-COOEt | 16 | 1.4 | 25 | 35 | 47 | |
| 2-NapCO-Leu-Leu-Abu-COOEt | | 0.09 | | >300 | 28 | |
| Tos-Leu-Leu-Abu-COOEt | 33 | | 69 | 25 | 28 | |
| Ph-(CH$_3$)$_2$-CO-Leu-Abu-COOEt | | 1.2 | | | | |
| Z-Leu-Abu-COOH | 0.075 | 0.022 | 1.5 | >150 | >150 | |
| Z-Leu-Abu-CONHEt | 0.5 | 0.23 | 2.4 | >150 | 65 | |
| Z-Leu-Abu-CONHnPr | | 0.25 | 8 | >300 | 2 | |
| Z-Leu-Abu-CONHnBu | 0.2 | | 13 | >300 | 5 | |
| Z-Leu-Abu-CONHiBu | | 0.14 | 4 | >300 | 40 | |
| Z-Leu-Abu-CONHBz | | 0.35 | 2 | >300 | | |
| Z-Leu-Abu-CONH-(CH$_2$)$_2$-Ph | | 0.022 | | | | |
| Z-Leu-Abu-CONH-(CH$_2$)$_3$-Mpl | | 0.041 | | | | |
| Z-Leu-Abu-CONH-(CH$_2$)$_7$CH$_3$ | | 0.019 | | | | |
| Z-Leu-Abu-CONH-(CH$_2$)$_2$OH | | 0.078 | | | | |
| Z-Leu-Abu-CONH-(CH$_2$)$_2$O(CH$_2$)$_2$OH | 0.16 | | | | | |
| Z-Leu-Phe-COOEt | 1.8 | 0.4 | 340 | 0.025 | >100 | 75 |
| Z-Leu-Phe-COOnBu | 5.0 | 1.1 | 15 | 0.15 | >100 | 15 |
| Z-Leu-Phe-COOBz | 3.4 | 1.6 | 45 | 1.6 | >100 | 45 |
| Z-Leu-Leu-Phe-COOEt | 1.4 | 1.9 | 42 | 0.26 | >100 | 15 |
| Z-Leu-Phe-COOH | 0.0085 | 0.0057 | 4.5 | 76 | >150 | |
| Z-Leu-Phe-CONHEt | 7.0 | 0.32 | 6 | 73 | >150 | |
| Z-Leu-Phe-CONHnPr | 15.0 | 0.05 | 3 | 18 | >300 | |
| Z-Leu-Phe-CONHnBu | | 0.028 | 3 | 8 | >100 | |
| Z-Leu-Phe-CONHiBu | | 0.065 | 4 | 24 | | |
| Z-Leu-Phe-CONHBz | | 0.046 | | | | |
| Z-Leu-Phe-CONH(CH$_2$)$_2$Ph | | 0.024 | | (2) | | |
| Z-Leu-Nle-COOEt | | 0.18 | 20 | | 2.2 | 190 |
| Z-Leu-Nva-COOEt | 1.4 | 1.2 | 25 | 160 | 2.3 | 150 |
| Z-Leu-Met-COOEt | 1.0 | 1.5 | 55 | 1.75 | >100 | 140 |
| Z-Leu-4-Cl-Phe-COOEt | <4.0 | 0.4 | 50 | 0.9 | >100 | 150 |

Table 1B(ii) shows the inhibition constants ($K_I$) for cathepsin B, calpain I, and calpain II with peptide ketoamides. Dipeptide Ketoamides with Abu and Phe in the P$_1$ site and Leu in the P$_2$ site are potent inhibitors of calpain I and calpain II. Z-Leu-Abu-CONH-Et is a better inhibitor of calpain I than Z-Leu-Phe-CONH-Et by 14 fold. Replacement of the Z group (PhCH$_2$OCO—) by similar groups such as PhCH$_2$CH$_2$CO—, PhCH$_2$CH$_2$SO$_2$—, PhCH$_2$NHCO—, and PhCH$_2$NHCS— would also result in good inhibitor structures. The best inhibitor of calpain II is Z-Leu-Abu-CONH—(CH$_2$)$_2$-Ph. Changing the R$_3$ and R$_4$ groups significantly improves the inhibitory potency toward calpain II. The best Dipeptide Ketoamide inhibitors are those which have long alkyl side chains (e.g. Z-Leu-Abu-CONH—(CH$_2$)$_7$CH$_3$), alkyl side chains with phenyl substituted on the alkyl group (e.g. Z-Leu-Abu-CONH—(CH$_2$)$_2$-Ph), or a alkyl groups with a morpholine ring substituted on the alkyl group [e.g. Z-Leu-Abu-CONH—(CH$_2$)$_3$-Mpl, Mpl=—N(CH$_2$CH$_2$)$_2$O]. Dipeptide α-ketoamides with a small aliphatic amino acid residue or a Phe in the P$_1$ site are also good inhibitors for cathepsin B. The best inhibitor is Z-Leu-Abu-CONH-Et and replacement of the Z (PhCH$_2$OCO—) by PhCH$_2$CH$_2$CO—, PhCH$_2$CH$_2$SO$_2$—, PhCH$_2$NHCO—, and PhCH$_2$NHCS— would also result in good inhibitor structures.

EXAMPLE 1B(iii)

Stability of Peptide Keto-Compounds

We determined the haft-life of several Peptide Keto-Compounds in both plasma and liver homogenates. The results of the determinations of stability of the compounds in plasma and liver homogenates are shown in Table 1B(iii).

TABLE 1B(iii)

Stability in Plasma and in Liver of Peptide Keto-Compounds.

| | $t_{\frac{1}{2}}$ | |
|---|---|---|
| Inhibitor | plasma | liver |
| Z-Leu-Abu-COOEt | 2.8 | |
| 2-NapSO$_2$-Leu-Leu-Abu-COOEt | >60 | |
| 2-NapCO-Leu-Leu-Abu-COOEt | 25 | |
| Tos-Leu-Leu-Abu-COOEt | 30 | |
| Z-Leu-Abu-COOH | >60 | >60 |
| Z-Leu-Abu-CONHEt | >60 | >60 |
| Z-Leu-Abu-CONHnPr | >60 | >60 |
| Z-Leu-Abu-CONHnBu | >60 | >60 |
| Z-Leu-Abu-CONHiBu | >60 | |
| Z-Leu-Abu-CONHBz | >60 | >60 |
| Z-Leu-Phe-COOEt | 7.8 | |
| Z-Leu-Phe-COOnBu | 7.7 | |
| Z-Leu-Phe-COOBz | 1.9 | |
| Z-Leu-Phe-COOH | >60 | >60 |
| Z-Leu-Phe-CONHEt | >60 | >60 |
| Z-Leu-Phe-CONHnPr | >60 | >60 |
| Z-Leu-Phe-CONHnBu | >60 | >60 |
| Z-Leu-Phe-CONHiBu | >60 | |
| Z-Leu-Phe-CONH(CH$_2$)$_2$Ph | >60 | |
| Z-Leu-Nle-COOEt | 3.7 | |

TABLE 1B(iii)-continued

Stability in Plasma and in Liver of Peptide Keto-Compounds.

| Inhibitor | $t_{\frac{1}{2}}$ plasma | liver |
|---|---|---|
| Z-Leu-Nva-COOEt | 2.8 | |
| Z-Leu-Met-COOEt | 8 | |

It can be seen from the data in Table 1B(iii) that the Peptide Keto-Compounds are generally quite stable in plasma and liver homogenates. However, it is also shown that the Peptide α-ketoamides were substantially more stable in both plasma and liver than the corresponding peptide α-ketoesters

EXAMPLE 1C

Protease Inhibition by Halo-Ketone Peptides

The Halo-Ketone Peptides, like the substituted isocoumarins, are irreversible inhibitors of Calpain. We determined the $K_{app}/[I]$ values for various members of this class of compounds against Calpains I and II. For comparison, we also determined these values against the additional thiol proteases Papain and Cathepsin B for at least one Halo-Ketone Peptide. These $K_{app}$ values are not directly comparable to the $K_i$ or $IC_{50}$ values determined above for other classes of inhibitors.

We assayed Calpain I and II using Suc-leu-tyr-amidomethylcoumarin. Papain was assayed using benzoyl-arg-4-nitroanilide, and Cathepsin B (bovine) was assayed using CBZ-lys-4-nitrophenyl ester. We followed the progress curve method of Tian and Tsou, *Biochemistry*, 21:1028–1032 (1982), the disclosure of which is hereby incorporated by reference, to derive kinetic data. Briefly, this method makes use of the equation:

$$[P_\infty] = \frac{V[S]/K}{(1 + [S]/K)A[Y]}$$

where $[P_\infty]$ represents the concentration of product formed at a time approaching infinity, A is the $K_{app}$ in the presence of substrate (S), K is the Michaelis constant and [Y] is the concentration of the inhibitor. Since [S] and [Y] are known and V and K can be determined, $K_{app}$ can be readily determined.

The $K_{app}/[I]$ for various Halo-Ketone Peptides are shown in Table 1C.

TABLE 1C

KINETIC PARAMETERS OF Halo-Ketone Peptides

| Inhibitor | CI | CII[3] | P | CB |
|---|---|---|---|---|
| Z-Gly-Leu-Phe-CH2Cl | 284000[1] | 946000 | | |
| Boc-Gly-Leu-Phe-CH2Cl | | 902000 | 540000 | 290000 |
| Z-Leu-Phe-CH2Cl | 225000[2] | 585000 | | |
| Z-Gly-Leu-Ala-CH2Cl | | 210000 | | |
| Ac-Leu-Phe-CH2Cl | 25900[1] | 33400 | | |
| Z-Val-Phe-CH2Cl | | 27200 | | |
| Z-Ala-Phe-CH2Cl | | 2400 | | |
| Ac-Ala-Ala-Ala-Ala-CH2Cl | | 1300 | | |

CI = Calpain I
CII = Calpain II
P = Papain
CB = Cathepsin B
[1] - Rat
[2] - Human
[3] - Rabbit It can be seen from the results in Table 1C that the Halo-Ketone Peptides inhibit Calpain with relatively high $K_{app}/[I]$ values. In particular, Z-gly-leu-phe-CH2Cl, Boc-gly-leu-phe-CH2Cl, Z-leu-phe-CH2Cl and Z-gly-leu-ala-CH2Cl were found to possess significant Calpain inhibitory activity. In addition, Boc-gly-leu-phe-CH2Cl was shown to be somewhat specific to Calpain, with lower inhibitory activity,toward Cathepsin B or Papain than toward Calpain. The results shown in the table reveal that Z-gly-leu-phe-CH2Cl and Boc-gly-leu-phe-CH2Cl produce similar inhibitory effects. Thus, the blocking group is not shown to have a great effect on Calpain inhibitory activity.

The kinetic constants of other irreversible Calpain Inhibitors include the following with $K_{app}/[I]$ in parentheses: E-64 (7500), E64-d (23000) and Z-leu-leu-tyr-CHN2 (230000). E-64 is commercially available from Sigma Chemical Co., and is shown here to be a poor inhibitor of Calpain. Z-leu-leu-tyr-CHN2 is a diazomethyl peptide compound, here shown to possess significant Calpain inhibitory activity.

2. Inhibition of Calpain in Neural Tissues

In order to evaluate the inhibition of Calpain by the various Calpain Inhibitors in neural tissues, we assayed the Calpain Inhibitors using the known ability of Calpain to cleave spectrin, a protein component of neuronal and other tissue, into BDP's. In this assay, more effective Calpain Inhibitors will prevent the conversion of spectrin into BDP's. Example 2 is one example of such an assay.

EXAMPLE 2

Inhibition of Calpain in Crude Brain Extracts by Calpain Inhibitors

The activity of Calpain in crude brain extracts was measured by examining the $Ca^{2+}$-stimulated proteolysis of the endogenous substrate spectrin. Brain tissue was homogenized in 10 mM Tris pH=7.4, 0.32M sucrose, 1 mM EGTA, 1 mM dithiothreitol and the nuclei and debris removed by low speed centrifugation. Various Calpain Inhibitors were added to the supernatant in a DMSO vehicle and a calcium salt (final effective concentration about 1.2 mM) added to start the reaction. Proteolysis of spectrin was evaluated by western blot as described by Seubert, et at. (Brain Research, 459:226–232, 1988), the disclosure of which is hereby incorporated by reference. Briefly, a known quantity of a spectrin-containing sample treated with Calpain is separated by SDS-PAGE and immunoblotted with anti-spectrin antibody. The amount of spectrin immunoreactivity found corresponding to the characteristic BDP's is indicative of the amount of spectrin activity present in the sample. An examplary method for quantitating BDP's is to assay Spectrin BDP's by homogenizing brain parts in 20 mM Tris pH=7.2, 0.32M sucrose, 50 μM Ac-Leu-Leu-nLeu-H on ice. Homogenates are then mixed 1:1 with 10% SDS, 5% β-mercaptoethanol, 10% glycerol, 10 mM Tris pH=8.0, 0.5% bromophenolblue, heated to 95° C., and subjected to electrophoresis in 4½% polyacrylamide gels. The proteins in the gels are transferred to nitrocellulose and the spectrin and BDP's detected using a rabbit polyclonal anti-spectrin antibody and established immunodetection methods. The amount of spectrin and BDP's in each sample can be quantitated by densitrometric scanning of the developed nitrocellulose.

Due to Calpain's requirement for $Ca^{2+}$, in the absence of $Ca^{2+}$ little or no spectrin proteolysis occurred, regardless of the presence of inhibitor, while in the presence of $Ca^{2+}$ the spectrin was >95% cleaved to BDP's within 40 min. if no Calpain Inhibitor is added.

Both leupeptin and CI1 showed inhibition in the system of Example 2. In addition, the following compounds of the Substituted Heterocyclic Compounds were found to produce significant inhibition at 100 μM:

3-chloroisocoumarin
3,4-dichloroisocoumarin
3-benzyloxy-4-chloroisocoumarin
7-(acetylamino)-4-chloro-3-(propoxy)-isocoumarin
4-chloro-3-(3-isothiureidopropoxy)isocoumarin
7-amino-4-chloro-3-(3-isothiureidopropoxy)isocoumarin
7-(benzylcarbamoylamino)-4-chloro-3-(3-isothiureidopropoxy)isocoumarin
7-(phenylcarbamoylamino)-4-chloro-3-(3-isothiureidopropoxy)isocoumarin
7-(acetylamino)-4-chloro-3-(3-isothiureidopropoxy)isocoumarin
7-(3-phenylpropionylamino)-4-chloro-3-(3-isothiureidopropoxy)isocoumarin
7-(phenylacetylamino)-4-chloro-3-(3-isothiureidopropoxy)isocoumarin
7-(L-phenylalanylamino)-4-chloro-3-(3-isothiureidopropoxy)isocoumarin
7-(benzylcarbamoylamino)-4-chloro-3-(3-isothiureidoethoxy)isocoumarin
7-(phenylcarbamoylamino)-4-chloro-3-(3-isothiureidoethoxy)isocoumarin
7-(D-phenylalanylamino)-4-chloro-3-(3-isothiureidoethoxy)isocoumarin.

The following compounds of the Halo-Ketone Peptides were also found to produce significant inhibition at 100 μM:

Z-Leu-Phe-CH2Cl
Ac-Leu-Phe-CH2Cl
Z-Gly-Leu-Phe-CH2Cl
Boc-Gly-Leu-Phe-CH2Cl
Ac-Val-Phe-CH2Cl
Z-Gly-Leu-Ala-CH2Cl.

In addition, the following compounds of the Peptide Keto-Compounds were found to produce significant inhibition at 100 μM:

Bz-DL-Phe-COOEt
Z-Leu-Nva-COOEt
Z-Leu-Nle-COOEt
Z-Leu-Phe-COOEt
Z-Leu-Abu-COOEt
Z-Leu-Met-COOEt
Z-Ala-Ala-DL-Abu-COOEt
MeO-Suc-Val-Pro-DL-Phe-COOMe
Z-Ala-Ala-Ala-DL-Ala-COOEt
MeO-Suc-Ala-Ala-Pro-DL-Abu-COOMe.
Z-Leu-Phe-COOEt

Thus, the Substituted Heterocyclic Compounds, Peptide Keto-Compounds and Halo-Ketone Peptides, in addition to leupeptin and CI1, provide inhibition in brain homogenates.

3. In Vivo Inhibition of Neurodegeneration through Infusion Techniques

In order to demonstrate that the inhibition of Calpain activity alone is sufficient to inhibit neurodegeneration in vivo, we tested the ability of the Calpain Inhibitor, leupeptin, to inhibit neurodegeneration in gerbils subjected to transient ischemia.

As stated above, leupeptin is poorly membrane permeant. Therefore, leupeptin is not expected to cross the blood-brain barrier ("BBB") very well. Accordingly, in order to provide the brain with sufficient leupeptin to adequately inhibit Calpain activation, we used brain infusion techniques. Through the use of these techniques we were able to subject brain tissues to intimate contact with leupeptin for sustained periods of time. Example 3A is provided to show the in vivo protection from neurodegeneration found during one such study.

EXAMPLE 3A

In Vivo Protection Against Neurodegeneration

A small cannula was implanted in the right lateral ventricle of adult gerbils, and secured to the skull with dental cement. An Alzet micro-osmotic pump was attached to the cannula for intracerebroventricular perfusion. The pump was filled with either saline alone (control) or leupeptin (20 mg/ml in saline). After three days perfusion with either the control solution or with the leupeptin solution, transient ischemia was induced by bilaterally clamping the carotid arteries for a period of ten minutes. Core temperatures were taken during and following ischemia, with no differences noted between control and leupeptin treated animals. Fourteen days later, the animals were sacrificed by Nembutal overdose and transcardial perfusion of a 10% solution of paraformaldehyde in PBS. Coronal sections of the brain were stained with cresyl violet and were examined for the extent of neuronal loss. The control gerbils exhibited the typical damage found in the CA1 field following ischemia, with a 72% loss of neurons. However, the leupeptin treated gerbils showed far less neurodegeneration, with only a 15% loss of neurons.

The results of Example 3A cannot be explained by changes in thermoregulation, since core temperatures did not differ between the groups. Accordingly, we believe that the Calpain inhibitory activity of leupeptin is responsible for the observed differences in neuronal cell loss. In order to further quantitate the differences, and verify that leupeptin produced a Calpain inhibitory effect within the observed regions of the brain, we performed a related series of experiments. In this series of experiments, spectrin BDP's were measured in the leupeptin treated and control animals. As discussed above, these BDP's are indicative of the amount of Calpain activity occurring within the tissue. Example 3B is provided to demonstrate the results of these experiments.

EXAMPLE 3B

In Vivo Inhibition of Calpain Activity

Implantation surgeries and clamping of the carotid arteries were performed as above with a control-ischemia group (n=4) and a leupeptin-ischemia group (n=5). A third group of animals (n=4) received implantation with pumping of saline, but was not subjected to ischemia. Animals were sacrificed by decapitation 30 minutes after clamping of the arteries. The brains were rapidly removed and placed in cold homogenization buffer (0.32M sucrose, 10 mM Tris-HCl, 2 mM EDTA, 1 mM EGTA, 100 μM leupeptin and 1 μg/ml of the Halo-Ketone Compound, tos-phe-CH2Cl (TPCK)). The CA1 region of the hippocampus was then dissected. The samples from both control and leupeptin treated animals were then prepared for SDS- PAGE and immunoblotting with labeled anti-spectrin antibody, as described above in connection with in vitro uses of the Calpain Inhibitors. The control animals exhibited a marked increase in the levels of BDP's relative to the gerbils not subjected to ischemia. These BDP's co-migrated with BDP's observed after in vitro proteolysis of spectrin with Calpain. The brain tissue from the leupeptin treated gerbils exhibited approximately 25% of the BDP's observed in the control ischemia treated gerbils.

Another group of gerbils (n=3) were sacrificed immediately after ischemia without leupeptin treatment in order to observe the effects of ischemia without reoxygenation. These gerbils exhibited a similar amount of increase of BDP's as the control-ischemic gerbils observed after a 30 minute reperfusion period.

Thus, the results of Example 3B indicate that leupeptin exerts its neuroprotective effect through the inhibition of Calpain activation. The results also indicate that the observed proteolysis of spectrin was an effect of ischemia, and not secondary to the reoxygenation. Accordingly, the results indicate that inhibition of Calpain activity in vivo produces a neuroprotective effect.

Although the foregoing studies demonstrate that leupeptin can inhibit neurodegeneration in vivo, leupeptin is not the therapeutic drug of choice because of the need to infuse the drug directly into the brain for an extended period of time to exert its neuroprotective effect. This is due to the relatively poor ability of this compound to cross the BBB. Accordingly, it is believed that a more therapeutically practical way to inhibit neurodegeneration would be to use more membrane permeant Inhibitor of Calpain.

4. Platelet Permeability

In accordance with our discoveries demonstrated in Examples 3 and 3A, we believe that having a compound cross the BBB and enter CNS tissue is a key characteristic of a therapeutically useful approach to treat or inhibit neurodegeneration within the CNS. Use of Calpain inhibitors that have enhanced membrane permeability is one such approach. Thus, we measured the ability of various Calpain inhibitors to penetrate the platelet membrane and inhibit Calpain that is normally contained in platelets. As shown below in the following examples, our results indicate that particular compounds of the Heterocyclic Compounds, Peptide Keto-Compounds and Halo-Ketone Peptides, in addition to the Peptide Aldehyde, CI1, exhibit good membrane permeability.

As an indication of the membrane permeability of the various Calpain Inhibitors, we measured the ability of various Calpain Inhibitors to penetrate platelet membranes and inhibit the Calpain normally found within platelets. The membrane of platelets is believed to have many similarities to the BBB and accordingly, such experiments are believed to provide a good indication of the ability of the various Calpain Inhibitors to cross the BBB. Example 4 shows the results of some of these platelet experiments using the Calpain Inhibitors of the present invention.

EXAMPLE 4A

Membrane Permeation of Calpain Inhibitors

Platelets were isolated by a modification of the method of Ferrell and Martin, *J Biol. Chem.*, 264:20723–20729 (1989), the disclosure of which is hereby incorporated by reference. Blood (15–20 ml) was drawn from male Sprague-Dawley rats into 100 mM EDTA-citrate containing 10 units heparin, and centrifuged 30 minutes at 1600 rpm at room temperature. The plasma was resuspended in 15 ml buffer 1 (136 mM NaCl, 2.7 mM KCl, 0.42 mM $NaH_2PO_4$, 12 mM $NaHCO_3$, 2 mM $MgCl_2$, 2 mg/ml BSA (Sigma), 5.6 mM glucose, 22 mM $Na_3$Citrate pH 6.5) and platelets were isolated at 2200 rpm at room temperature of 25 minutes. Platelets were resuspended to $10^7$ cells/ml in buffer 2 (136 mM NaCl, 2.7 mM KCl, 0.42 $NaH_2PO_4$, 12 mM $NaHCO_3$, 2 mM MgCl, 1 mg/ml BSA, 5.6 mM glucose, 20 mM HEPES pH 7.4) and allowed to "rest" for a minimum of 10 minutes at room temperature before use.

Platelets were incubated for 5 minutes in the presence of inhibitor. In order to provide sufficient intracellular calcium to activate Calpain, the calcium ionophore A23187 was added to a final concentration of 1 μM. After a further 5 minute incubation, the platelets were harvested by centrifugation (1 min 10,000×g) and resuspended in 10% sodium dodecyl sulfate, 10 mM Tris pH=8.0, 5% β-mercaptoethanol, 0.02% bromophenol blue, and heated to 95° C. for 5 min. Samples were subjected to SDS-PAGE on 6% mini gels and transferred to nitrocellulose (Schleicher and Schuell BAS3) for 2 hours at 100 mA/gel in an LKB Novablot. Filters were blocked for 10 minutes in 0.25% gelatin, 1% BSA, 0.25% Triton X100, 0.9% NaCl, 10 mM Tris-Cl pH 7.5, incubated overnight in the same solution containing antibody to rat spectrin, washed 3×10 minutes with 10 mM Tris-Cl pH 7.5, 0.5% Triton X100, incubated 4 hours in wash buffer plus alkaline phosphatase conjugated goat anti-rabbit antibody (Biorad), and washed as above. Filters were developed using the Biorad AP conjugate substrate kit. Spectrin immunoreactivity on the filters was quantitated by densitometry.

The inhibition of Calpain within platelets as measured by the proteolysis of the endogenous Calpain substrate spectrin in the presence of inhibitors was assayed for a variety of Calpain Inhibitors. The poorly permeant inhibitors leupeptin and E-64 had little effect on intracellular Calpain. In contrast, the highly membrane permeant Heterocyclic Compounds, Peptide Keto-Compounds, and Halo-Ketone Peptides effectively inhibited platelet Calpain.

The following Heterocyclic Compounds were found to produce significant inhibition at 100 μM in the system of Example 4:

3-chloroisocoumarin
4-chloro-3-(3-isothiureidopropoxy)isocoumarin
7-amino-4-chloro-3-(3-isothiureidopropoxy)isocoumarin
7-(benzylcarbamoylamino)-4-chloro-3-(3-isothiureidopropoxy)isocoumarin
7-(phenylcarbamoylamino)-4-chloro-3-(3-isothiureidopropoxy)isocoumarin
7-(acetylamino)-4-chloro-3-(3-isothiureidopropoxy)isocoumarin
7-(3-phenylpropionylamino)-4-chloro-3-(3-isothiureidopropoxy)isocoumarin
7-(phenylacetylamino)-4-chloro-3-(3-isothiureidopropoxy)isocoumarin
7-(L-phenylalanylamino)-4-chloro-3-(3-isothiureidopropoxy)isocoumarin
7-(benzylcarbamoylamino)-4-chloro-3-(3-isothiureidoethoxy)isocoumarin
7-(phenylcarbamoylamino)-4-chloro-3-(3-isothiureidoethoxy)isocoumarin 7-(D-phenylalanylamino)-4-chloro-3-(3-isothiureidoethoxy)isocoumarin.

The following Halo-Ketone Peptides were found to produce significant inhibition at 100 μM in the system of Example 4:

Z-Leu-Phe-CH2Cl
Ac-Leu-Phe-CH2Cl
Z-Gly-Leu-Phe-CH2Cl
Boc-Gly-Leu-Phe-CH2Cl.

The following Peptide Keto-Compounds were found to produce significant inhibition at 100 μM in the system of Example 4:

Z-Ala-Ala-D,L-Abu-COOEt
Z-Ala-Ala-Ala-D,L-Ala-COOEt
MeO-Suc-Ala-Ala-Pro-D,L-Abu-COOMe
Z-Leu-Phe-COOEt
Z-Leu-Nle-COOEt
Z-Leu-Nva-COOEt
Z-Leu-Abu-COOEt
Z-Leu-Abu
Z-Leu-4-Cl-Phe-COOEt
Z-Leu-Leu-Abu-COOEt
Z-Leu-Leu-Phe-COOEt
2-NapSO2-Leu-Abu-COOEt
2-NapSO2-Leu-Leu-Abu-COOEt
Z-Leu-Met-CO2Et
Z-Leu-NLeu-CO2Et
Z-Leu-Phe-CO2Bu
Z-Leu-Abu-CO2Bu
Z-Leu-Phe-CO2Bzl
Z-Leu-Abu-CO2Bzl
Z-Ala-Ala-D,L-Abu-COOBzl
Z-Leu-Phe-COOH
Z-Leu-Abu-COOH.

Among those compounds found to exhibit Calpain inhibitory activity in the homogenate system of Example 2, we found at least three compounds which failed to exhibit Calpain inhibitory activity in the platelet system of Example 4. These compounds are leupeptin, MeO-Suc-Val-Pro-D,L-Phe-COOMe and Bz-D,L-Phe-COOEt. Leupeptin is known to be poorly membrane permeant, thus confirming that the platelet assay will exclude known poorly membrane permeant compounds. Accordingly, the two Peptide Ketocompounds found not to provide Calpain inhibitory activity within platelets are also believed to be poorly membrane permeant, and would not be expected to cross the BBB.

EXAMPLE 4B

Quantitative Studies of Platelet Membrane Permeability

We performed additional quantitative or semi-quantitative studies on several Peptide Keto-Compounds using the assay of Example 4A, except that $IC_{50}$ values were determined as the concentration at which 50% of the Calpain activation present in controls occurred. Results are shown in Table 4B. For the semi-quantitative assays, indicated with +'s in Table 4B, "+" indicates detectable inhibition at 100 μM, "++" indicates significantly more inhibition than "+", and "+++" indicates no detectable activation of Calpain detected.

TABLE 4B

Platelet Assay of Peptide Ketoamides, Ketoesters and Ketoacids

| Inhibitor | $IC_{50}$ |
|---|---|
| Z-Leu-Abu-COOEt | 42 |
| Z-Leu-Abu-COOnBu | 28 |
| Z-Leu-Abu-COOBz | ++ |
| Z-Leu-Leu-Abu-COOEt | 40 |
| 2-NapSO2-Leu-Leu-Abu-COOEt | 100 |
| Tos-Leu-Leu-Abu-COOEt | 30 |
| Z-Leu-Abu-COOH | 8 |
| Z-Leu-Abu-CONHEt | 1.5 |
| Z-Leu-Abu-CONHnPr | 70 |
| Z-Leu-Abu-CONHnBu | 2.0 |
| Z-Leu-Abu-CONHiBu | 28 |
| Z-Leu-Abu-CONHBz | 1.5 |
| Z-Leu-Phe-COOEt | 42 |
| Z-Leu-Phe-COOnBu | +++ |
| Z-Leu-Phe-COOBz | ++ |
| Z-Leu-Leu-Phe-COOEt | ++ |
| Z-Leu-Phe-COOH | 6.5 |
| Z-Leu-Phe-CONHEt | 1.7 |
| Z-Leu-Phe-CONHnPr | 24 |
| Z-Leu-Phe-CONHnBu | 38 |
| Z-Leu-Phe-CONHiBu | 22 |
| Z-Leu-Phe-CONH(CH2)2Ph | 3.0 |
| Z-Leu-Nle-COOEt | 20 |
| Z-Leu-Nva-COOEt | 40 |
| Z-Leu-Met-COOEt | + |
| Z-Leu-4-Cl-Phe-COOEt | + |

Table 4B shows that peptide α-ketoamides and ketoacids were much more effective than corresponding peptide ketoesters in this platelet assay. Extending the $R_3$ group to an alkyl group or an alkyl group substituted with a phenyl group increased the membrane permeability of the inhibitors as indicated by increased potency in the platelet assay. In view of these results, Applicants believe that extending the R group to include longer alkyl groups or alkyl groups substituted with phenyl groups would increase the membrane permeability of a given inhibitor.

In view of the foregoing, the results of Examples 4A and 4B support our belief that CI1 and the Substituted Heterocyclic Compounds, Peptide Keto-Compounds and Halo-Ketone Peptides are believed to be membrane permeant and therefore, are expected to be effective in crossing the BBB subsequent to in vivo administration of the compounds.

5. Glutamate Toxicity

To further identify those Calpain Inhibitors likely to possess pharmacologically active neuroprotective ability, we tested the ability of the Calpain Inhibitors to protect against glutamate excitotoxicity. Excess extracellular glutamate is thought to play a key role in the induction of neuropathology in ischemia, which is accompanied by Calpain activation. In support of this role for excess glutamate, cultured N18-RE-105 (a neuroblastoma-retinal hybrid) cells can be killed by the addition of glutamate into the culture medium. This glutamate-mediated cytotoxicity is calcium dependent and can be reduced through a number of mechanisms, including free radical scavengers, blockers of the N-type voltage-sensitive calcium channel, and quisqualate-subtype glutamate antagonists. Thus, glutamate-mediated killing of N18-RE-105 cells is an in vitro model for neuropathology.

Accordingly, we tested the ability of the Calpain Inhibitors to inhibit glutamate-induced cell death in these cells in order to establish that the Calpain Inhibitors can decrease or prevent glutamate-induced death Of N18-RE-105 cells. Some of these tests are shown in Example 5.

EXAMPLE 5

Inhibition of Glutamate-Induced Cell Death

Stock cultures of N18-RE-105 cells were maintained in Dulbecco's modified Eagle's medium (DMEM) containing 10% fetal bovine serum (FBS) and supplemented with hypoxanthine, aminopterin and thymidine (HAT). Subconfluent cultures were split and plated into 96-well plates. Twenty-four hours after plating the cells were exposed to fresh media containing glutamate and various concentrations of Calpain inhibitors. Control cells were not treated with glutamate. The treated cells received 5 mM glutamate and leupeptin (5 µg/ml) or the other Calpain Inhibitors listed in FIG. 1 at 3 µg/ml. Conversion of MTT was measured 19 hours later as described. Nineteen hours after the onset of exposure, cell viability was quantitated by measuring the extent to which the cells convert 3(4,5-dimethylthiazol-2-yl)-2-5-diphenyltetrazolium bromide (MTT) to a blue formazan product, which occurs in the mitochondria of living but not dead cells (Pauwels et al., 1988). A higher absorbance is indicative of greater cell viability.

FIG. 1 shows the percent of blue formazan product remaining after treatment with glutamate, relative to control where no glutamate was added. Thus, it can be seen that with vehicle plus glutamate but no inhibitor, less than 70% of the mitochondrial activity remains. However, FIG. 1 shows that several Calpain inhibitors, including leupeptin, CI1 and representatives of the Heterocyclic Compounds, Peptide Keto-Compounds and Halo-Ketone Peptides protect N18-RE-105 cells against glutamate toxicity. The Peptide Keto-Compound Calpain inhibitor, Z-Ala-Ala-Abu-CO2Et, the Substituted Heterocyclic Compounds, CITPrOIC and ACITIC, and the Halo-Ketone Peptide, TPCK completely blocked the toxic effects of glutamate, resulting in 100% or greater of the formazan product as seen with cells not treated with glutamate. Thus, Example 5 shows that these Calpain Inhibitors effectively block cell death in an in vitro model for neuropathology. Accordingly, this data further supports our discovery that Calpain Inhibitors are neuroprotective in vivo.

6. Reduction of Infarction upon MCA Occlusion

Stroke is a significant health problem in the human population. Strokes are occlusions of cerebral arteries producing a decreased blood flow to brain regions, which cause cell death through oxygen and nutrient deprivation. This type of lesion can be modeled in rats by surgical occlusion of the middle cerebral artery (MCA). Several models for MCA occlusion have been developed, and all give substantially similar results.

MCA occlusion produces a large volume of infarcted brain tissue 24 hours after occlusion. Previous studies have shown that the size of the infarct as judged by TTC staining does not increase after the first 24 hours post-occlusion. Thus, we used an MCA occlusion model in order to test the ability of Calpain inhibitors to prevent neurodegeneration. This model is described in Example 6.

EXAMPLE 6

MCA Occlusion Model for Neurodegeneration

Male Sprague-Dawley albino rats weighing approximately 250–300 grams were anesthetized with pentobarbital (70 mg/kg, i.p.). The neck region was shaven and a 2 cm incision was made. The superficial fascia was teased away with tissue forceps and blunt tip tissue scissors using a spread method. The right common carotid artery was isolated away from the vagus nerve and tied off with a single suture (3.0 silk). The external carotid was permanently occluded by suturing. The bifurcation of the internal carotid and pterygopalatine arteries was exposed and a single microaneurysm clip was placed on the pterygopalatine. Another microaneurysm clip was placed on the common carotid just proximal to the external/internal bifurcation. A suture was placed loosely around the common carotid and a lumen was made in the vessel with the tip of a 25 g needle. A 40 mm nylon suture was prepared by melting the tip to smooth the pointed end and marked with a dot exactly 17.5 mm from the melted end. The suture was inserted into the lumen of the artery as far as the vessel clip, the clip is removed and the suture advanced until the marking was at the bifurcation of the internal and external carotid arteries. This places the end of the suture in the circle of Willis just beyond the source of the middle cerebral artery and occludes this artery. The loose suture around the carotid is tied lightly to keep the nylon suture in place. The microaneurysm clip on the pterygopalatine artery was removed, the incision is closed and the animals are allowed to recover in heated recovery cages.

Twenty-four hours after occlusion, the brains of these animals were removed and sliced into 2 mm sections. The sections were stained using 2,3,5-triphenyltetrazolium chloride (see Lundy, E. F., Solik, B. S., Frank, R. S., Lacy, P. S., Combs, D. J., Zelenock, G. B., and D'Alecy, L. G., Morphometric evaluation of brain infarcts in rats and gerbils, *J. Pharmacol. Meth.* 16,201–214, 1986). Absence of red color development indicated tissue damage or death. The sizes of the infarcted tissue zone (area with red stain) and impaired zone (area with partial development of red color) were evaluated using quantitative morphometry.

Drugs or vehicle were administered by infusion into the femoral vein. All animals received the same volume of drug or vehicle (20% dimethyl sulfoxide/80% propylene glycol) via a catheter attached to an Alzet osmotic minipump (24 hr pump, 8 ul/hr, 90 ul total volume).

Figure 2:
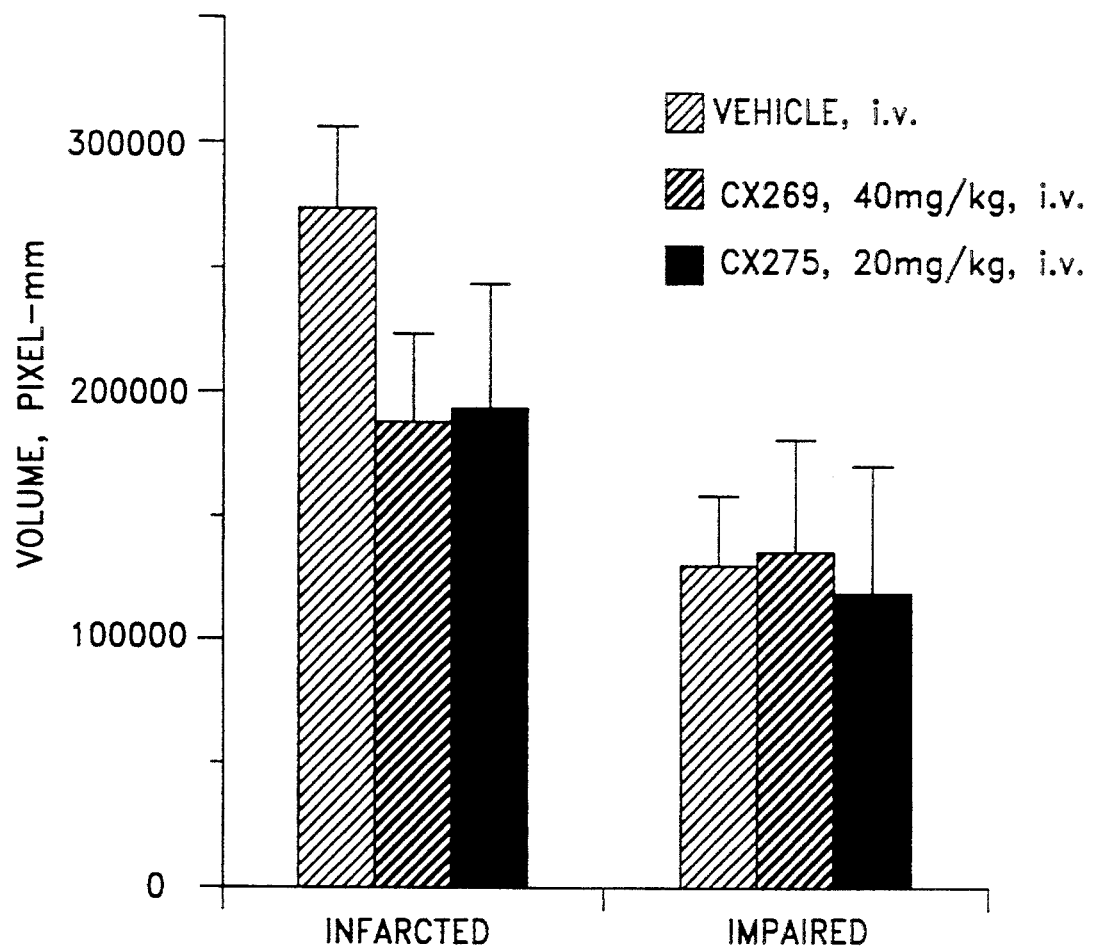
FIG. 2 graphically depicts the effects of Z-Leu-Phe-CONH-Et (CX269) and Z-Leu-Abu-CONH-Et (CX275) on the size of infarction produced upon MCA occlusion in male rats.

The model of Example 6 was used to determine the size of infarcted area for control (vehicle, i.v.) and with administration of each of two Calpain inhibitors: Z-Leu-Phe-CONH-Et (CX269) and Z-Leu-Abu-CONH-Et (CX275). These results are depicted graphically in FIG. 2. It can be seen that administration of either of the Calpain inhibitors Z-Leu-Phe-CONH-Et (CX269) or Z-Leu-Abu-CONH-Et(CX275) produces a reduction in the size of the infarcted area.

7. Inhibition of Anoxic and Hypoxic Damage

The CA1 region of hippocampus is a brain area particularly vulnerable to ischemic damage and other insults involving excitatory amino acids. The hippocampus is also a major focus of cell degeneration in Alzheimer's disease. Neural cells in slices degenerate following hypoxia through the same chain of events (including reperfusion effects) observed in vivo during and after ischemia. We believe that studies of degeneration of neural slices in the presence of the various Calpain Inhibitors is an effective indicator of the membrane permeance of the Calpain Inhibitors. Accordingly, we believe that these studies provide a model for the treatment and inhibition of neurodegeneration in vivo. Similar studies for determining the efficacy of compounds useful in the treatment of neurodegeneration in accordance with the present invention can be performed using other models, such as protection against degeneration in platelets or cells in culture.

It is believed that hypoxia is a major cause of neurotoxicity in a variety of neurodegenerative diseases and conditions, such as stroke and head injury. Thus, we conducted further studies using hippocampal slices to show that the various Calpain inhibitors, advantageously, can increase survival of hippocampal nerve cells during exposure to hypoxic or anoxic conditions. An initial screening procedure was first used to qualitatively determine whether the various Calpain Inhibitors can provide neuroprotection from anoxia in hippocampal slices. An example of these initial screening procedures is shown by Example 7A.

EXAMPLE 7A

Initial Screen for Inhibition of Anoxic Damage

Hippocampal slices (400 um) were prepared from Sprague Dawley rats (6 to 7 weeks) and maintained in an interface chamber at 35° C. using conventional techniques, i.e., the lower surface of the slice received a constant perfusion (0.5 ml/min) of ACSF, while the upper surface was exposed to a moist atmosphere of $O_2:CO_2$ (95%:5%) exchanged at a rate of 2 L/min. The ACSF medium contains (in mM): NaCl (124), KCl (3), $KHPO_4$ (2.5), $CaCl$ (3.4), $NaHCO_3$ (26) and D-Glucose (10). Field excitatory post-synaptic responses were recorded from stratum radiatum of CA1b in response to stimulation of Schaffer-commissural fibers in CA1a or CA1c. The depth of the recording electrode was optimized and evoked responses were collected at a rate of one evoked response every 30 seconds.

For the initial screening procedure, 14 to 16 slices are harvested from the hippocampus of a single rat and placed in a common ACSF bath. Each slice is tested in sequence to determine the magnitude of its pre-anoxic evoked response. Five stimulation pulses (each 0.1 ms (millisecond) in duration) were presented over a 15 second interval. The largest evoked response was noted and recorded for each slice.

Following this, the slices were incubated for one hour, with either drug or vehicle alone added to the ACSF. After the one hour drug incubation period, the oxygen-enriched atmosphere of the chamber was made anoxic by substituting nitrogen for oxygen ($N_2=95\%$; $CO^2=5\%$). The slices were retained in this anoxic environment for 10 minutes, following which the oxygen-enriched atmosphere ($O^2=95\%$; $CO_2=5\%$) was reestablished.

The slices were given the opportunity to recover for 30 minutes following reoxygenation whereupon each was stimulated and the maximum evoked potential determined, as described above during the pre-anoxia period. Those slices which, after anoxia, produced a maximum evoked potential of greater than 50% of that observed prior to anoxia were defined as surviving slices.

Figure 3:
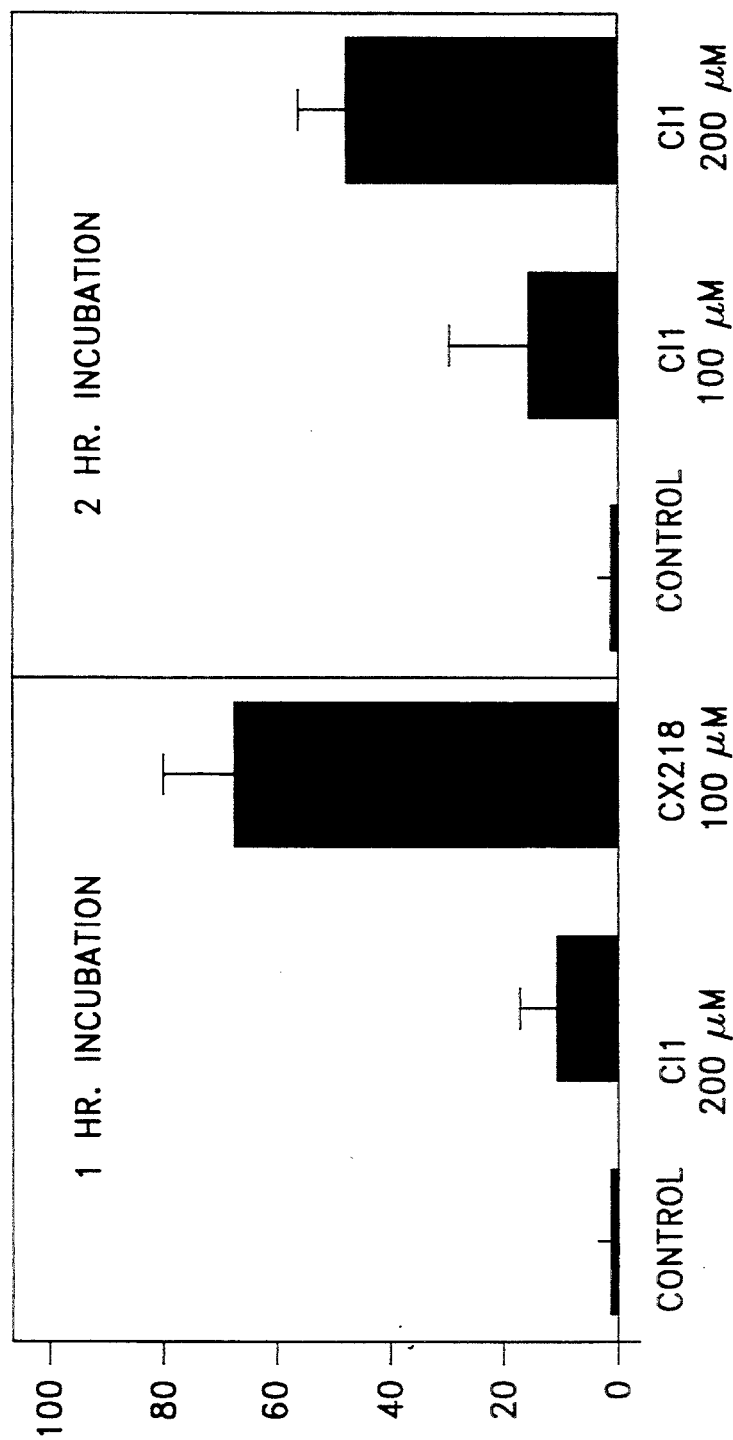
FIG. 3 shows the effects of CX216 (Z-Leu-Phe-CO2Et, a Peptide Keto-Compound), and CI1 (Ac-Leu-Leu-Nle-H) relative to control slices on survival of hippocampal slices exposed to 10 minutes exposure of anoxic atmosphere where both of these compounds were added at their optimal inhibitory concentration at both 1 hour and 2 hour incubation times.

Results of the studies of Example 7A are shown in FIG. 3. FIG. 3 shows the effects of CX218 (Z-Leu-Abu-CO2Et, a Peptide Keto-Compound), and CI1 relative to control slices on survival of hippocampal slices exposed to 10 minutes exposure of anoxic atmosphere. As seen in this figure, when the control slices are deprived of oxygen for 10 minutes in the absence of drug, virtually all fail to survive, as measured by their ability to elicit 50% of their pre-anoxia evoked response. In accordance with this finding, few if any recover upon reoxygenation. FIG. 3 also shows that when CI1 or CX218 are added to the ACSF, the slices are protected from the effects of anoxia, evidenced by a substantial proportion of slices eliciting evoked potentials.

Finally, it can be seen that CX218 is significantly more effective in protecting against anoxia and preventing degradation of slices at the minimal 1 hour incubation time, and at lower concentrations than CI1. This effect is believed to be due to the superior membrane permeance of the Peptide Keto-Compounds.

Table 7A shows further data from the studies of Example 7A.

TABLE 7A

PERCENT OF SLICES SURVIVING TEN MINUTES ANOXIA

| Compound | Dose (μM) | Incubation Time | Survival |
|---|---|---|---|
| Control | — | 1 hour | <1% |
| Leupeptin | 1000 | 3 hours | 50% |
| CI1 | 200 | 2 hours | 53% |
| CX13 (SHC) | 20 | 1 hour | 50% |
| CX89 (CKP) | 50 | 1 hour | 50% |
| CX218 (PKC) | 100 | 1 hour | 70% |

It can be seen from the data in Table 2 that all of the Calpain Inhibitors tested provide increased survival. CX13 (ACITIC, a Substituted Heterocyclic Compound (SHC)), CX89 (Boc-Gly-Leu-Phe-$CH_2Cl$, a Halo-Ketone Peptide (HKP)) and CX218 ((Z-Leu-Abu-CO2Et, a Peptide Keto-Compound (PKC)), are each shown to be highly effective in influencing survival times. Leupeptin is seen to be the least effective neuroprotective. Thus, we believe that CX13, CX89 and CX218 (Z-Leu-Abu-CO2Et) are more effective in influencing survival because of their membrane permeability. Accordingly, the results shown in Table 7A support our belief that Calpain Inhibitors with membrane permeability are effective neuroprotectants.

To further elucidate the ability of Calpain Inhibitors to provide neuroprotection to hippocampal slices, and to provide a more quantitative indication of the membrane permeability of these Calpain Inhibitors, we measured the effect of various Calpain Inhibitors on the evoked response on a single neuronal slice before, during and after anoxia. These studies are shown in Example 7B.

EXAMPLE 7B

Inhibition of Anoxic Damage

As in Example 7A, hippocampal slices (400 μm) were prepared from Sprague Dawley rats (6–7 weeks) and maintained in an interface chamber at 35° C. using conventional techniques, i.e. the lower surface of the slice received a constant perfusion (0.5 ml/min) of an artificial cerebrospinal fluid (ACSF), while the upper surface was exposed to a moist atmosphere of $O_2:CO_2$ (95%:5%) exchanged at a rate of 2 L/min. The ACSF medium contains (in mM): NaCl (124), KCl (3), $KHPO_4$ (1.25), $MgSO_4$ (2.5), $CaCl_2$ (3.4), $NaHCO_3$ (26) and D-Glucose (10). Field excitatory post-synaptic responses were recorded from stratum radiatum of CA1b in response to stimulation of Schaffer-commissural fibers in CA1a or CA1c. The depth of the recording electrode was optimized and evoked responses were collected at a rate of one evoked response every 30 seconds.

After establishing a stable baseline of evoked responses (approximately 10 minutes), ACSF containing Calpain Inhibitor was washed into the chamber and slices were incubated for a period of one hour. After incubation, evoked responses were again recorded and the change in the amplitude of the responses from baseline levels was noted. No effect of the inhibitors tested on baseline evoked responses was observed.

For anoxia experiments, incubation in the drug-containing medium was followed by replacement of the $O_2:CO_2$ (95%:5%) atmosphere with $N_2:CO_2$ (95%:5%). Slices were exposed to this anoxic environment until disappearance of the pre-synaptic fiber volley and for two minutes (severe anoxia) longer (total time in anoxic environment approximately 7–8 minutes in control case). Effects of Calpain Inhibitors on the functional recovery of the slices after the anoxic episode were then measured. Recovery of the evoked potential (EPSP) slope and amplitude by the drug treated slices can be compared to control slices to determine the relative efficacy of various Calpain Inhibitors.

Figure 4:
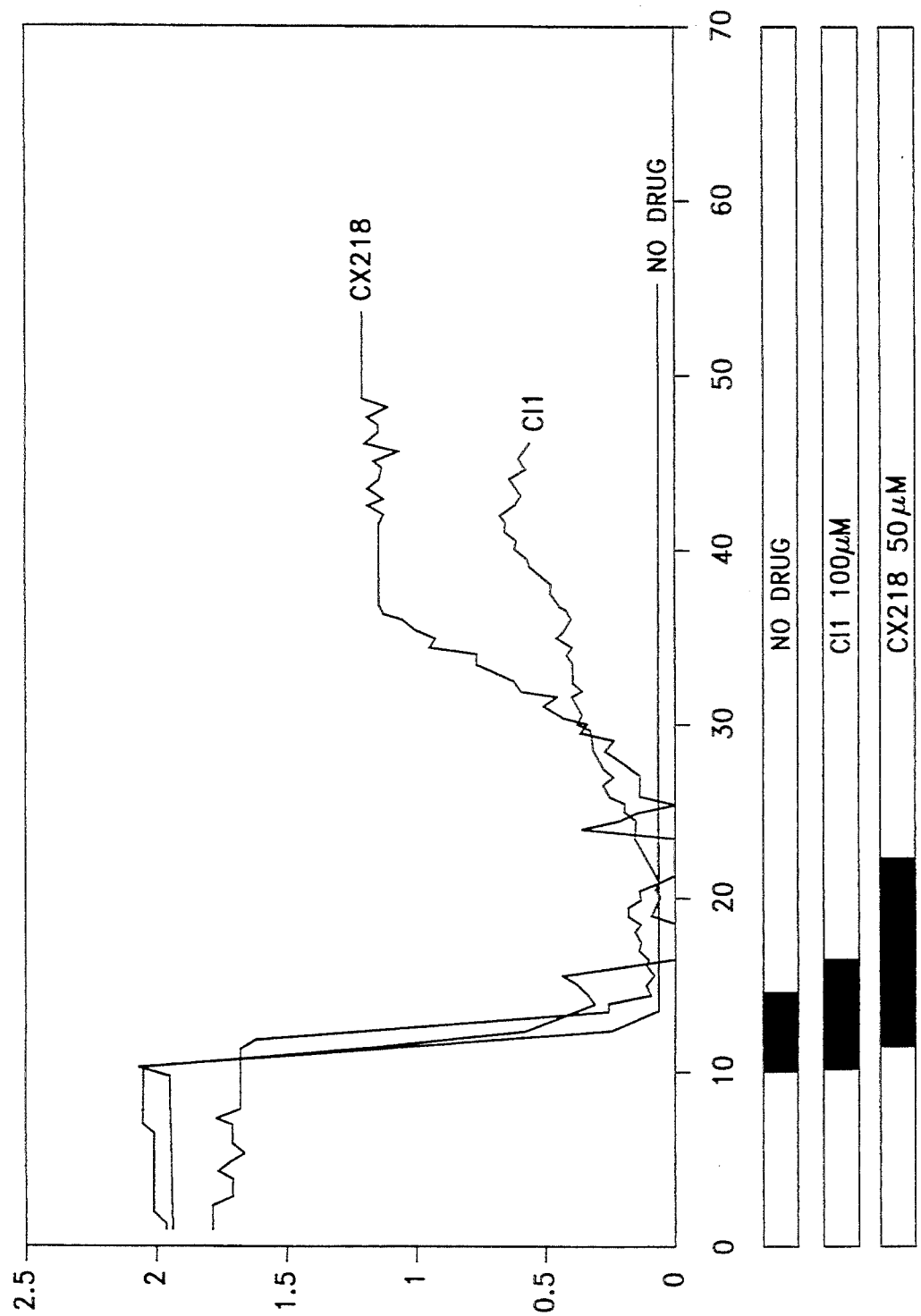
FIG. 4 shows the evoked potential amplitude for control, CI1 treated and CX218 treated hippocampal slices over a time course during which the slices are exposed to anoxic atmosphere.

FIG. 4 shows the EPSP amplitude in millivolts for control, CI1 treated and CX218 (a Peptide Keto-Compound) treated hippocampal slices in the studies of Example 7B. It can be seen in FIG. 4 that the control slices deprived of oxygen in the absence of drug display a gradual reduction of EPSP and abruptly lose fiber volley activity about 5–6 minutes after the beginning of anoxia. Reoxygenation at or before this point leads to complete functional recovery after about 20 minutes of reoxygenation, but reoxygenation after this point does not. In the latter case the recovered EPSP slope and amplitude become progressively reduced as the duration of anoxia post-fiber volley disappearance (post-FVD) increases. After severe anoxia (2 minutes post-FVD), slices recover only 15% of the EPSP slope.

In contrast to the control slices, recovery begins to occur shortly after the end of anoxia for the treated slices. FIG. 4 shows a comparison of the effects on EPSP amplitude produced in the presence of no inhibitor; the Peptide Keto-Compound, CX218, (Z-Leu-Abu-CO2Et) and CI1. CX218 produces a recovery from severe anoxia superior to that seen with CI1.

Figure 5:
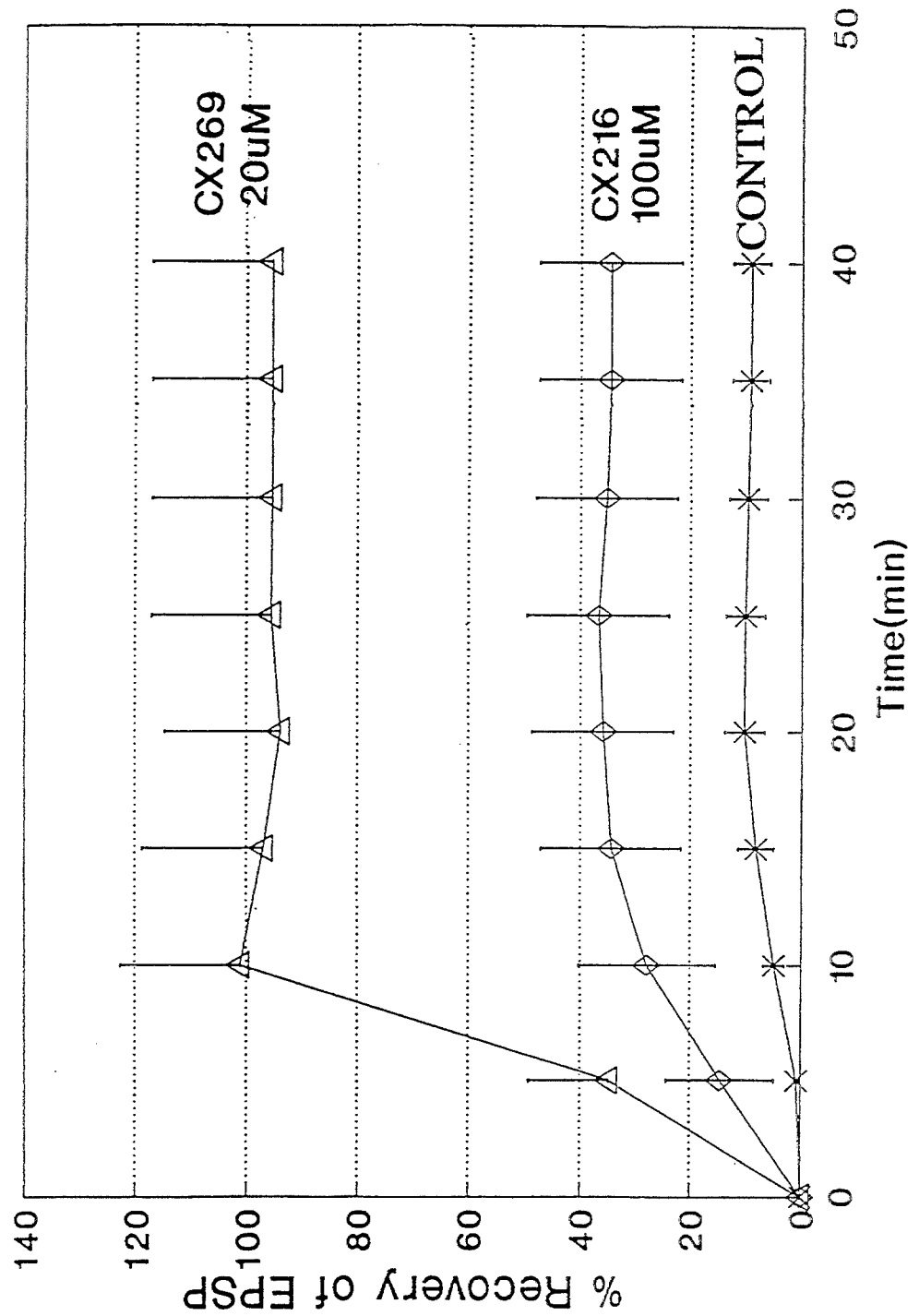
FIG. 5 shows the percent recovery of EPSP from severe hypoxia over the course of one hour incubation for Z-Leu-Phe-CONH-Et (CX269) and Z-Leu-Phe-CO2Et (CX216).

FIG. 5 shows the percent recovery of EPSP from severe hypoxia using the peptide ketoester CX 216 (Z-Leu-Phe-CO2Et) and its corresponding peptide ketoamide CX269 (Z-Leu-Phe-CONH-Et). These studies were performed in a manner similar to that of Example 7B, except using a hypoxic environment in place of the anoxia of Example 7B. It can be seen that use of the peptide ketoamide results in essentially complete (near 100%) recovery from hypoxia while the peptide ketoester produces a partial recovery. The control slices experienced little or no recovery.

Figure 6:
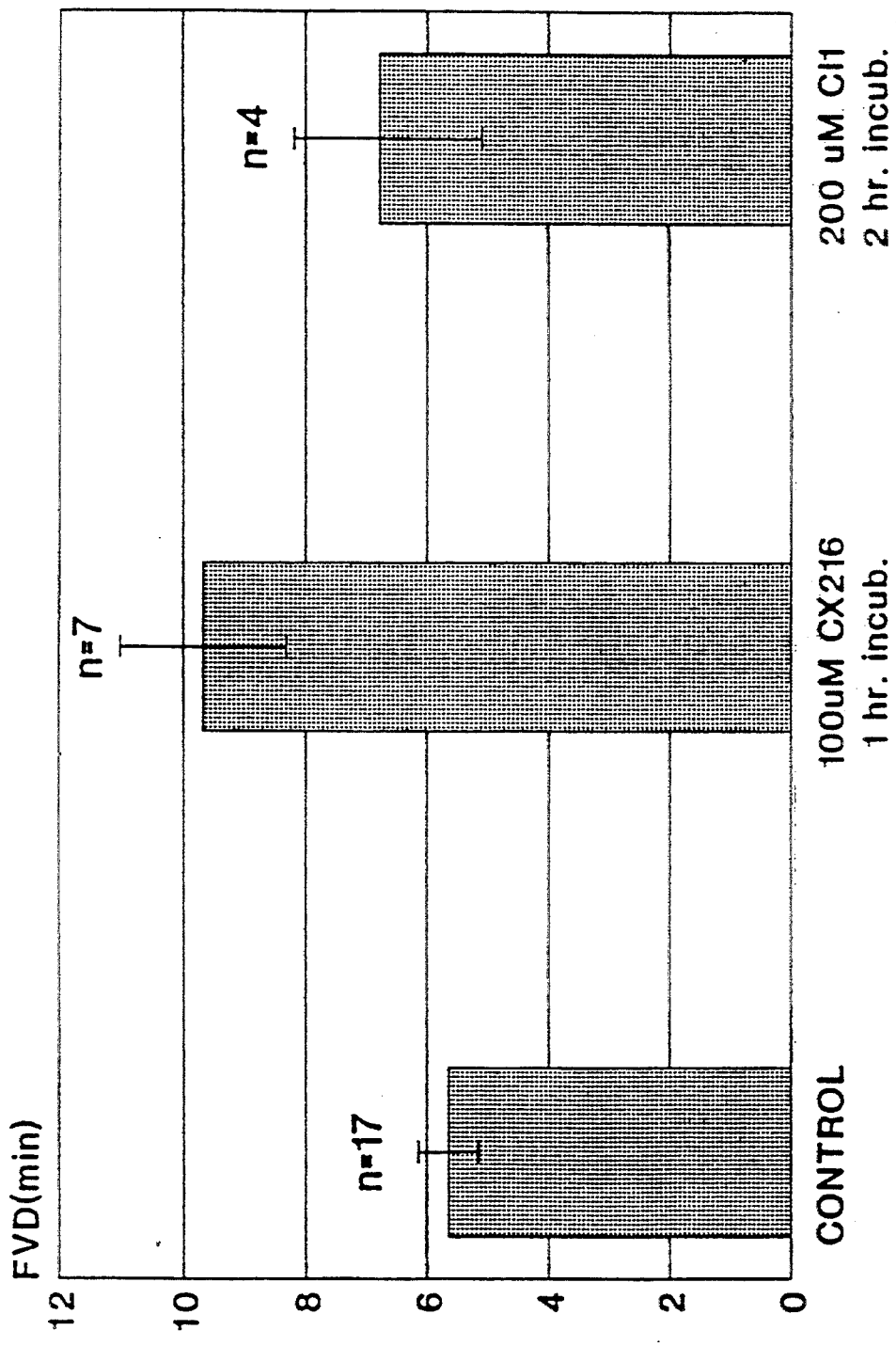
FIG. 6 shows a comparison of the effect of the presence of CI1 or CX216 on survival of hippocampal slices expressed as the duration of anoxia (in minutes) before fiber volley disappearance.

An interesting characteristic that we have discovered for certain Calpain Inhibitors is their ability to lengthen the period of exposure to anoxia required to produce fiber volley disappearance (FVD). Typically, under control anoxia conditions, fiber volley disappearance occurs in less than six minutes (FIG. 6). The Peptide Keto-Compound, CX-216, substantially lengthens the period of exposure to anoxia required to produce FVD. This is an important advantage of the use of this Peptide Keto-Compound for neuroprotection because slices can be expected to recover completely if reoxygenated before fiber volley disappearance. Thus, treatment with this Peptide Keto-Compound is expected to produce a greater percentage of recovery of cells from incipient neurodegenerative conditions. It is believed that other representatives of the Peptide Keto-Compounds as well as of other classes of Calpain Inhibitors also provide this effect.

Table 7B shows the percentage of recovery of pre-anoxia synaptic transmission (evoked potential amplitude) of slices treated with various Calpain Inhibitors or of control slices. All of these slices were exposed to ten minutes of anoxia according to the protocol of Example 7B.

TABLE 7B

PERCENT RECOVERY OF SYNAPTIC TRANSMISSION AFTER ANOXIA

| Compound | Concentration | % Recovery |
| --- | --- | --- |
| Control | — | 15 |
| CI1 | 200 | 35 |
| CX13 (SHC) | 20 | 60 |
| CX89 (CKP) | 50 | 30 |
| CX216 (PKC) | 100 | 38 |
| CX218 (PKC) | 100 | 55 |

The results shown in Table 7B provide further evidence that the peptide aldehyde, CI1, as well as the Substituted Heterocyclic Compounds, Peptide Keto-Compounds and Halo-Ketone Peptides are sufficiently membrane permeant to provide neuroprotection through Calpain inhibition.

CI1, which is at least partially membrane permeant, produces some effect, however, does not significantly lengthen the period of anoxia required to suppress electrical activity. Thus, compared to control, or even compared to leupeptin and CI1, the Substituted Heterocyclic Compounds, Peptide Keto-Compounds and Halo-Ketone Peptides can increase the degree of recovery after anoxic episodes while producing the additional advantage of extending the amount of time slices can tolerate anoxia (and thereby recover completely).

An important effect of the Peptide Keto-Compounds and other membrane permeant Calpain Inhibitors is that they are significantly more effective in lower doses than less permeable Calpain Inhibitors such as CI1. Although CI1 is shown to be at least somewhat membrane permeant due to its ability to affect slice survival, the more membrane-permeant inhibitors provide significantly increased protection. Thus, the more highly membrane-permeant Calpain Inhibitors are believed to be especially effective in treating and inhibiting neurodegeneration.

The results of the studies of Examples 7A and 7B show that the Substituted Heterocyclic Compounds, Peptide Keto-Compounds and Halo-Ketone Peptides are membrane-permeant Calpain Inhibitors which are believed to be especially effective in treating and inhibiting neurodegeneration. The results also show that Peptide Keto-Compounds, and perhaps representatives of other classes, can extend the duration of anoxia required to suppress electrical activity in hippocampal slices. As discussed above, these effects are important advantages of these compounds.

8. In Vivo Neuroprotection by Calpain Inhibitors

As discussed above, therapeutics useful for influencing the function of cells within the CNS must cross the BBB to reach their targets within the CNS. Non-BBB permeant compounds might, in addition to the brain infusion techniques described above, be administered via intraventricular administration, but this also severely limits their usefulness in practice. In order to test the in vivo effectiveness of the Calpain Inhibitors to cross the BBB and become therapeutically useful, we tested the ability of intraperitoneal injection of the Calpain Inhibitors to protect against excitotoxic damage in vivo. Protection was measured by evaluating changes in behavior of rats after injection with kainate. These studies are shown in Example 8A.

EXAMPLE 8A

Protection Against Behavioral Changes from Excitotoxic Damage by Peripherally Administered Calpain Inhibitors Rats (male Sprague-Dawley, 200±5 gms) were injected intraperitoneally with 12 mg/kg kainic acid in saline vehicle and ether 2001 µl DMSO (dimethylsulfoxide) or 4.6 mg calpain inhibitor dissolved in the same volume of DMSO. The rats were observed for six hours following the injections and the kainate-induced behavioral symptoms and convulsions scored on a scale of 0–6 (0=no symptoms; 1=wet dog shakes; 2=salivation and chewing; 3=at least one convulsive episode; 4=repeated or sustained convulsions; 5=convulsions, including rearing and falling; 6=convulsions followed by death within the 6 hrs post injection).

Figure 7:
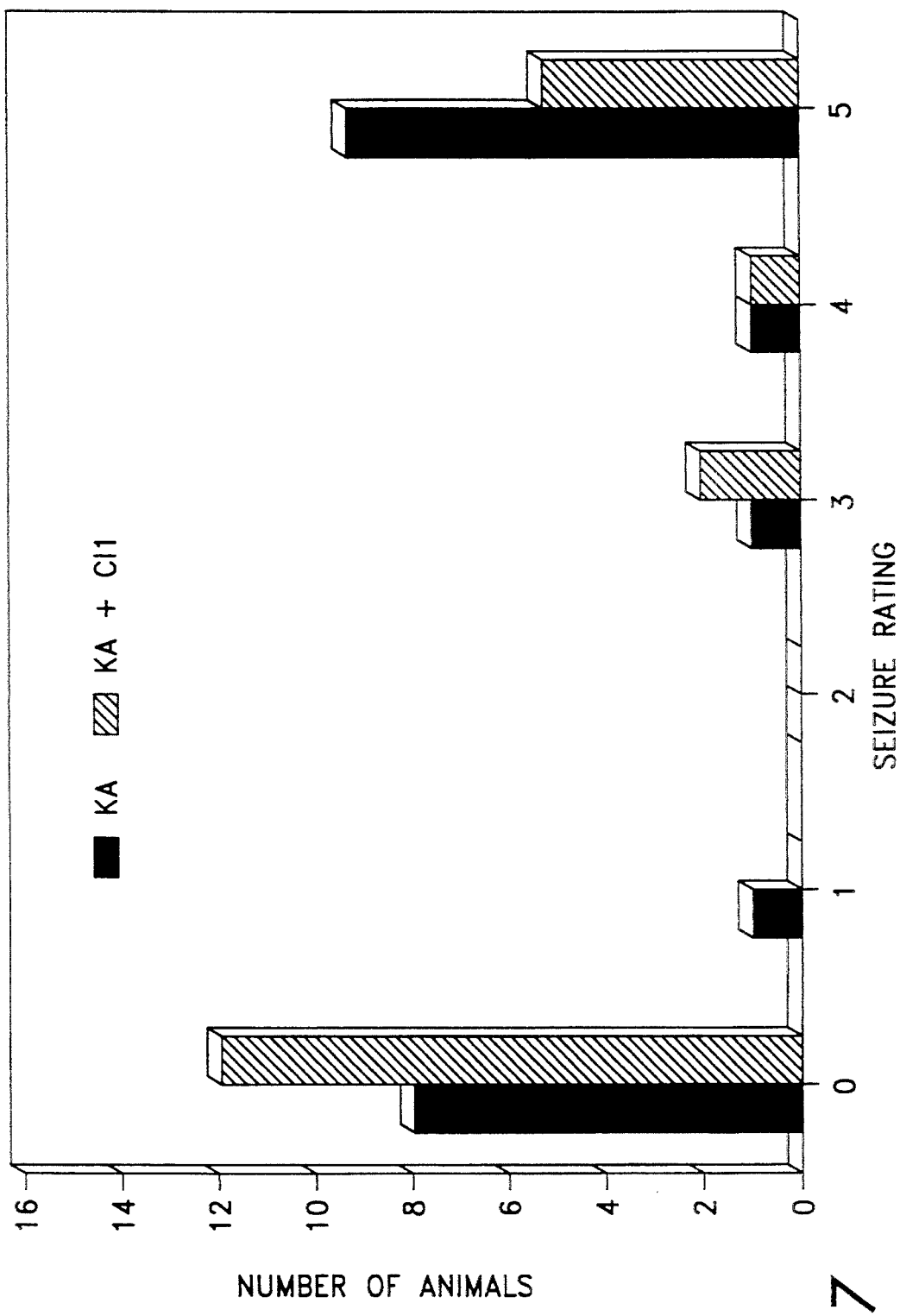
FIG. 7 shows the effects of CI1 compared with control on the behavioral and convulsive effects of kainic acid.

FIG. 7 shows the effects of CI1 on the behavioral and convulsive effects of kainic acid. In the control group, over haft the animals showed symptoms greater than mild behavioral symptoms, and many exhibited overt convulsions, presumably reflecting seizure activity within the brain. Unexpectedly, in the inhibitor treated group, the incidence and severity of convulsions was reduced. Thus, this data suggests that Calpain Inhibitors have an anti-convulsive effect. This effect is a distinct advantage in the use of Calpain Inhibitors in epilepsy-related neurodegenerative conditions and in stroke, which is often accompanied by seizures.

In order to more clearly demonstrate that the behavioral and anti-convulsive effects seen with the Calpain Inhibitors result from inhibition of Calpain we tested the brain tissues of the rats from Example 8A for accumulation of spectrin BDP's. As discussed above, these BDP's are associated with Calpain activity and with the neurodegeneration associated therewith.

EXAMPLE 8B

Protection Against Spectrin Breakdown from Excitotoxic Damage by Peripherally Administered Calpain Inhibitors Four days following the injection of kainate in the rats from Example 8A, the brains of the rats were removed and assayed for spectrin BDP's. Spectrin BDP's were assayed by homogenizing brain parts in 20 mM Tris pH=7.2, 0.32M sucrose, 501 µM Ac-Leu-Leu-nLeu-H on ice. Homogenates were mixed 1:1 with 10% SDS, 5% β-mercaptoethanol, 10% glycerol, 10 mM Tris pH=8.0, 0.5% bromophenolblue, heated to 95° C., and subjected to electrophoresis in 4½% polyacrylamide gels. The proteins in the gels were transferred to nitrocellulose and the spectrin and BDP's detected using a rabbit polyclonal anti-spectrin antibody and established immunodetection methods. The amount of spectrin and BDP's in each sample was quantitated by densitometric scanning of the developed nitrocellulose.

Figure 8:
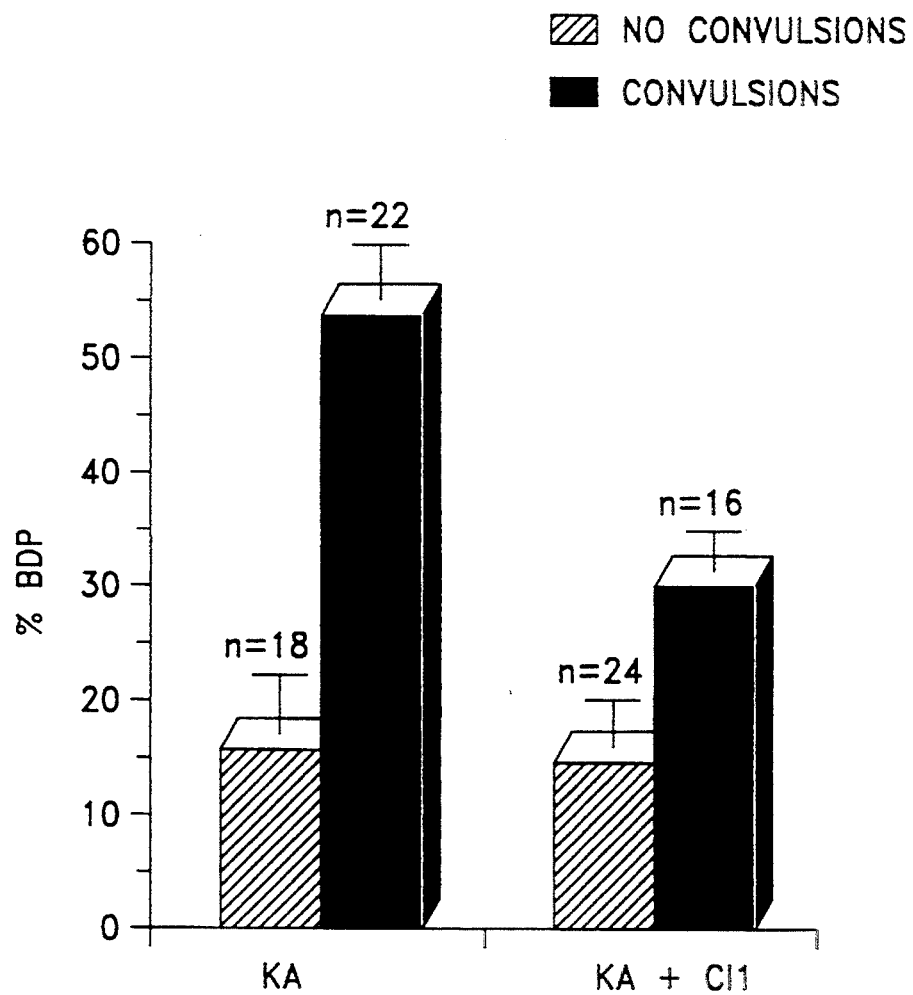
FIG. 8 shows the amount of spectrin BDP's in rat brains exposed to kainate for control and CI1 treated rats.

FIG. 8 shows the results of Example 8B. It can be seen that kainate stimulated the breakdown of spectrin in both Calpain Inhibitor treated and control rats. However, treated rats exhibited significantly less BDP's. These results verify that Calpain activity in the brains of the treated rats was reduced. An unexpected observation was that even those treated animals that exhibited severe seizures had significantly less spectrin breakdown than untreated animals subjected to kainate. Thus Calpain Inhibitor treatment reduced both the behavioral/convulsive effects of kainate and the activation of calpain in the most severely affected animals.

9. Conclusion

All of the foregoing studies support our discovery that Calpain Inhibitors provide in vivo protection against neurodegeneration associated with anoxia, excitotoxicity and other causes. Thus, these Calpain inhibitors possess neuroprotective activity against a variety of in vivo neurodegenerative diseases and conditions, including excitotoxicity, HIV-induced neuropathy, ischemia following denervation or injury, subarachnoid hemorrhage, stroke, multiple infarction dementia, Alzheimer's Disease (AD), Huntington's Disease, Parkinson's Disease, surgery-related brain damage and other pathological conditions.

Those Calpain Inhibitors which possess significant Calpain Inhibitory activity in vitro and also meet at least one of the foregoing or different tests for membrane permeability are excellent candidates for treatment of neurodegeneration.

G. DRUG DELIVERY

The ability of the various Calpain Inhibitors to penetrate plasma membranes is a significant advantage of these compounds from a pharmaceutical perspective. We believe that this ability, advantageously, allows the Calpain Inhibitors to provide excellent permeation of the blood-brain barrier. This is in contrast to many pharmaceuticals, especially peptides, which often exhibit poor permeation of the blood-brain barrier. Thus, we believe that the Calpain Inhibitors will exhibit excellent results as pharmaceutically neuroprotective agents.

For treatment of neurodegeneration, the Calpain Inhibitors can be administered orally, topically or parenterally. The term "parenteral" as used herein includes all non-oral delivery techniques including transdermal administration, subcutaneous injection, intravenous, intramuscular or intrasternal injection, intrathecal injection (directly into the CNS) or infusion techniques.

The dosage depends primarily on the specific formulation and on the object of the therapy or prophylaxis. The amount of the individual doses as well as the administration is best determined by individually assessing the particular case. However, in preferred compositions, the dosages of Calpain Inhibitors per day are preferably in the range of 1 µg/kg total body mass to 100 mg/kg total body mass, more preferably in the range of 10 µg/kg total body mass to 10 mg/kg total body mass.

The pharmaceutical compositions containing the active ingredient may be in a form suitable for oral use, for example as tablets, troches, lozenges, aqueous or oily suspensions, dispersible powders or granules, emulsions, hard or soft capsules or syrups or elixirs. The amount of active ingredient that may be combined with carrier materials to produce a single dosage form will vary depending upon the host treated and the particular mode of administration. However, typically, a single dose will contain sufficient Calpain Inhibitor to provide a complete day's dosage in a single orally acceptable form.

For injection, the therapeutic amount of the Calpain Inhibitors or their pharmaceutically acceptable salts will normally be made by subcutaneous injection, intravenous, intramuscular or intrasternal injection, or by intrathecal injection (directly into the brain). In order to provide a single day's dose with a single injection, the pharmaceutical compositions for parenteral administration will contain, in a single dosage form, from about 70 μg to about 7 g of Calpain Inhibitor per dose of from about 0.5 ml to about 1 liter of carrier solution. In addition to the active ingredient, these pharmaceutical compositions will usually contain a buffer, e.g. a phosphate buffer that keeps the pH in the range from 3.5 to 7 and also sodium chloride, and can also contain mannitol or sorbitol for adjusting the isotonic pressure. In a preferred form of these compositions, DMSO or other organic solvent is added in order to assist the introduction of the Calpain Inhibitor across membranes.

Additionally, lipids can be introduced into the pharmaceutical compositions in order to facilitate entry of the Calpain inhibitor compounds into tissue of the CNS. These compositions are prepared in accordance with methods known to those of skill in the art. Briefly, a lipid such as, phosphatidyl choline, cholesterol, other well-known lipid carrier or mixtures thereof, is mixed with the active compound along with a solvent, the solvent is dried off and the material reconstituted in saline. The compositions can also include other ingredients known to those of ordinary skill in the art, such as detergents, surfactants or emulsifying agents.

A composition for topical application or infusion can be formulated as an aqueous solution, lotion, jelly or an oily solution or suspension. A composition in the form of an aqueous solution is obtained by dissolving the Calpain Inhibitor in aqueous buffer solution of pH 4 to 6.5 and, if desired, adding a polymeric binder. An oily formulation for topical application is obtained by suspending the Calpain Inhibitor in an oil, optionally with the addition of a swelling agent such as aluminium stearate and/or a surfactant. The addition of DMSO to these topical compositions is believed to allow at least partial penetration of the active Calpain Inhibitor into the blood stream after application of the composition to the skin of a patient to allow for transdermal administration.

For treatment of neurodegeneration resulting from excitotoxicity, HIV-induced neuropathy, ischemia following denervation or injury, subarachnoid hemorrhage, stroke, multiple infarction dementia, Alzheimer's Disease (AD), Huntington's Disease, surgery-related brain damage, Parkinson's Disease, and other pathological conditions, the Calpain Inhibitors or pharmaceutically acceptable salts thereof may be administered orally or parenterally. The dosage depends primarily on the specific formulation and on the object of the therapy or prophylaxis. The amount of the individual doses as well as the administration is best determined by individually assessing the particular case.

In many acute neurodegenerative conditions and events, such as stroke and head injury, it is important to deliver the Calpain Inhibitor as soon after injury as is practicable. Thus, it is preferable to identify those individuals who have suffered stroke, head injury or other injury in which neurodegeneration is associated or is likely to occur, and to begin administration of a Calpain Inhibitor within 1 minute to 2 hours after the event, in order to prevent as much neurodegeneration as possible.

A particular application of the Calpain Inhibitors within the scope of the present invention is the application of these compounds during surgery to prevent neurodegeneration associated therewith. For example, for surgeries performed under general anesthesia, hypoxic conditions can occur through inadequate perfusion of the CNS while under anesthesia. Additionally, many major surgeries of the cardiovascular system require that a patient's heart be stopped and that perfusion be maintained through artificial means. In such surgeries, there is an increased danger of hypoxia occurring within the CNS, which can also result in neurodegeneration. Moreover, during neurosurgeries, there is an inherent risk of neurodegeneration resulting from inflammation, bleeding, hemorrhaging and the like. Such neurodegeneration can be inhibited by infusion with a solution containing Calpain Inhibitor. However, neurodegeneration resulting from neurosurgery can also be reduced prophylactically by administration of a Calpain Inhibitor through any of the foregoing administration techniques. Such administration is also believed to inhibit or prevent neurodegeneration associated with the use of anesthesia or with the use of artifical means of perfusion during major surgeries. A surgical patient can also have Calpain Inhibitor administered throughout surgery through intravenous drip.

The following examples are intended to illustrate certain neuroprotective uses of the Calpain Inhibitors within the scope of the present invention. As such, they are not meant to limit the invention in any way.

EXAMPLE 9

A Neuroprotective Composition for Intravenous Injection

| | |
|---|---|
| 500 μg | CH3CONH-CiTPrOIC from Example SHC2 |
| 4 ml | Propylene Glycol |
| 1 ml | DMSO |

EXAMPLE 10

A Neuroprotective Composition for Intravenous Drip.

| | |
|---|---|
| 250 mg | Z-Leu-Phe-CONH-Et from Example PKC 47 |
| 1000 ml | Phosphate Buffered Saline (pH 6.0) |
| 10 ml | DMSO |

EXAMPLE 11

A Neuroprotective Composition for Transdermal Application

| | |
|---|---|
| 25 mg | Z-Leu-DL-Abu-COOEt from Example PKC19 |
| 3 ml | Phosphate Buffered Saline (pH 6.0) |
| 2 ml | DMSO |

EXAMPLE 12

Neuroprotection after Head Injury

A first group of patients who are victims of head trauma is given 2 ml of the injectable composition of Example 9 intravenously within ten minutes of the time of injury. A second group of similarly matched patients does not receive the composition. The first group of patients exhibits markedly fewer and less severe outward symptoms of neurodegeneration, such as dementia, memory loss and paralysis.

EXAMPLE 13

Neuroprotection During Surgery

A patient about to undergo a triple bypass heart surgery is administered 500 ml of the composition of Example 10 per hour using an intravenous drip system. During surgery, the patient's heart is stopped and perfusion continued through artificial means. Although complications develop while restarting the heart and disconnecting the patient from the artificial means of perfusion, the patient becomes conscious within several hours of surgery. Within a few days, the patient's mental status is normal with no indications of neurodegeneration.

It will be appreciated that certain variations may suggest themselves to those skilled in the art. The foregoing detailed description is to be clearly understood as given by way of illustration, the spirit and scope of this invention being interpreted through reference to the appended claims.

What is claimed is:

1. A method of treating neurodegeneration due to ischemia in a mammalian patient, comprising the steps of:
   selecting a patient who is experiencing or who has experienced neurodegeneration due to ischemia;
   monitoring said patient for indicia of the onset or existence of neurodegeneration due to ischemia; detecting said indicia; and
   in response to the detecting of any such indicia of the onset or existence of neurodegeneration due to ischemia, administering to said patient a therapeutically efficacious amount of a Peptide Ketoamide compound, or a pharmaceutically acceptable salt thereof, together with a pharmaceutically acceptable carrier, said Peptide Ketoamide compound having the general formula $M-(aa)_n-CO-Q-R$, wherein:
   M is selected from the group consisting of NH2—CO—, NH2—CS—, NH2—SO2—, X—NH—CO—, X—NH—CS—, X—NH—SO2—, X—CO—, X—CS—, X—SO2—, X—O—CO—, X—O—CS—, H, acetyl, carbobenzoxy ("Z"), succinyl, methyloxysuccinyl, and butyloxycarbonyl;
   X is selected from the group consisting of C1-6 alkyl, C1-6 fluoroalkyl, C1-6 alkyl substituted with J, C1-6 fluoroalkyl substituted with J, 1-admantyl, 9-fluorenyl, phenyl, phenyl substituted with K, phenyl disubstituted with K, phenyl trisubstituted with K, naphthyl, naphthyl substituted with K, naphthyl disubstituted with K, naphthyl trisubstituted with K, C1-6 alkyl with an attached phenyl group, C1-6 alkyl with two attached phenyl groups, C1-6 alkyl with an attached phenyl group substituted with K, and C1-6 alkyl with two attached phenyl groups substituted with K;
   J is selected from the group consisting of halogen, COOH, OH, CN, NO2, NH2, C1-6 alkoxy, C1-6 alkylamine, C1-6 dialkylamine, C1-6 alkyl-O—CO—, C1-6 alkyl-O—CO—NH, and C1-6 alkyl-S—;
   K is selected from the group consisting of halogen, C1-6 alkyl, C1-6 perfluoroalkyl, C1-6 alkoxy, NO2, CN, OH, CO2H, amino, C1-6 alkylamino, C2-12 dialkylamino, C1-6 acyl, C1-6 alkoxy-CO—, and C1-6 alkyl-S—;
   aa is a blocked or unblocked amino acid of the L or D configuration selected from the group consisting of alanine, valine, leucine, isoleucine, proline, methionine, methionine sulfoxide, phenylalanine, tryptophan, glycine, serine, threonine, cysteine, tyrosine, asparagine, glutamine, aspartic acid, glutamic acid, lysine, arginine, histidine, phenylglycine, beta-alanine, norleucine (nle), norvaline (nva), alpha-aminobutyric acid (abu), epsilon-aminocaproic acid, citrulline, hydroxyproline, homoarginine, ornithine and sarcosine;
   n is a number from 1 to 20;
   Q is NH; and
   R is selected from the group consisting of H, C1-6 alkyl, C1-6 fluoroalkyl, C1-6 chloroalkyl, benzyl, C1-6 alkyl substituted with phenyl, and C1-6 alkyl with an attached phenyl group substituted with K.

2. A method as in claim 1, wherein the selecting step comprises selecting a patient who is experiencing or who has experienced ischemia caused by a medical condition, said condition being selected from the group consisting of stroke, head injury, major heart attack, brain seizure, multiple infarct dementia, subarachnoid hemorrhage, and surgery.

3. The method of claim 1, wherein n is 1.
4. The method of claim 1, wherein n is 2.
5. The method of claim 1, wherein n is 3.
6. The method of claim 1, wherein n is 4.

7. A method of inhibiting or treating neurodegeneration due to ischemia in a mammal, comprising administering to said mammal a therapeutically efficacious amount of a Peptide Ketoamide compound that has Calpain inhibitory activity or a pharmaceutically acceptable salt thereof, said Peptide Ketoamide compound having the general formula $M-(aa)_n-CO-Q-R$, wherein:
   M is selected from the group consisting of NH2—CO—, NH2—CS—, NH2—SO2—, X—NH—CO—, X—NH—CS—, X—NH—SO2—, X—CO—, X—CS—, X—SO2—, X—O—CO—, X—O—CS—, H, acetyl, carbobenzoxy ("Z"), succinyl, methyloxysuccinyl, and butyloxycarbonyl;
   X is selected from the group consisting of C1-6 alkyl, C1-6 fluoroalkyl, C1-6 alkyl substituted with J, C1-6 fluoroalkyl substituted with J, 1-admantyl, 9-fluorenyl, phenyl, phenyl substituted with K, phenyl disubstituted with K, phenyl trisubstituted with K, naphthyl, naphthyl substituted with K, naphthyl disubstituted with K, naphthyl trisubstituted with K, C1-6 alkyl with an attached phenyl group, C1-6 alkyl with two attached phenyl groups, C1-6 alkyl with an attached phenyl group substituted with K, and C1-6 alkyl with two attached phenyl groups substituted with K;
   J is selected from the group consisting of halogen, COOH, OH, CN, NO2, NH2, C1-6 alkoxy, C1-6 alkylamine, C1-6 dialkylamine, C1-6 alkyl-O—CO—, C1-6 alkyl-O—CO—NH, and C1-6 alkyl-S—;
   K is selected from the group consisting of halogen, C1-6 alkyl, C1-6 perfluoroalkyl, C1-6 alkoxy, NO2, CN, OH, CO2H, amino, C1-6 alkylamino, C2-12 dialkylamino, C1-C6 acyl, C1-6 alkoxy-CO—, and C1-6 alkyl-S—;

aa is a blocked or unblocked amino acid of the L or D configuration selected from the group consisting of alanine, valine, leucine, isoleucine, proline, methionine, methionine sulfoxide, phenylalanine, tryptophan, glycine, serine, threonine, cysteine, tyrosine, asparagine, glutamine, aspartic acid, glutamic acid, lysine, arginine, histidine, phenylglycine, beta-alanine, norleucine (nle), norvaline (nva), alpha-aminobutyric acid (abu), epsilon-aminocaproic acid, citrulline, hydroxyproline, homoarginine, ornithine and sarcosine;

n is a number from 1 to 20;

Q is NH; and

R is selected from the group consisting of H, C1-6 alkyl, C1-6 fluoroalkyl, C1-6 chloroalkyl, benzyl, C1-6 alkyl substituted with phenyl, and C1-6 alkyl with an attached phenyl group substituted with K.

8. The method of claim 7, additionally comprising the step of identifying, prior to the administration of said compound, a mammal in which neurodegeneration of the CNS due to ischemia is occurring or has occurred.

9. The method of claim 7, wherein the neurodegeneration due to ischemia is associated with a condition selected from the group consisting of subarachnoid hemorrhage, stroke, brain seizure, major heart attack, multiple infarct dementia, surgery, and head injury.

10. The method of claim 7, wherein the administering step comprises parenteral administration of said compound in a pharmaceutically acceptable carrier.

11. The method of claim 10, wherein the administering step comprises transdermal administration, subcutaneous injection, intravenous, intramuscular or intrasternal injection, intrathecal injection directly into the CNS or infusion techniques.

12. The method of claim 7, wherein the administering step comprises oral administration of said compound in a form suitable for oral use.

13. The method of claim 7, wherein n is 1.

14. The method of claim 7, wherein n is 2.

15. The method of claim 7, wherein n is 3.

16. The method of claim 7, wherein n is 4.

17. A method of intervening early in the process of neurodegeneration due to ischemia occurring in the neural tissue of a mammal comprising administering to said mammal a pharmaceutically acceptable form of a Peptide α-Ketoacid selected from the group consisting of Bz-DL-Lys-COOH and Bz-DL-Ala-COOH.

18. The method of claim 17, wherein said neurodegeneration due to ischemia is associated with a medical condition selected from the group consisting of stroke, head injury, major heart attack, brain seizure, surgery, multiple infarct dementia, and subarachnoid hemorrhage.

19. A method of intervening early in the process of neurodegeneration due to ischemia occurring in the neural tissue of a mammal comprising administering to said mammal a pharmaceutically acceptable form of a Peptide Ketoester or a pharmaceutically acceptable salt thereof, said Peptide Ketoester having the formula M-(aa)$_n$—CO—Q—R, wherein:

M is selected from the group consisting of NH2—CO—, NH2—CS—, NH2—SO2—, X—NH—CO—, X—NH—CS—, X—NH—SO2—, X—CO—, X—CS—, X—SO2—, X—O—CO—, X—O—CS—, H, acetyl, carbobenzoxy ("Z"), succinyl, methyloxysuccinyl, and butyloxycarbonyl;

X is selected from the group consisting of C1-6 alkyl, C1-6 fluoroalkyl, C1-6 alkyl substituted with J, C1-6 fluoroalkyl substituted with J, 1-admantyl, 9-fluorenyl, phenyl, phenyl substituted with K, phenyl disubstituted with K, phenyl trisubstituted with K, naphthyl, naphthyl substituted With K, naphthyl disubstituted with K, naphthyl trisubstituted with K, C1-6 alkyl with an attached phenyl group, C1-6 alkyl with two attached phenyl groups, C1-6 alkyl with an attached phenyl group substituted with K, and C1-6 alkyl with two attached phenyl groups substituted with K;

J is selected from the group consisting of halogen, COOH, OH, CN, NO2, NH2, C1-6 alkoxy, C1-6 alkylamine, C1-6 dialkylamine, C1-6 alkyl-O—CO—, C1-6 alkyl-O—CO—NH, and C1-6 alkyl-S—;

K is selected from the group consisting of halogen, C1-6 alkyl, C1-6 perfluoroalkyl, C1-6 alkoxy, NO2, CN, OH, CO2H, amino, C1-6 alkylamino, C2-12 diakylamino, C1-C6 acyl, C1-6 alkoxy-CO—, and C1-6 alkyl-S—;

aa is a blocked or unblocked amino acid of the L or D configuration selected from the group consisting of alanine, valine, leucine, isoleucine, proline, methionine, methionine sulfoxide, phenylalanine, tryptophan, glycine, serine, threonine, cysteine, tyrosine, asparagine, glutamine, aspartic acid, glutamic acid, lysine, arginine, histidine, phenylglycine, beta-alanine, norleucine (nle), norvaline (nva), alpha-aminobutyric acid (abu), epsilon-aminocaproic acid, citrulline, hydroxyproline, homoarginine, ornithine and sarcosine;

n is 1;

Q is O; and

R is selected from the group consisting of H, C1-6 alkyl, C1-6 fluoroalkyl, C1-6 chloroalkyl, benzyl, C1-6 alkyl substituted with phenyl, and C1-6 alkyl with an attached phenyl group substituted with K.

20. The method of claim 19, wherein said neurodegeneration due to ischemia is associated with a medical condition selected from the group consisting of stroke, head injury, major heart attack, brain seizure, surgery, multiple infarct dementia, and subarachnoid hemorrhage.

21. A method of intervening early in the process of neurodegeneration due to ischemia occurring in the neural tissue of a mammal comprising administering to said mammal a pharmaceutically acceptable form of a Peptide Ketoester or a pharmaceutically acceptable salt thereof, said Peptide Ketoester having the formula M-(aa)$_n$CO—Q—R, wherein:

M is selected from the group consisting of NH2—CO—, NH2—CS—, NH2—SO2—, X—NH—CO—, X—NH—CS—, X—NH—SO2—, X—CO—, X—CS—, X—SO2—, X—O—CO—, X—O—CS—, H, acetyl, carbobenzoxy ("Z"), succinyl, methyloxysuccinyl, and butyloxycarbonyl;

X is selected from the group consisting of C1-6 alkyl, C1-6 fluoroalkyl, C1-6 alkyl substituted with J, C1-6 fluoroalkyl substituted with J, 1-admantyl, 9-fluorenyl, phenyl, phenyl substituted with K, phenyl disubstituted with K, phenyl trisubstituted with K, naphthyl, naphthyl substituted with K, naphthyl disubstituted with K, naphthyl trisubstituted with K, C1-6 alkyl with an attached phenyl group, C1-6 alkyl with two attached phenyl groups, C1-6 alkyl with an attached phenyl group substituted with K, and C1-6 alkyl with two attached phenyl groups substituted with K;

J is selected from the group consisting of halogen, COOH, OH, CN, NO2, NH2, C1-6 alkoxy, C1-6 alkylamine, C1-6 dialkylamine, C1-6 alkyl-O—CO—, C1-6 alkyl-O—CO—NH, and C1-6 alkyl-S—;

K is selected from the group consisting of halogen, C1-6 alkyl, C1-6 perfluoroalkyl, C1-6 alkoxy, NO2, CN, OH, CO2H, amino, C1-6 alkylamino, C2-12 dialkylamino, C1-C6 acyl, C1-6 alkoxy-CO—, and C1-6 alkyl-S—;

aa is a blocked or unblocked amino acid of the L or D configuration selected from the group consisting of alanine, valine, leucine, isoleucine, proline, methionine, methionine sulfoxide, phenylalanine, tryptophan, glycine, serine, threonine, cysteine, tyrosine, asparagine, glutamine, aspartic acid, glutamic acid, lysine, arginine, histidine, phenylglycine, beta-alanine, norleucine (nle), norvaline (nva), alpha-aminobutyric acid (abu), epsilon-aminocaproic acid, citrulline, hydroxyproline, homoarginine, ornithine and sarcosine;

n is 2;

Q is O; and

R is selected from the group consisting of H, C1-6 alkyl, C1-6 fluoroalkyl, C1-6 chloroalkyl, benzyl, C1-6 alkyl substituted with phenyl, and C1-6 alkyl with an attached phenyl group substituted with K.

22. The method of claim 21, wherein the peptide ketoester is selected from the group consisting of Z-Leu-Nva-COOEt, Z-Leu-Nle-COOEt, Z-Leu-Abu-COOEt, Z-Leu-Met-COOEt, Z-Leu-Phe-COOEt, and MeO-Suc-Ala-DL-Ala-COOMe.

23. The method of claim 21, wherein said neurodegeneration due to ischemia is associated with a medical condition selected from the group consisting of stroke, head injury, major heart attack, brain seizure, surgery, multiple infarct dementia, and subarachnoid hemorrhage.

24. A method of intervening early in the process of neurodegeneration due to ischemia occurring in the neural tissue of a mammal comprising administering to said mammal a pharmaceutically acceptable form of a Peptide Ketoester or a pharmaceutically acceptable salt thereof, said Peptide Ketoester having the formula M-(aa)$_n$—CO—Q—R, wherein:

M is selected from the group consisting of NH2—CO—, NH2—CS—, NH2—SO2—, X—NH—CO—, X—NH—CS—, X—NH—SO2—, X—CO—, X—CS—, X—SO2—, X—O—CO—, X—O—CS—, H, acetyl, carbobenzoxy ("Z") , succinyl, methyloxysuccinyl, and butyloxycarbonyl;

X is selected from the group consisting of C1-6 alkyl, C1-6 fluoroalkyl, C1-6 alkyl substituted with J, C1-6 fluoroalkyl substituted with J, 1-admantyl, 9-fluorenyl, phenyl, phenyl substituted with K, phenyl disubstituted with K, phenyl trisubstituted with K, naphthyl, naphthyl substituted with K, naphthyl disubstituted with K, naphthyl trisubstituted with K, C1-6 alkyl with an attached phenyl group, C1-6 alkyl with two attached phenyl groups, C1-6 alkyl with an attached phenyl group substituted with K, and C1-6 alkyl with two attached phenyl groups substituted with K;

J is selected from the group consisting of halogen, COOH, OH, CN, NO2, NH2, C1-6 alkoxy, C1-6 alkylamine, C1-6 dialkylamine, C1-6 alkyl-O—CO—, C1-6 alkyl-O—CO—NH, and C1-6 alkyl-S—;

K is selected from the group consisting of halogen, C1-6 alkyl, C1-6 perfluoroalkyl, C1-6 alkoxy, NO2, CN, OH, CO2H, amino, C1-6 alkylamino, C2-12 dialkylamino, C1-C6 acyl, C1-6 alkoxy-CO—, and C1-6 alkyl-S—;

aa is a blocked or unblocked amino acid of the L or D configuration selected from the group consisting of alanine, valine, leucine, isoleucine, proline, methionine, methionine sulfoxide, phenylalanine, tryptophan, glycine, serine, threonine, cysteine, tyrosine, asparagine, glutamine, aspartic acid, glutamic acid, lysine, arginine, histidine, phenylglycine, beta-alanine, norleucine (nle), norvaline (nva), alpha-aminobutyric acid (abu), epsilon-aminocaproic acid, citrulline, hydroxyproline, homoarginine, ornithine and sarcosine;

n is 3;

Q is O; and

R is selected from the group consisting of H, C1-6 alkyl, C1-6 fluoroalkyl, C1-6 chloroalkyl, benzyl, C1-6 alkyl substituted with phenyl, and C1-6 alkyl with an attached phenyl group substituted with K.

25. The method of claim 24, wherein the Peptide Ketoester is selected from the group consisting of Z-Ala-Ala-DL-Ala-COOEt, Z-Ala-Pro-DL-Ala-COOEt, Z-Ala-Ala-DL-Abu-COOEt, Z-Ala-Ala-DL-Abu-COOBzl, and MeO-Suc-Val-Pro-DL-Phe-COOMe.

26. The method of claim 24, wherein said neurodegeneration due to ischemia is associated with a medical condition selected from the group consisting of stroke, head injury, major heart attack, brain seizure, surgery, multiple infarct dementia, and subarachnoid hemorrhage.

27. A method of intervening early in the process of neurodegeneration due to ischemia occurring in the neural tissue of a mammal comprising administering to said mammal a pharmaceutically acceptable form of a Peptide Ketoester or a pharmaceutically acceptable salt thereof, said Peptide Ketoester having the formula M-(aa)$_n$—CO—Q—R, wherein:

M is selected from the group consisting of NH2—CO—, NH2—CS—, NH2—SO2—, X—NH—CO—, X—NH—CS—, X—NH—SO2—, X—CO—, X—CS—, X—SO2—, X—O—CO—, X—O—CS—, H, acetyl, carbobenzoxy ("Z"), succinyl, methyloxysuccinyl, and butyloxycarbonyl;

X is selected from the group consisting of C1-6 alkyl, C1-6 fluoroalkyl, C1-6 alkyl substituted with J, C1-6 fluoroalkyl substituted with J, 1-admantyl, 9-fluorenyl, phenyl, phenyl substituted with K, phenyl disubstituted with K, phenyl trisubstituted with K, naphthyl, naphthyl substituted with K, naphthyl disubstituted with K, naphthyl trisubstituted with K, C1-6 alkyl with an attached phenyl group, C1-6 alkyl with two attached phenyl groups, C1-6 alkyl with an attached phenyl group substituted with K, and C1-6 alkyl with two attached phenyl groups substituted with K;

J is selected from the group consisting of halogen, COOH, OH, CN, NO2, NH2, C1-6 alkoxy, C1-6 alkylamine, C1-6 dialkylamine, C1-6 alkyl-O—CO—, C1-6 alkyl-O—CO—NH, and C1-6 alkyl-S—;

K is selected from the group consisting of halogen, C1-6 alkyl, C1-6 perfluoroalkyl, C1-6 alkoxy, NO2, CN, OH, CO2H, amino, C1-6 alkylamino, C2–12 dialkylamino, C1–C6 acyl, C1–6 alkoxy-CO—, and C1–6 alkyl-S—;

aa is a blocked or unblocked amino acid of the L or D configuration selected from the group consisting of alanine, valine, leucine, isoleucine, proline, methionine, methionine sulfoxide, phenylalanine, tryptophan, glycine, serine, threonine, cysteine, tyrosine, asparagine, glutamine, aspartic acid, glutamic acid, lysine, arginine, histidine, phenylglycine, beta-alanine, norleucine (nle), norvaline (nva), alpha-aminobutyric acid (abu), epsilon-aminocaproic acid, citrulline, hydroxyproline, homoarginine, ornithine and sarcosine;

n is 4;

Q is O; and

R is selected from the group consisting of H, C1–6 alkyl, C1–6 fluoroalkyl, C1–6 chloroalkyl, benzyl, C1–6 alkyl substituted with phenyl, and C1–6 alkyl with an attached phenyl group substituted with K.

28. The method of claim 27, wherein the peptide ketoester is selected from the group consisting of MeO-Suc-Ala-Ala-Pro-DL-Abu-COOMe and Z-Ala-Ala-Ala-DL-Ala-COOEt.

29. The method of claim 27, wherein said neurodegeneration due to ischemia is associated with a medical condition selected from the group consisting of stroke, head injury, major heart attack, brain seizure, surgery, multiple infarct dementia, and subarachnoid hemorrhage.

30. A method of intervening early in the process of neurodegeneration due to ischemia occurring in the neural tissue of a mammal comprising administering to said mammal a pharmaceutically acceptable form of a Peptide α-Ketoamide or a pharmaceutically acceptable salt thereof, said Peptide Ketoamide compound having the general formula $M\text{-}(aa)_n\text{—}CO\text{—}Q\text{—}R$, wherein:

M is selected from the group consisting of NH2—CO—NH2—CS—, NH2—SO2—, X—NH—CO—, X—NH—CS—, X—NH—SO2—, X—CO—, X—CS—, X—SO2—, X—O—CO—, X—O—CS—, H, acetyl, carbobenzoxy ("Z"), succinyl, methyloxysuccinyl, and butyloxycarbonyl;

X is selected from the group consisting of C1–6 alkyl, C1–6 fluoroalkyl, C1–6 alkyl substituted with J, C1–6 fluoroalkyl substituted with J, 1-admantyl, 9-fluorenyl, phenyl, phenyl substituted with K, phenyl disubstituted with K, phenyl trisubstituted with K, naphthyl, naphthyl substituted with K, naphthyl disubstituted with K, naphthyl trisubstituted with K, C1–6 alkyl with an attached phenyl group, C1–6 alkyl with two attached phenyl groups, C1–6 alkyl with an attached phenyl group substituted with K, and C1–6 alkyl with two attached phenyl groups substituted with K;

J is selected from the group consisting of halogen, COOH, OH, CN, NO2, NH2, C1–6 alkoxy, C1–6 alkylamine, C1–6 dialkylamine, C1–6 alkyl-O—CO—, C1–6 alkyl-O—CO—NH, and C1–6 alkyl-S—;

K is selected from the group consisting of halogen, C1–6 alkyl, C1–6 perfluoroalkyl, C1–6 alkoxy, NO2, CN, OH, CO2H, amino, C1–6 alkylamino, C2–12 dialkylamino, C1–C6 acyl, C1–6 alkoxy-CO—, and C1–6 alkyl-S—;

aa is a blocked or unblocked amino acid of the L or D configuration selected from the group consisting of alanine, valine, leucine, isoleucine proline, methionine, methionine sulfoxide, phenylalanine, tryptophan, glycine, serine, threonine, cysteine, tyrosine, asparagine, glutamine, aspartic acid, glutamic acid, lysine, arginine, histidine, phenylglycine, beta-alanine, norleucine (nle), norvaline (nva) alpha-aminobutyric acid (abu), epsilon-aminocaproic acid, citrulline, hydroxyproline, homoarginine, ornithine and sarcosine;

n is a number from 1 to 20;

Q is NH; and

R is selected from the group consisting of H, C1–6 alkyl, C1–6 fluoroalkyl, C1–6 chloroalkyl, benzyl, C1–6 alkyl substituted with phenyl, and C1–6 alkyl with an attached phenyl group substituted with K.

31. The method of claim 30, wherein n is 1.
32. The method of claim 30, wherein n is 2.
33. The method of claim 30, wherein n is 3.
34. The method of claim 30, wherein n is 4.
35. The method of claim 30, wherein said neurodegeneration due to ischemia is associated with a medical condition selected from the group consisting of stroke, head injury, major heart attack, brain seizure, surgery, multiple infarct dementia, and subarachnoid hemorrhage.

* * * * *